(12) United States Patent
Govindaraju et al.

(10) Patent No.: US 9,230,708 B2
(45) Date of Patent: Jan. 5, 2016

(54) SELF ASSEMBLY OF NAPHTHALENE DIIMIDE DERIVATIVES AND PROCESS THEREOF

(75) Inventors: Thimmaiah Govindaraju, Bangalore (IN); Manjula Basavanna Avinash, Bangalore (IN); Makam Pandeeswar, Bangalore (IN)

(73) Assignee: Jawaharlal Nehru Centre for Advanced Scientific Research, Bangalore (IN)

( * ) Notice: Subject to any disclaimer, the term of this patent is extended or adjusted under 35 U.S.C. 154(b) by 127 days.

(21) Appl. No.: 13/980,038

(22) PCT Filed: Jul. 4, 2011

(86) PCT No.: PCT/IB2011/052939
§ 371 (c)(1),
(2), (4) Date: Jul. 16, 2013

(87) PCT Pub. No.: WO2012/098439
PCT Pub. Date: Jul. 26, 2012

(65) Prior Publication Data
US 2013/0302587 A1    Nov. 14, 2013

(30) Foreign Application Priority Data
Jan. 17, 2011  (IN) .............. 159/CHE/2011

(51) Int. Cl.
| H01B 1/00 | (2006.01) |
|---|---|
| H01L 51/00 | (2006.01) |
| C07K 5/00 | (2006.01) |
| H01B 1/12 | (2006.01) |
| C07D 471/06 | (2006.01) |
| C07K 5/065 | (2006.01) |
| C07K 5/078 | (2006.01) |

(52) U.S. Cl.
CPC .............. *H01B 1/121* (2013.01); *C07D 471/06* (2013.01); *C07K 5/06078* (2013.01); *C07K 5/06156* (2013.01); *H01L 51/0072* (2013.01); *Y10T 428/298* (2015.01); *Y10T 428/2982* (2015.01)

(58) Field of Classification Search
CPC ............ H01B 1/00; H01B 1/12; H01B 1/121; H01L 51/0053; C07D 221/20; C07D 471/02; C07D 471/06
See application file for complete search history.

(56) References Cited

U.S. PATENT DOCUMENTS

2011/0180784 A1* 7/2011 Shukla et al. .................. 257/40

FOREIGN PATENT DOCUMENTS

| WO | WO2012142460 A1 * | 10/2012 |
|---|---|---|
| WO | WO2013096915 A1 * | 6/2013 |

OTHER PUBLICATIONS

Shao et al., "Self-Assembly of 1-D n-Type Nanostructures Based on Naphthalene Diimide-Appended Dipeptides", JACS, vol. 131, 2009, 16374-16376.*

(Continued)

*Primary Examiner* — Mark Kopec
(74) *Attorney, Agent, or Firm* — Ladas & Parry, LLP

(57) ABSTRACT

The present disclosure is in relation to nanotechnology/nanobiotechnology, in particular to nano, meso and micro structures of Naphthalene diimide derivatives. The disclosure provides a method for supramolecular self-assembling of Naphthalene diimide derivatives, its characteristics and its applications. The present disclosure also relates to self assembled nano, meso or micro-structures of the Naphthalene diimide derivatives.

7 Claims, 45 Drawing Sheets

(56) References Cited

OTHER PUBLICATIONS

Pantos et al "Hydrogen-bonded helical organic nanotubes", Agnew. Chem. Int. Ed. 2007, 46, 194-197 (2007).*

Rahaman et al "Structural variations on self-assembley and macroscopic properties of 1,4,5,8-naphthalene-diimide chromophores", Chem. Mater. 2011, 23, 95-105 (pub on web Dec. 9, 2010).*

Colquhouon et al "Induced-fit binding of pi-electron-donor substrates to macrocyclic aromatic ether imide sulfones . . . ", Chem. Eur. J. 2010, 16, 907-918 (pub on web.*

Horne, W., et al. "Modulating charge transfer through cyclic D, L-α-peptide self-assembly." *Chemistry*—A European Journal (Feb. 4, 2005), 11(4), 1137-1144 CODEN: CEUJED; ISSN: 0947-6539.

Campos, Ivana B., et al. "Photoinduced electron transfer in silica-supported self-assembled thin films containing a 1, 4, 5, 8-naphthalenetetracarboxylic diimide and Cytochrome c." Journal of Materials Chemistry (2004), 14(1), 54-60 CODEN: JMACEP; ISSN: 0959-9428.

Susarova, Diana K. et al, "Donor-acceptor complex formation in evaporated small molecular organic photovoltaic cells". Solar Energy Materials & Solar Cells (2010), 94(5), 803-811 CODEN: SEMCEQ; ISSN: 0927-0248.

Shao, H., et al.. "Amphiphiic Self-Assembly of an n-Type Nanotube." Angew. Chem. Int. Ed.. 2010, 49:7688-7691.

Pantos, G., et al. "Hydrogen-Bonded Helical Organic Nanotubes." Angew. Chem. Int. ed.. 2007, 46: 194-197.

Sheshanath V., et al. "Chemistry of naphthalene diimides." Chem. Soc. Rev., 2008. 37:331-342.

ISR for corresponding PCT/IB2011/052939 mailed on Jan. 4, 2012.

IPRP for corresponding PCT/IB2011/052939 completed on Oct. 12, 2012.

* cited by examiner

1. $R_1 = C_7H_7$

2. $R_1 = C_9H_8N$

4. $R1 = R2 = C_7H_7$

5. $R1 = C_7H_7$, $R2 = C_9H_8N$

6. $R1 = R2 = C_9H_8N$

SELF ASSEMBLY OF NAPHTHALENE DIIMIDE DERIVATIVES AND PROCESS THEREOF

CROSS-REFERENCE TO RELATED APPLICATIONS

This application is the U.S. national stage of International Patent Application no. PCT/IB2011/052939, filed on Jul. 4, 2011, which claims priority from Indian Patent Application No. 159/CHE/2011, filed on Jan. 17, 2011, the disclosures of which are hereby incorporated by reference in their entireties.

TECHNICAL FIELD

The present disclosure is in relation to nanotechnology/nanobiotechnology, in particular to nano, meso and micro structures of Naphthalene diimide derivatives. The disclosure provides a method for supramolecular self-assembling of Naphthalene diimide derivatives, its characteristics and its applications. The present disclosure also relates to self assembled nano, meso or microstructures of the Naphthalene diimide derivatives.

BACKGROUND

Organic semiconductor based electronics relies on the non-covalent interactions induced organization of π-conjugated materials. To realize the extensive applications of organic electronic devices, both p and n-type organic semiconductors are essential. The p-type organic semiconductors have been thoroughly investigated over the past decades. However, the n-type organic semiconductors are lagging behind the performances of p-type semiconductors. Naphthalene diimides (NDIs) are among the most promising n-type semiconductors for organic material based electronic devices. NDI finds potential applications in organic field effect transistors, supramolecular switches, fluorescent chemosensors, electron and energy transfer systems. NDIs possess excellent characteristics for the construction of artificial photosystems. Planarity and high π-acidity of NDI system is ideal for face to face π-stacking.

Moreover, the enhanced solubility offers better processability over other aromatic imides. In spite of its several merits the self-assembly of NDI is largely unexplored. For the potential applications of organic semiconductors in electronics, tuning the molecular interactions and hence the morphology to desired architectures is the need of the day.

Fabrication of new nanomaterials using natural building blocks such as amino acids, peptides and proteins is a fascinating area of research in recent years. Peptides based materials have been showed to be a great promise in the "bottom up" approach due to their diverse chemical and physical properties. They can be synthesized in large amounts and can be modified/decorated with functional elements which can be used in diverse applications. The simplest peptide assemblies are of dipeptide assemblies, which are the excellent building blocks for the formation of more complex nanostructures. Self-assembled nanostructures of dipeptide building blocks may find variety of applications such as in controlled drug delivery systems, in the field of tissue engineering, energy-related applications, biomineralisation, molecular electronics and biomaterial science.

Among organic electronic materials, 1,4,5,8-napthalenediimides (NDIs) are attractive due to their n-type semiconducting property and air stability. These are compact electron deficient class of aromatic compounds having tendency to form n-type semiconductor materials. NDI derivatives have got wide range of applications in biological, biomedical as well as in supramolecular chemistry. Its derivatives have been used as intercalators of DNA, chemotherapy, conducting materials, optical brighteners, electrophotography, fluorescent labelling systems, metalomacrocycles, models for the photosynthetic reaction centre (due to ease of synthesis and electron accepting properties), sensors (seven different positional isomers of dihydroxynaphthalene and DNA sensing) and anticancer agents. Because of their desired electronic, spectroscopic and enhanced solubility properties NDIs can act as ideal components for the creation of supramolecular functional materials (donor-acceptor complexes, barrels, catenanes and rotaxanes). The absorption and emission bands of NDIs are variable upon functionalization through the diimide nitrogens or via core substitution. Photophysical properties of N,N-dialkyl-substituted NDIs have been studied. The absorption and emission spectra of these compounds are mirror images to each other and readily aggregate in acetonitrile and in aqueous medium. In aromatic solvents (toluene) excimer-like emissions was observed due to ground-state aggregation. In the case of core substituted NDIs photophysical properties are different than unsubstituted ones, and are highly colourful and conducting functional materials.

1,4,5,8-Naphthalenediimides are neutral, planar, chemically robust, redox-active compounds usually with high melting points. Its derivatives can exhibit relatively high electron affinities, high electron mobility, and excellent chemical, thermal, and photochemical stabilities. Because of its electron transfer behaviour and the ability to tune molecular electronic properties through either variation of substituents on the imide nitrogen atoms or core substitution, they have been used as a building blocks for electronic and optoelectronic devices such as electron-transfer processes, photodetectors, organic light-emitting diodes, optical switches, dye lasers, and also as electron acceptors for studying photo induced energy.

STATEMENT OF THE DISCLOSURE

Accordingly, the present disclosure relates to a method of self assembling naphthalene diimide derivative into nano, meso or micro structures, said method comprising acts of—a) dissolving the naphthalene diimide derivative in a solvent to form a solution and b) adding co-solvent to the solution to obtain the self assembled nano, meso or microstructures; a self assembled nano, meso or micro structure of naphthalene diimide derivative; a method of using self assembled structure of naphthalene diimide derivative as an electronic component, said method comprising act of associating the self assembled structure in an electronic device; and a method of using self assembled structure of naphthalene diimide derivative as a biomaterial, said method comprising act of associating the self assembled structure to a subject in need thereof.

BRIEF DESCRIPTION OF ACCOMPANYING FIGURES

In order that the disclosure may be readily understood and put into practical effect, reference will now be made to exemplary embodiments as illustrated with reference to the accompanying figures. The figure together with a detailed description below, are incorporated in and form part of the specification, and serve to further illustrate the embodiments and explain various principles and advantages, in accordance with the present disclosure where:

FIG. 1A shows UV-vis spectra of NDI 1 (a) and NDI 2 (b) in acetonitrile (100 μM) with increasing percentage of added water. UV-vis spectra of NDI 1 (c) and NDI 2 (d) in 10% aqueous acetonitrile (100 μM) with the addition of NaOH (in equiv).

FIG. 1B shows Photophysical studies of L/D-NDI (100 μM) in acetonitrile and 90% aqueous acetonitrile. a) UV-vis, b) fluorescence and c) circular dichroism (CD) spectra. d) Current-voltage (I-V) characteristics obtained by C-AFM on a L-NDI nanosheet of 60 nm topographical thickness. e) Schematic representation of the transition of the angles between the z-polarized transition moments of stacked exciton-coupled L-NDI (NDI-3A and D-NDI (NDI-3B). I): L-NDI in acetonitrile, II): L-NDI in 90% aqueous acetonitrile, III): D-NDI in acetonitrile and IV): D-NDI in 90% aqueous acetonitrile.

FIG. 2 shows general chemical structures of amino acid/peptide appended naphthalenediimide (NDI). Where $R_1=R_2$ or $R_1 \neq R_2$, $R_1$ and $R_2$ can be any natural or unnatural amino acids, peptide containing natural or unnatural amino acids. Peptide can be of heterogonous or homogeneous sequence of amino acids Amino acids can be of aromatic, aliphatic, polar, nonpolar, cationic, anionic and neutral. R3, R4, R5 and R6 are core substituents of any nature, cyclic, fused or acyclic FIG. 3 shows CD spectra of NDI 1 (a) and NDI 2 (b) in acetonitrile (100 μM) with increasing percentage of added water. CD spectra of NDI 1 (c) and NDI 2 (d) in 10% aqueous acetonitrile (100 μM) with added NaOH (in equiv). Concentration dependent CD spectra of NDI 1 (e) and NDI 2 (f) in acetonitrile.

Figure 7:
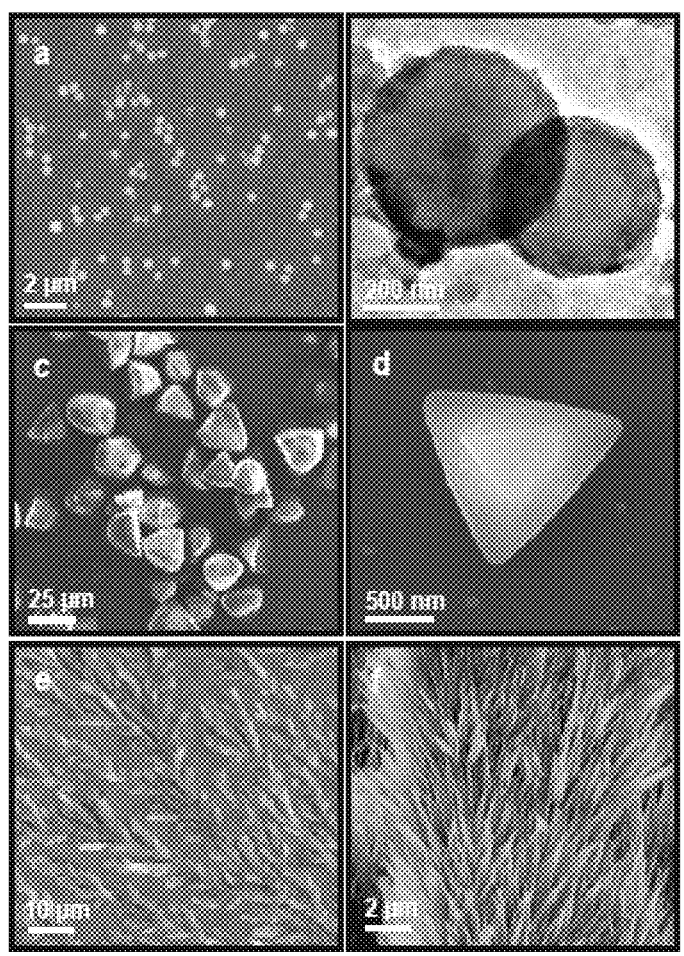

FIG. 7 shows (a) FESEM micrograph of NDI 1 nanospheres obtained from 100% acetonitrile solution. (b) The corresponding TEM micrograph of NDI 1 nanospheres. (c) FESEM micrograph of NDI 1 traingular particles obtained from 90% aqueous acetonitrile solution. (e) FESEM micrograph of NDI 1 fractals formed by 10% aqueous acetonitrile solution containing 2 equiv of NaOH. (d) and (f) are corresponding high magnification micrographs of (c) and (e) respectively.

Figure 8:
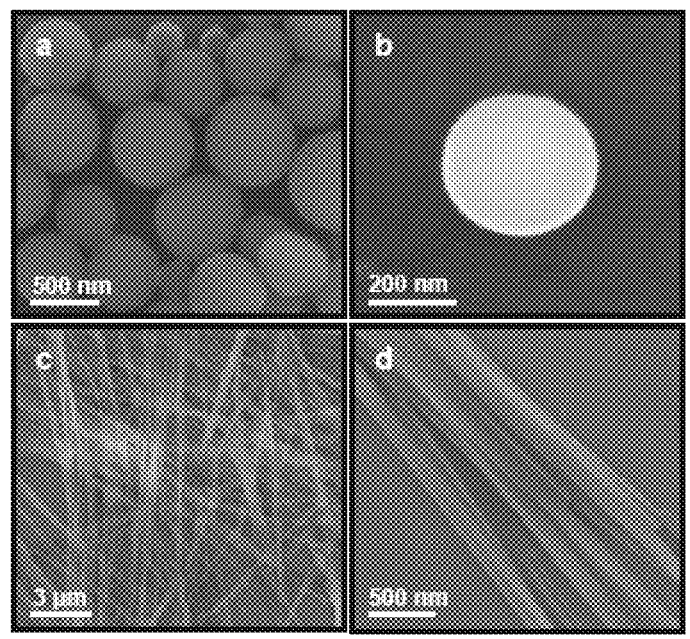

FIG. 8 shows FESEM micrographs of NDI 2 nanospheres obtained from 100% acetonitrile solution (a) and fibers (bundle of nanobelts) obtained from 60% aqueous acetonitrile (c). (b) and (d) are corresponding high magnification micrographs of (a) and (c) respectively.

Figure 9:
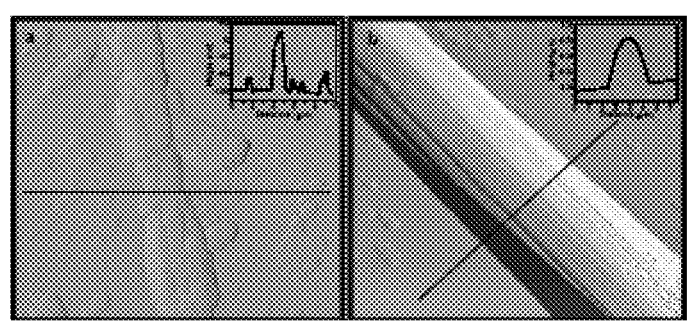

FIG. 9 shows (a) AFM image of NDI 2 showing the structural transition from nanospheres to nanobelts and in turn into microfibers (60% aqueous acetonitrile). (b) AFM image of NDI 2 microfiber (nanobelt bundles) formed from 60% aqueous acetonitrile.

Figure 10:
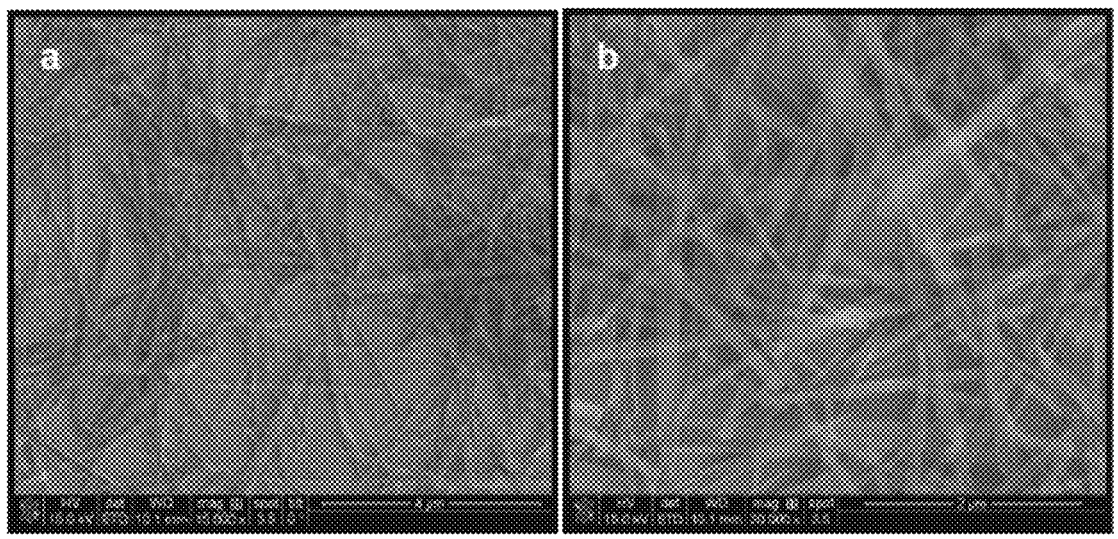

FIGS. 10 (*a*) and (*b*) shows FESEM micrographs of NDI 2 assembled from 1 mM acetonitrile solution.

Figure 11:
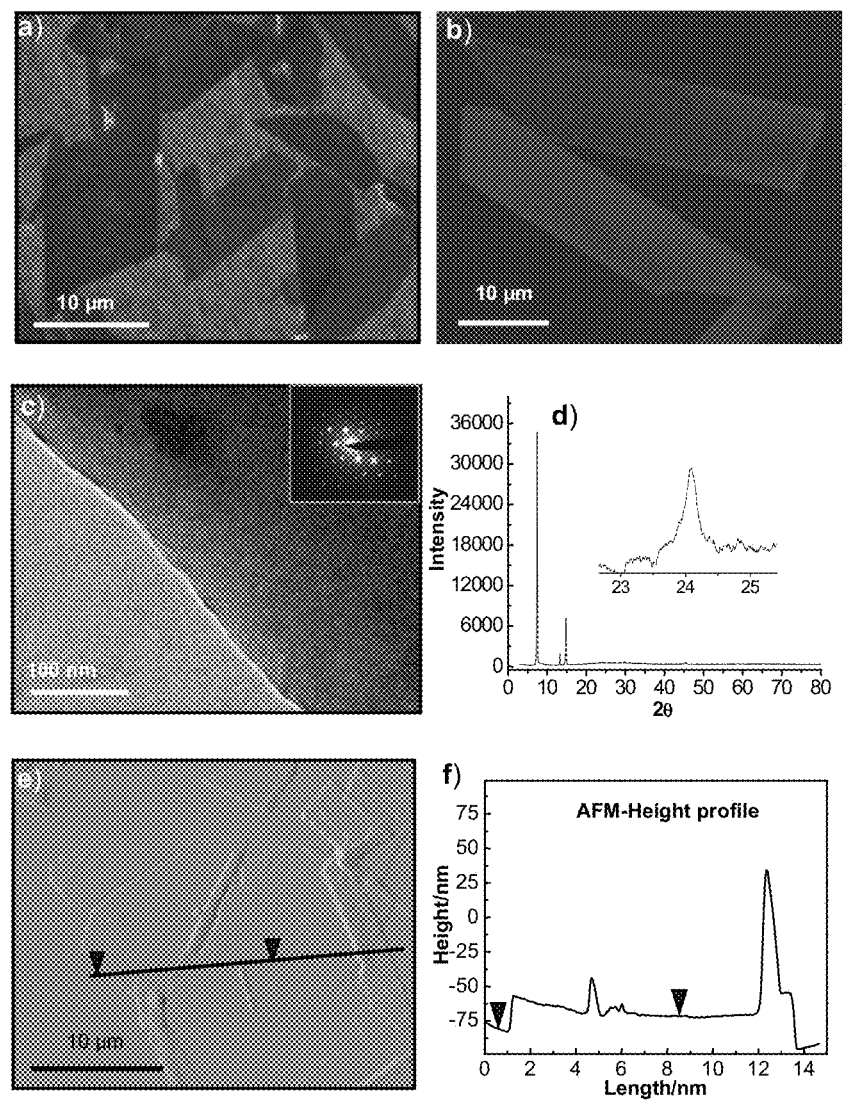

FIG. 11 shows a) FESEM, b) fluorescence confocal c) HRTEM and e) AFM micrographs of L-NDI obtained from 90% aqueous acetonitrile. The inset in c) is the SAED (selected area electron diffraction) pattern recorded on nanosheet revealing the single-crystalline ordering. d) Powder X-ray diffraction pattern of drop casted self-assembled L-NDI nanosheets. The inset corresponds to a d spacing of 3.68 Å. f) The corresponding height profile of AFM micrograph (e). The nanosheet possesses a typical height of ~10 nm.

Figure 12:
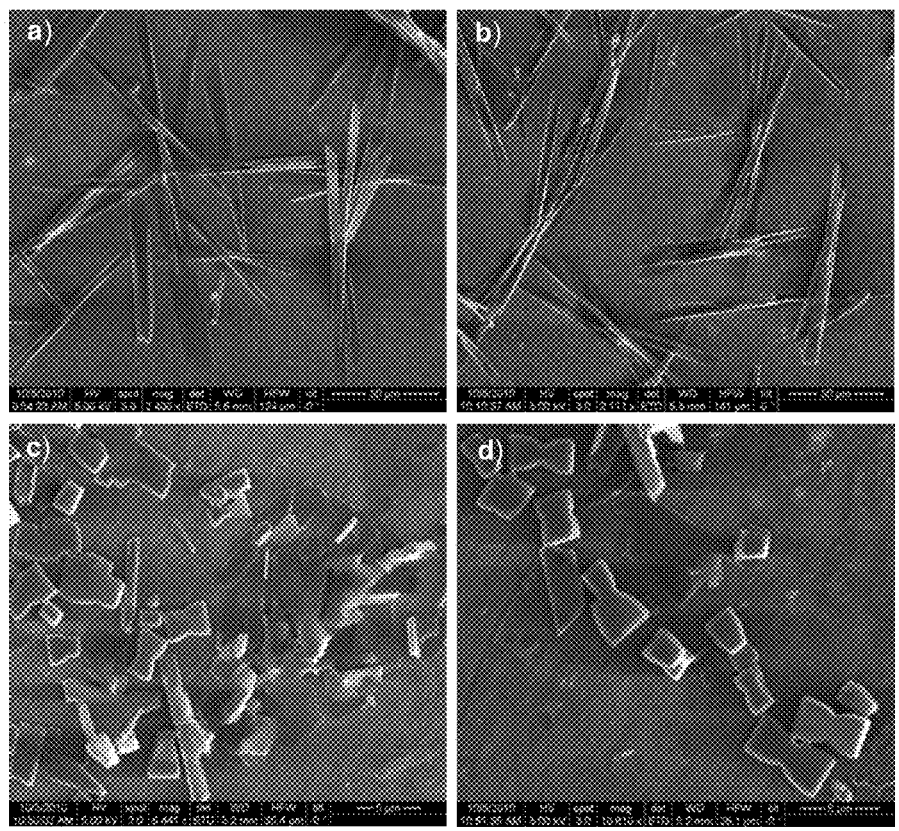

FIG. 12 shows FESEM micrographs of L-NDI obtained from a) and b) 90% aqueous DMF and c) and d) 90% aqueous DMSO respectively.

Figure 13:
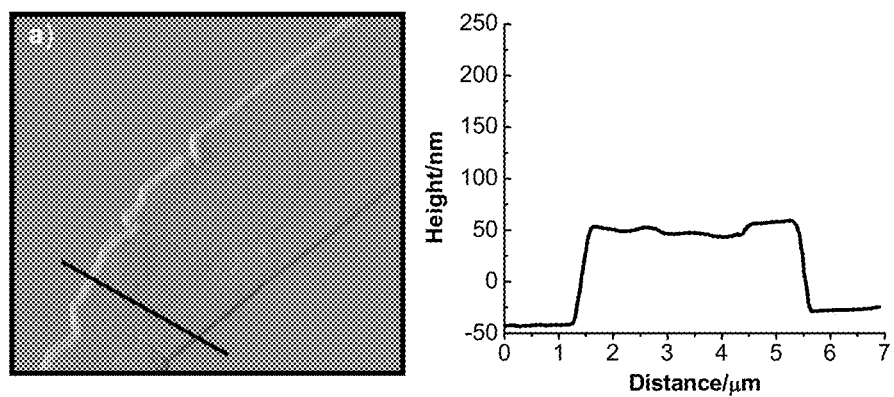

FIG. 13 shows a) AFM micrograph of L-NDI nanosheet obtained from 90% aqueous acetonitrile. b) The corresponding height profile.

Figure 14:
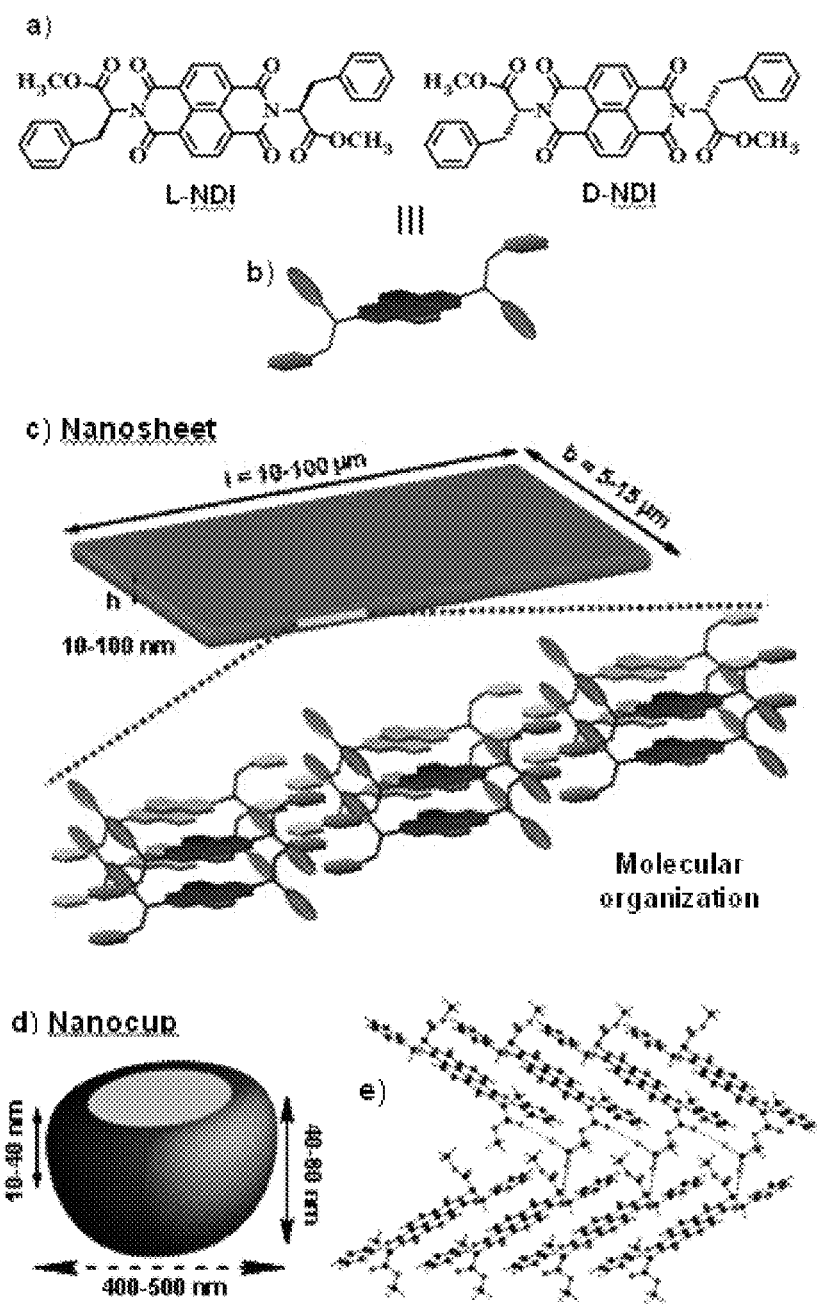

FIG. 14 shows a) Molecular Structures of phenylalanine methylester appended naphthalenediimides (L-NDI and D-NDI) with their pictorial representation (b). c) Proposed molecular packing model for the self-assembled L/D-NDI nanosheets. l=length, b=breadth and h=height (thickness) of the nanosheet. d) Schematic of the L-NDI nanocup obtained from chlorinated co-solvent and e) Molecular packing diagram for L-NDI single crystals grown in chloroform.

Figure 15:
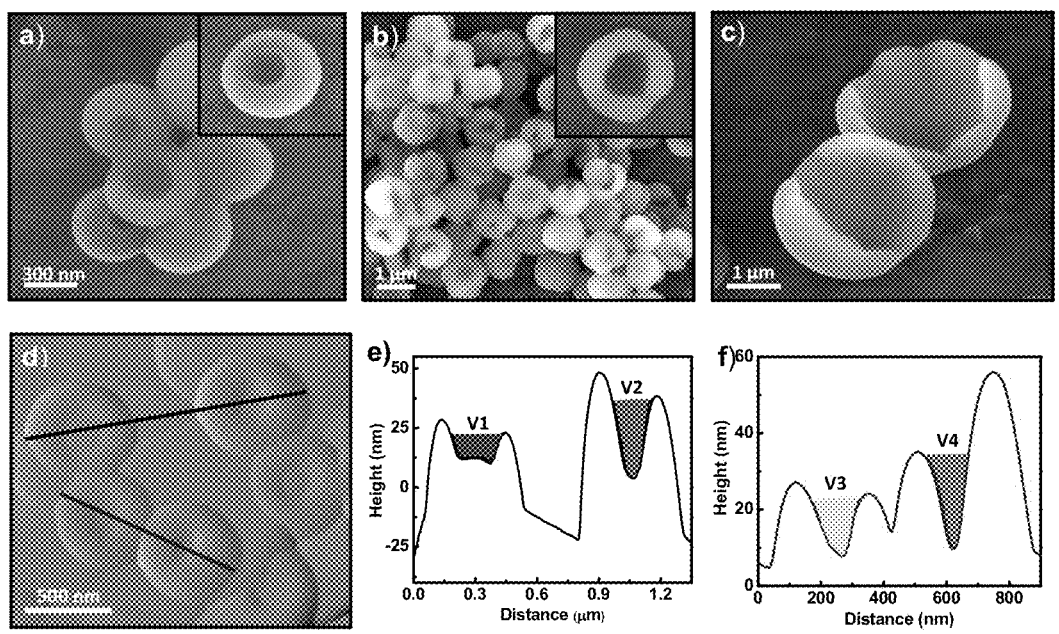

FIG. 15 shows FESEM images of L-NDI a) nanocups obtained from 50% (v/v) $CHCl_3$/MeOH, b) mesocups obtained from 10% (v/v) $CHCl_3$/MeOH, c) bowls from 10% (v/v) $CCl_4$/MeOH and d) AFM micrograph of L-NDI nanocups obtained from 50% (v/v) $CHCl_3$/MeOH. The corresponding height profiles of d) are shown in e) and f) respectively. Container volumes are indicated V1 (red), V2 (green), V3 (yellow) and V4 (cyan).

Figure 16:
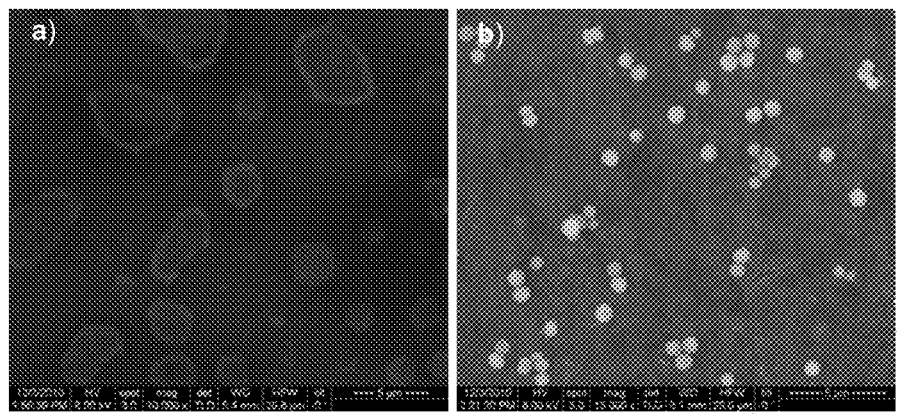

FIG. 16 shows a) and b) FESEM micrograph of L-NDI architectures obtained from 100% chloroform and 100% MeOH respectively.

Figure 17:
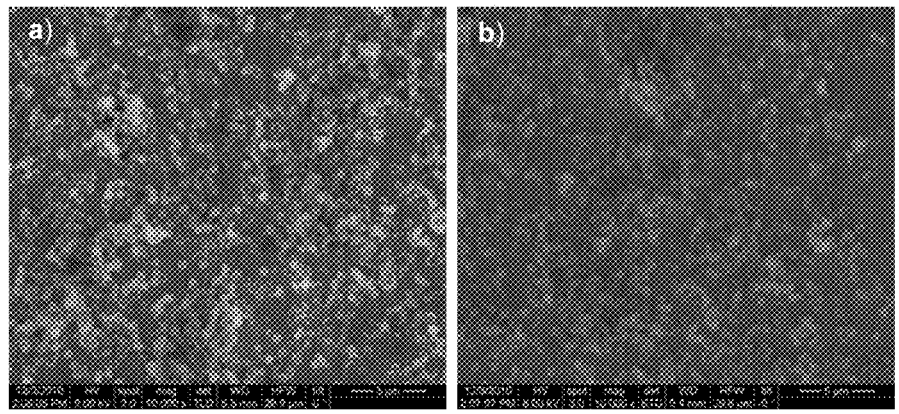

FIG. 17 shows a) and b) FESEM micrograph of L-NDI obtained from 10% (v/v) dichloromethane/MeOH.

Figure 18:
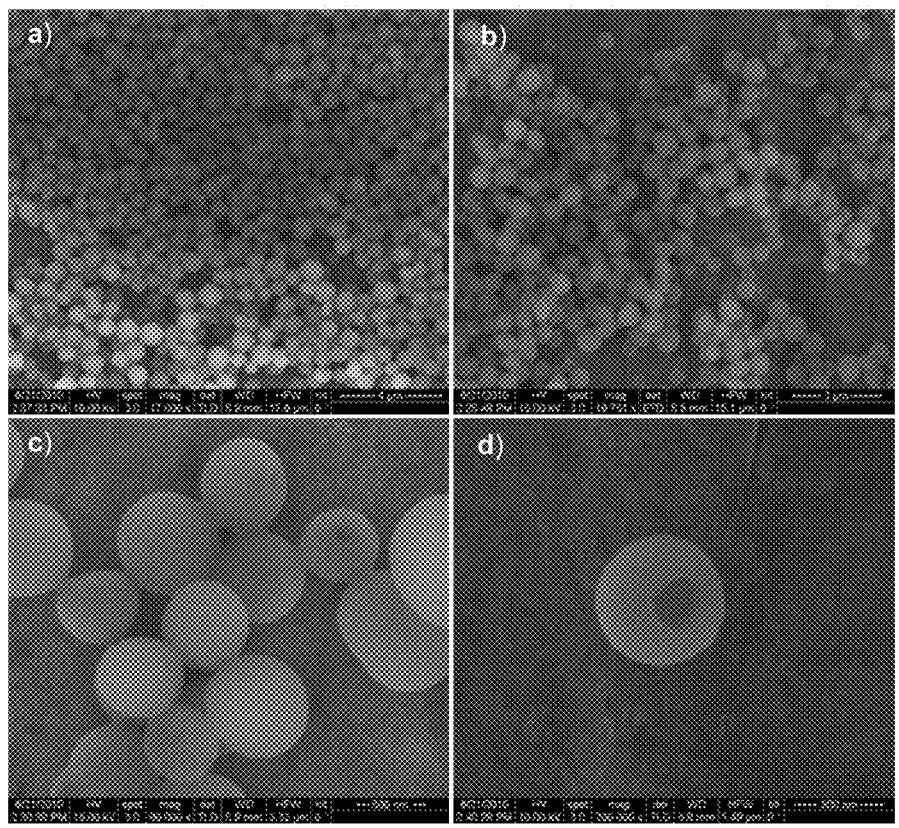

FIGS. 18 *a*), *b*), *c*) and *d*) shows FESEM micrograph of L-NDI architectures obtained from acetonitrile/$CHCl_3$.

Figure 19:
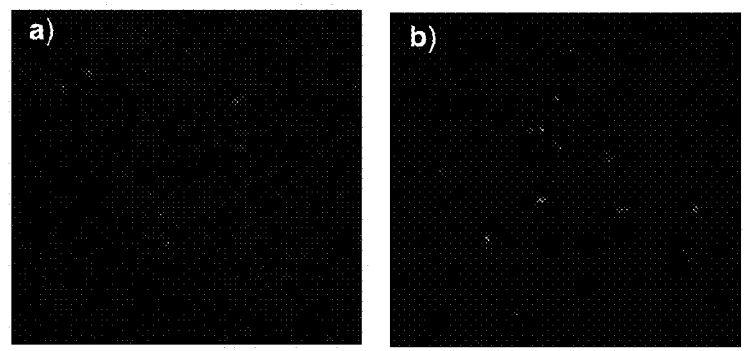

FIG. 19 shows Fluorescence confocal micrographs of L-NDI containers filled with a) rhodamine and b) fluorescein.

Figure 20:
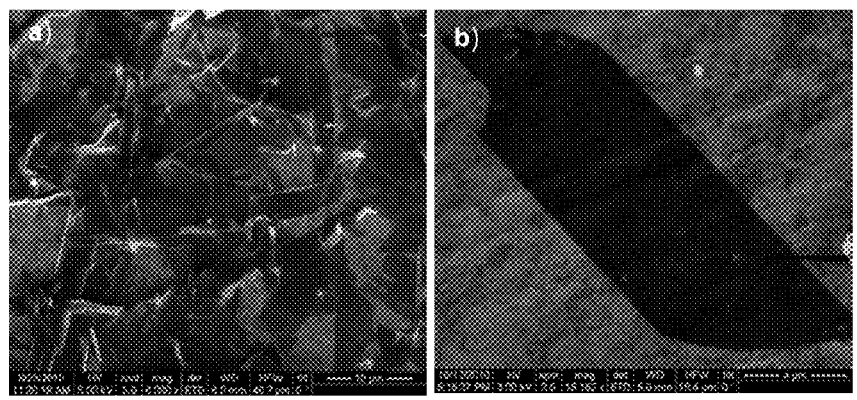

FIGS. 20 *a*) and *b*) shows FESEM micrographs of L-NDI and D-NDI obtained from 90% aqueous acetonitrile respectively.

Figure 21:
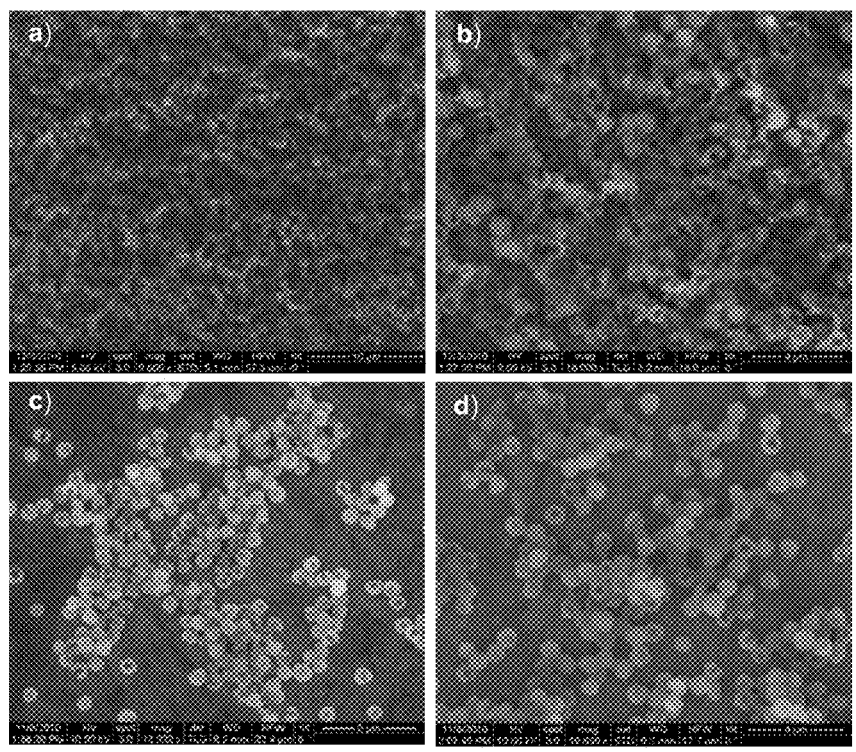

FIGS. 21 *a*), *b*), *c*) and *d*) shows FESEM micrograph of L-NDI obtained from 10% (v/v) chloroform/MeOH.

Figure 22:
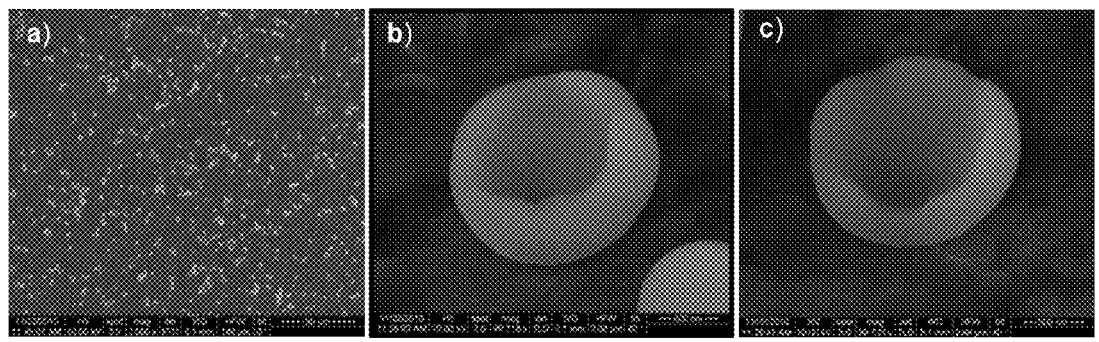

FIGS. 22 *a*), *b*) and *c*) shows FESEM micrographs of L-NDI bowl-like architectures obtained from 10% (v/v) carbontetrachloride/MeOH.

Figure 23:
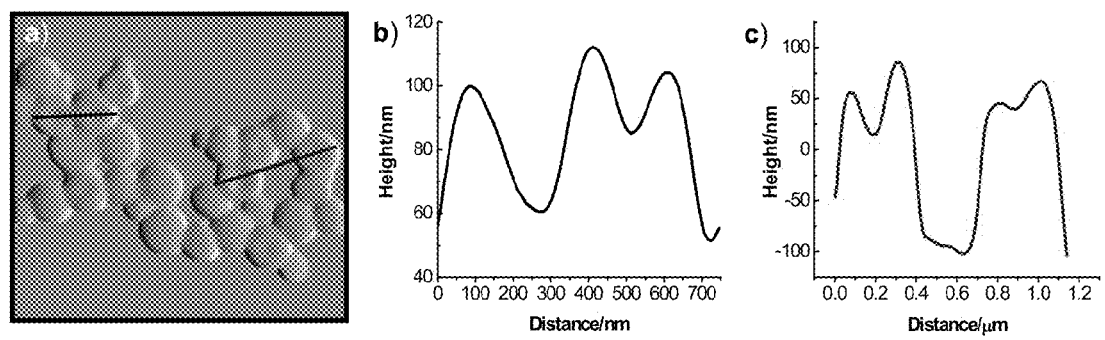

FIG. 23 shows a) AFM micrograph of L-NDI nanocups and the corresponding height profiles are shown in b) and c).

Figure 24:
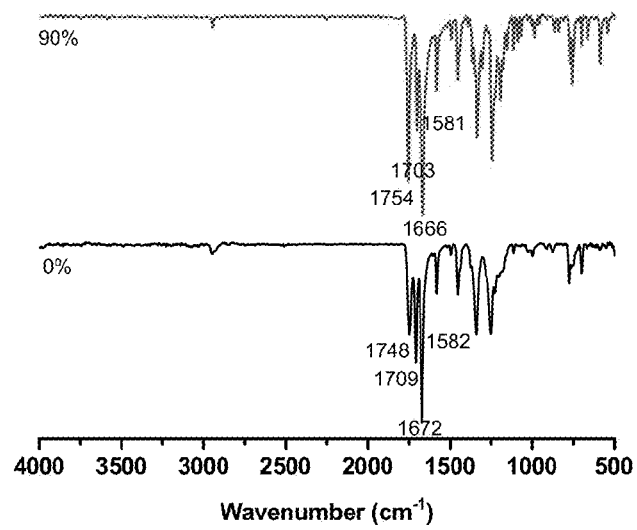

FIG. 24 shows IR spectra of L-NDI obtained from acetonitrile and 90% aqueous acetonitrile.

Figure 25:
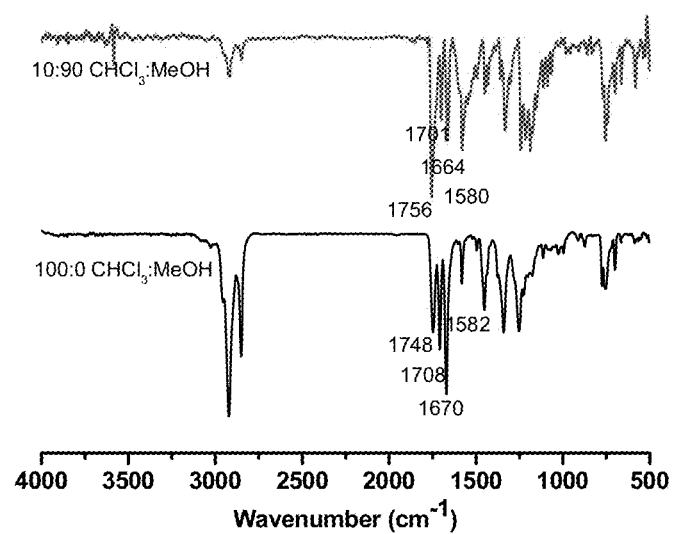

FIG. 25 shows IR spectra of L-NDI obtained from chloroform/MeOH.

Figure 26:
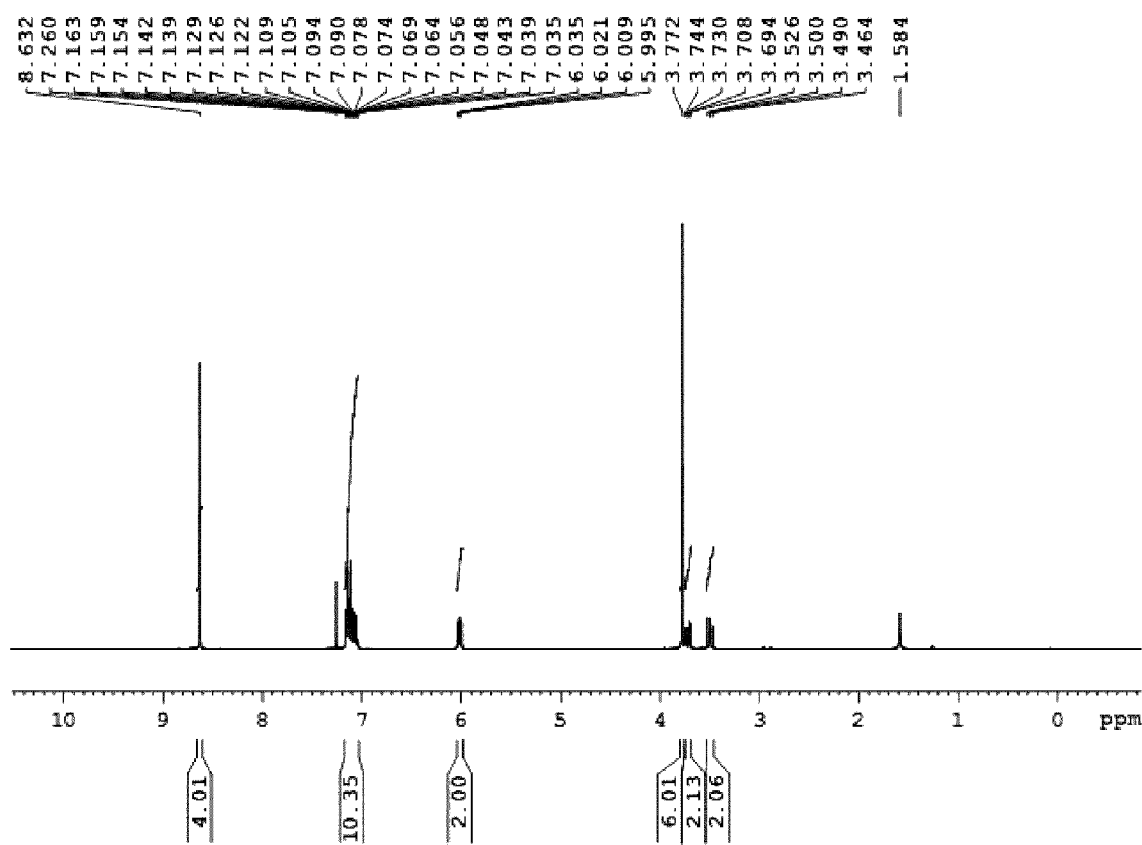

FIG. 26 shows $^1$H NMR of L-phenylalanine methylester appended naphthalenediimide (L-NDI).

Figure 27:
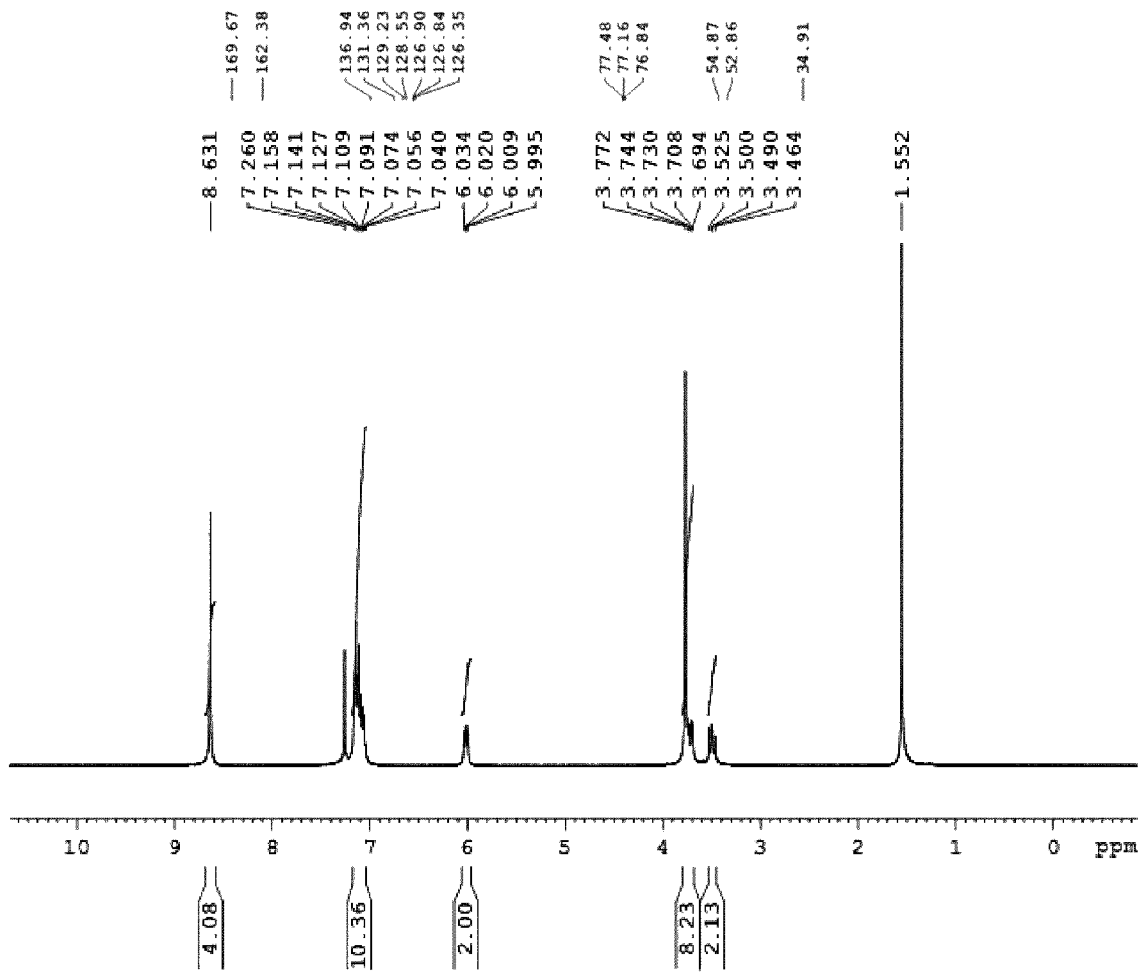

FIG. 27 shows $^{13}$C NMR of L-phenylalanine methylester appended naphthalenediimide (L-NDI).

Figure 28:
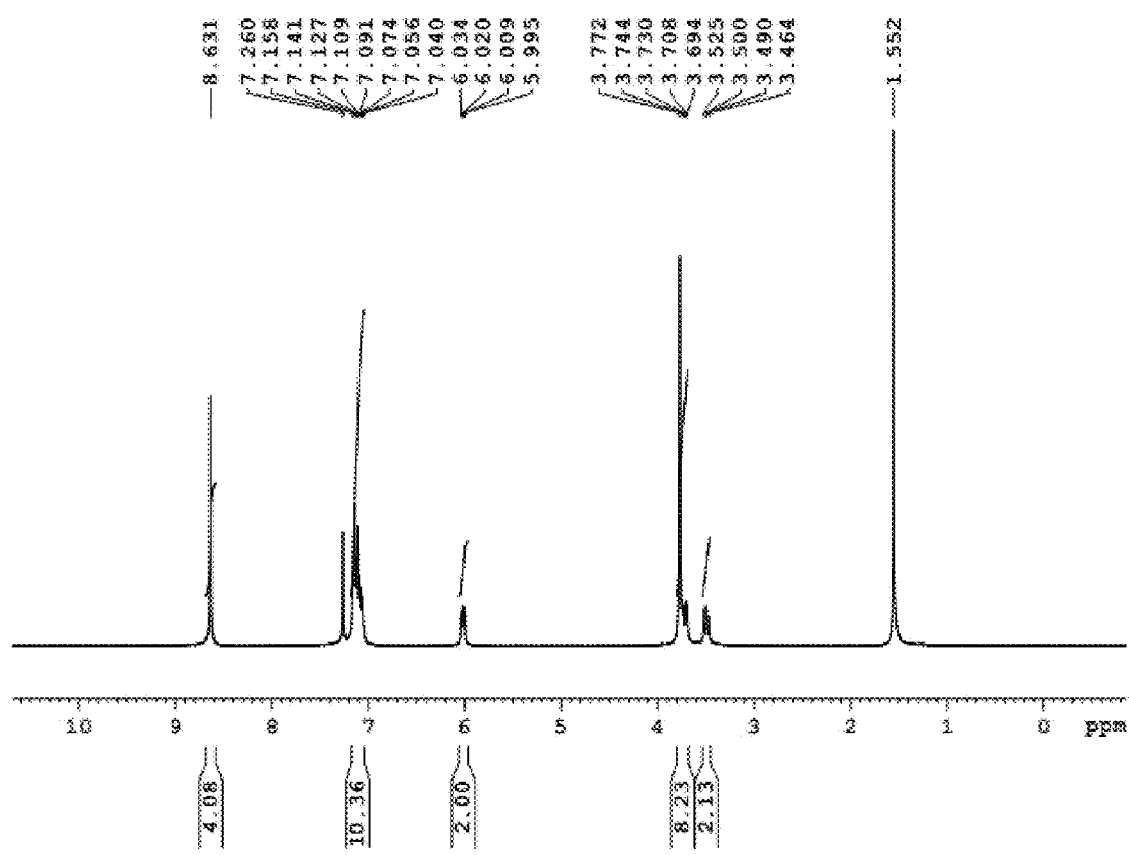

FIG. 28 shows $^1$H NMR of D-phenylalanine methylester appended naphthalenediimide (D-NDI).

Figure 29:
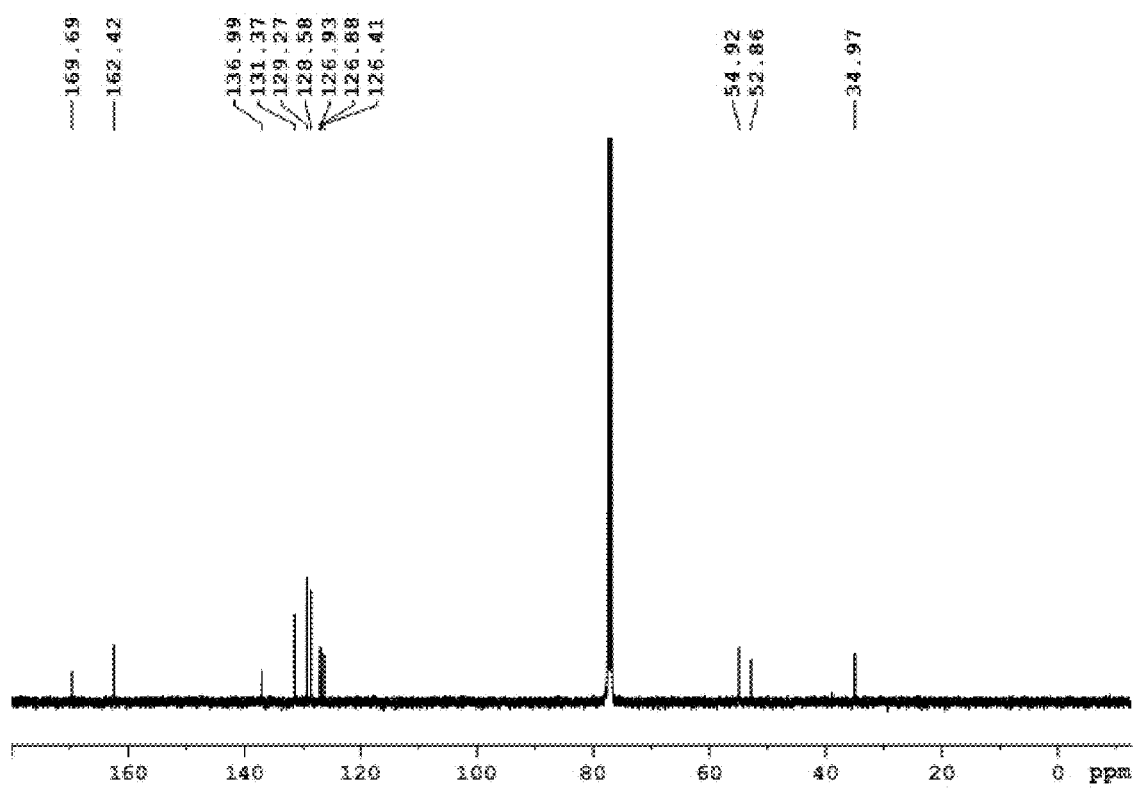

FIG. 29 shows $^{13}$C NMR of D-phenylalanine methylester appended naphthalenediimide (D-NDI).

Figure 30:
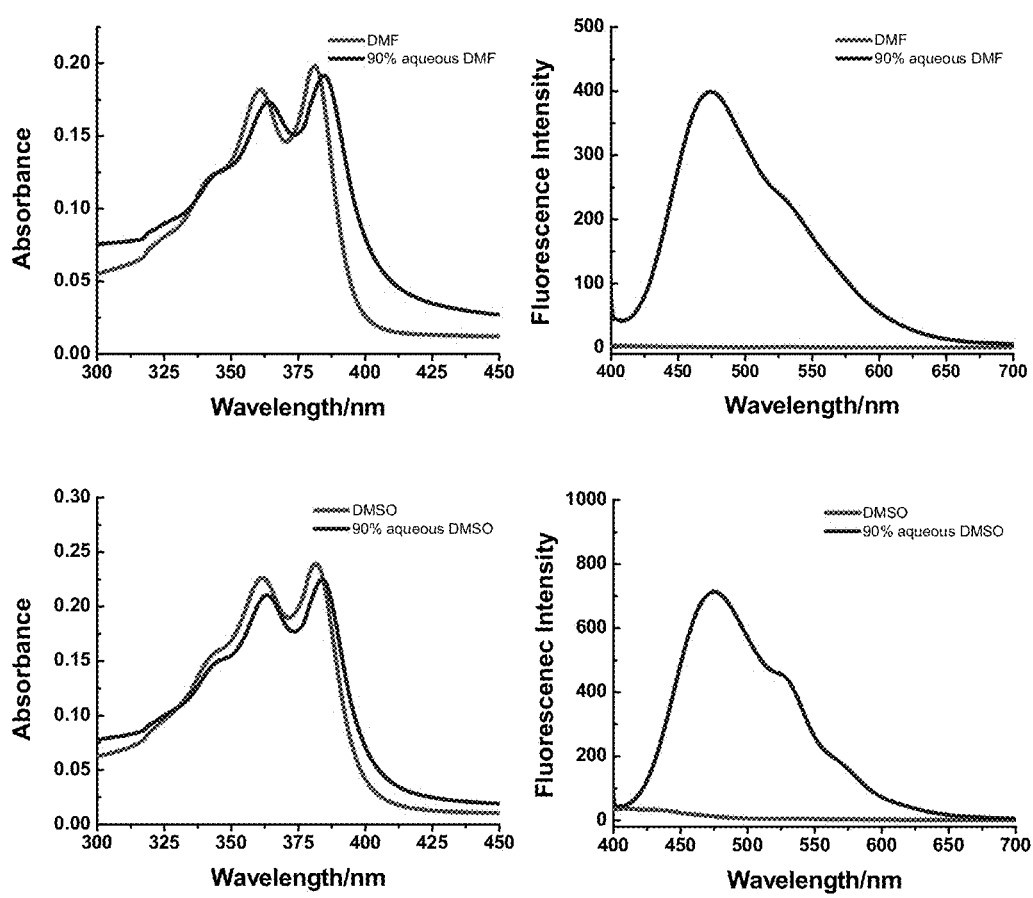

FIG. 30 shows UV-Vis spectra of 100 μM L-NDI in a) DMF and 90% aqueous DMF, c) DMSO and 90% aqueous DMSO. b) and d) the corresponding fluorescence spectra of a) and c) respectively.

Figure 31:
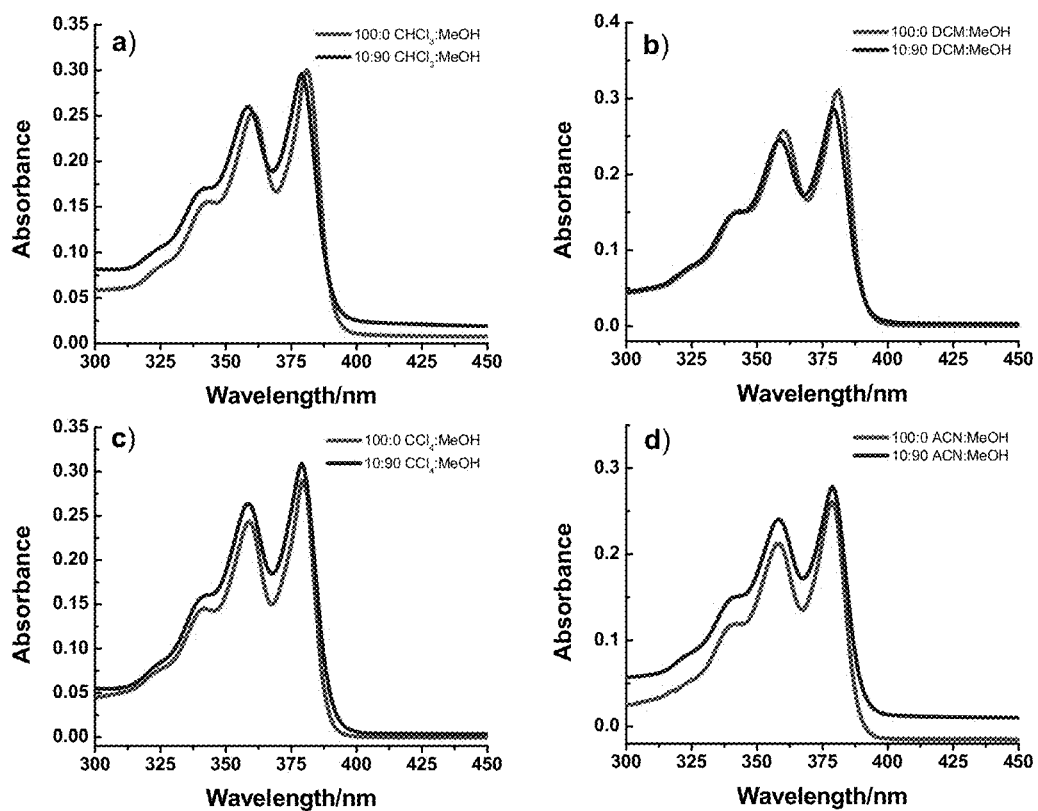

FIG. 31 shows UV-Vis spectra of 100 μM L-NDI in a) chloroform/MeOH, b) dichloromethane/MeOH, c) carbontetrachloride/MeOH and d) Acetonitrile/MeOH respectively.

Figure 32:
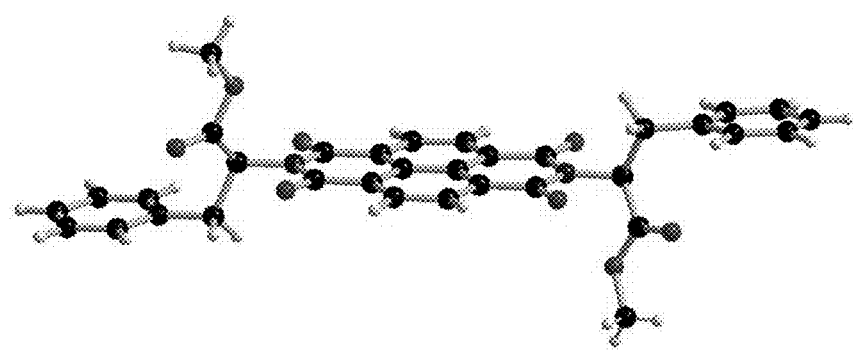

FIG. 32 shows Ortep diagram of L-NDI. Single crystals were grown in chloroform. Solvent chloroform has been removed for clarity.

Figure 33:
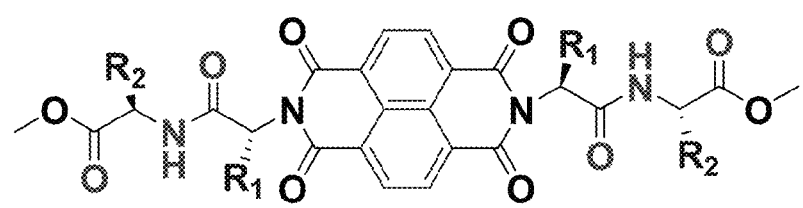

FIG. 33 shows planar NDI and aromatic side chain on dipeptide.

Figure 34:
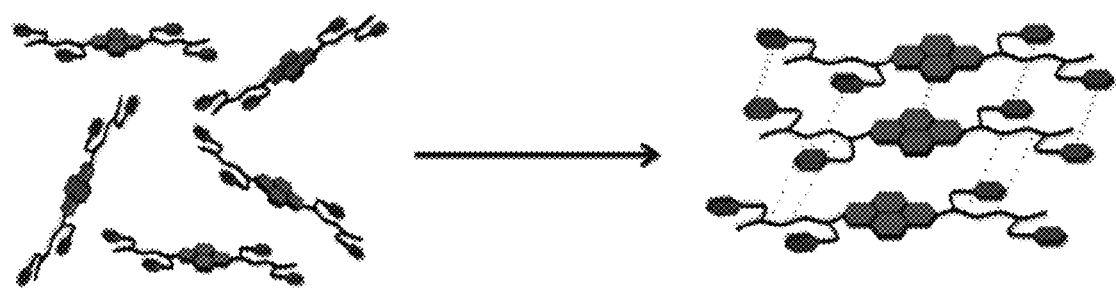

FIG. 34 shows Schematic representation of self-assembly of randomly oriented N,N-bis-(dipeptide) appended NDI molecules into a ordered stacks under appropriate solvent system through H-bonding and π-π interactions.

Figure 35:
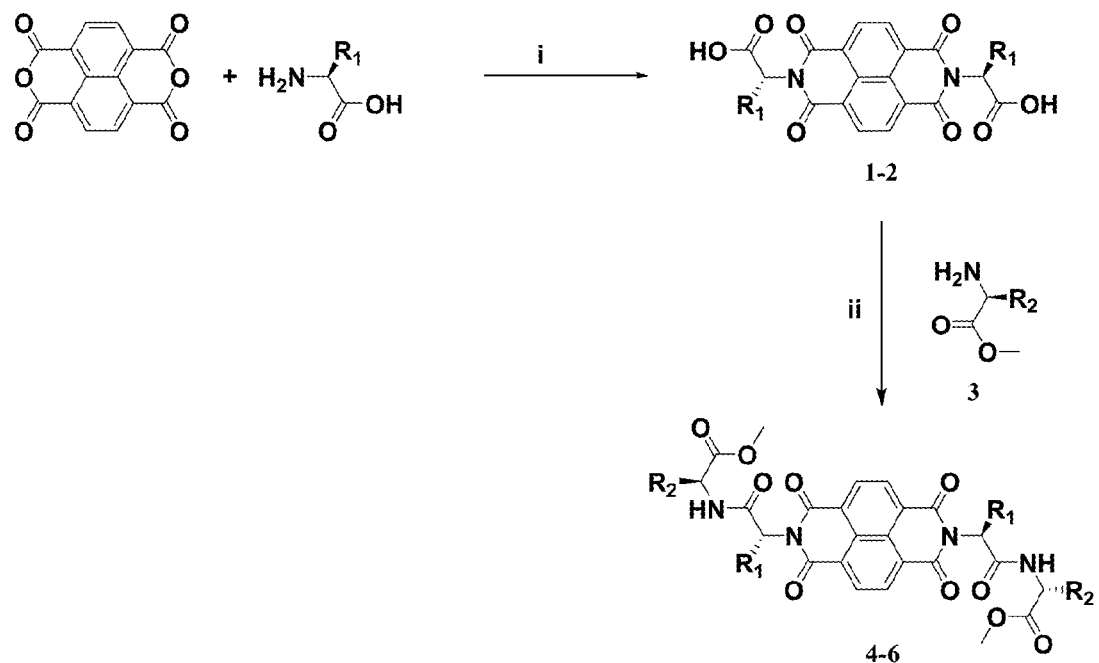

FIG. 35 shows synthesis of N,N-bis-(dipeptide) appended NDIs. Reagents and conditions: (i) $C_6H_{15}N$, DMF, reflux, 12 h. (ii) EDC.HCl, HOBT and DIPEA, DMF, rt, 12 h.

Figure 36:
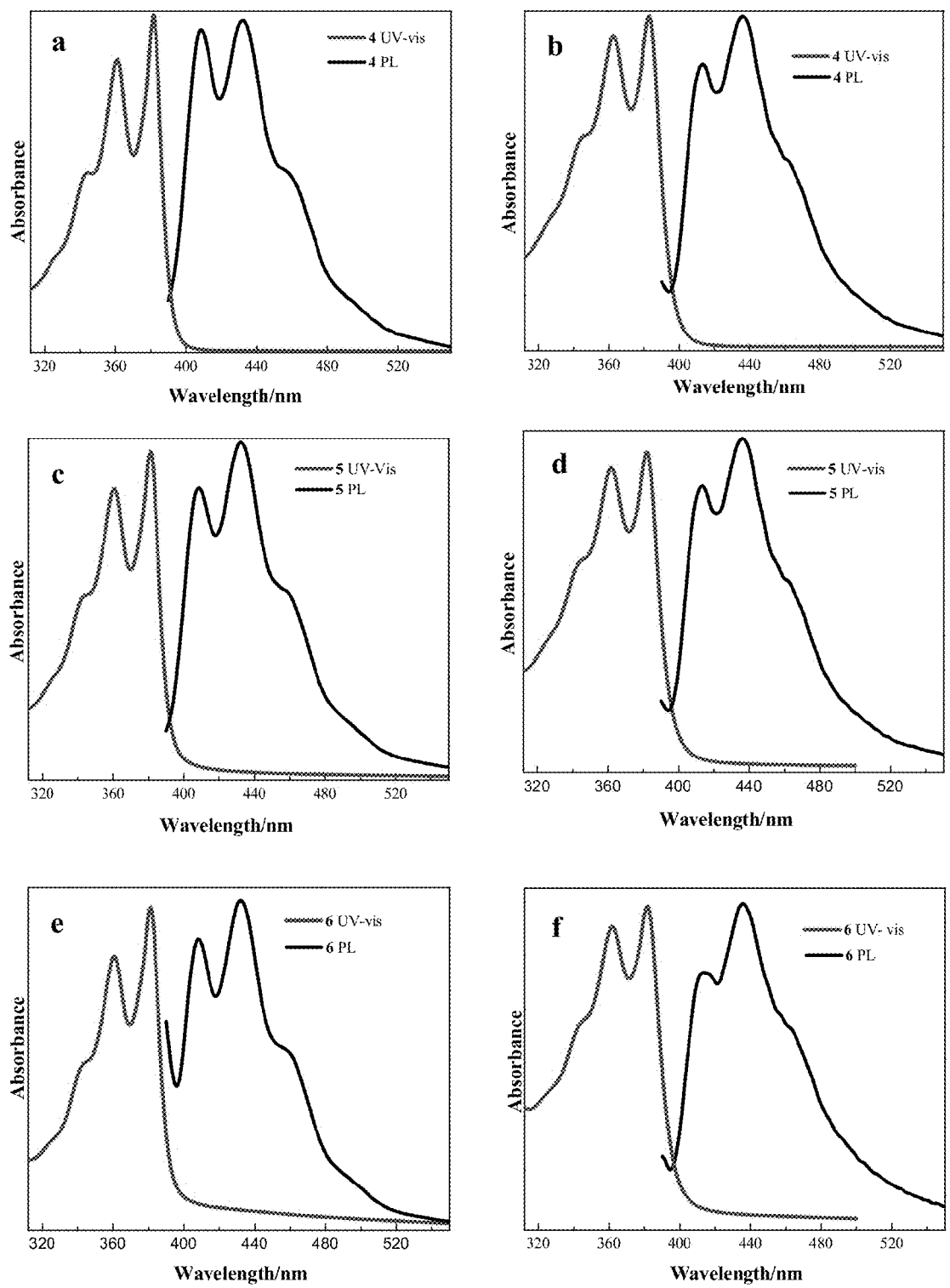

FIG. 36 shows UV-vis absorption (red curve) and Photoluminescence (black curve) studies at $5\times10^{-5}$M (a) absorption and emission (λex=380 nm) of NDI 4 in $CHCl_3$, (b) absorption and emission (λex=380 nm) of NDI 4 in DMSO, (c absorption and emission (λex=380 nm) of NDI 5 in $CHCl_3$ (d) absorption and emission (λex=380 nm) of NDI 5 in DMSO, (e) absorption and emission (λex=380 nm) of NDI 6 in $CHCl_3$, (f) absorption and emission (λex=380 nm) of NDI 6 in DMSO.

Figure 37:
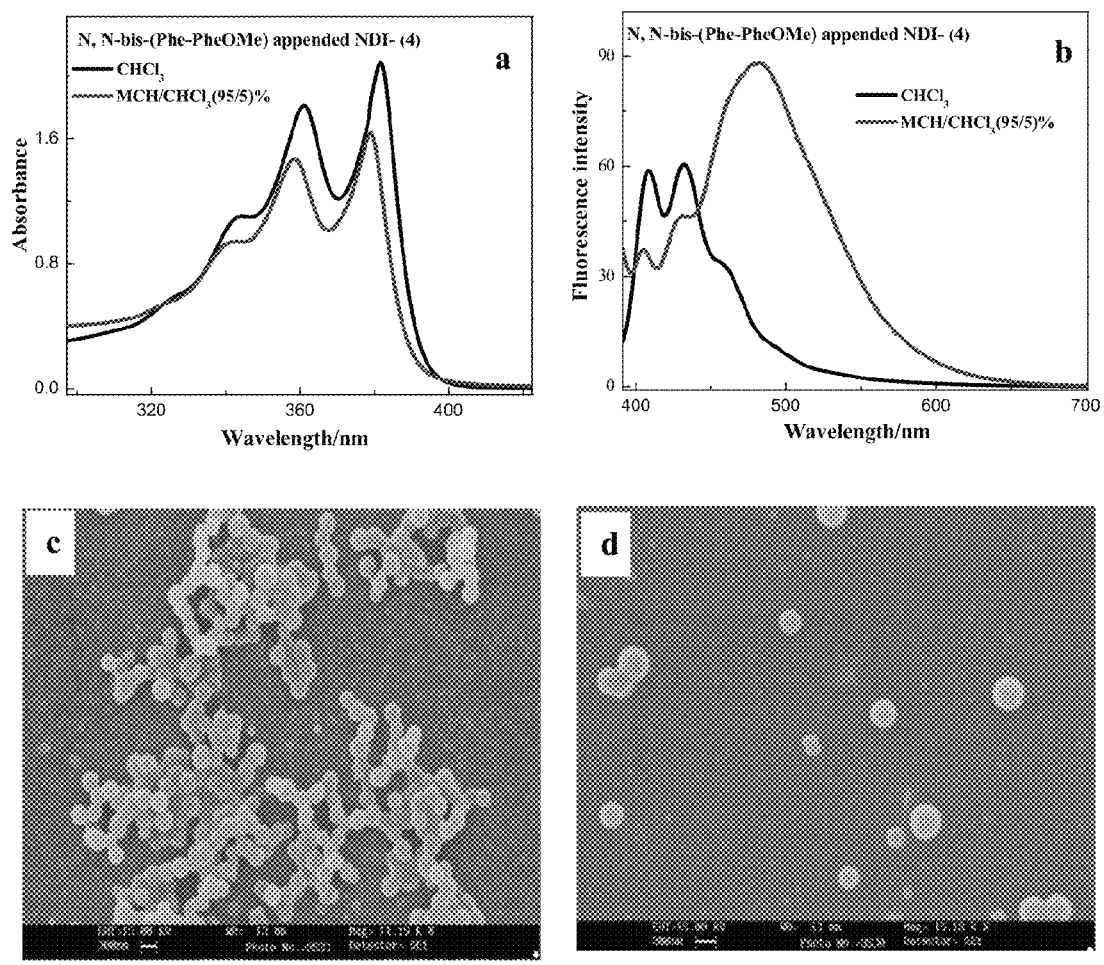

FIG. 37 shows Photophysical studies of NDI 4 ($5\times10^{-5}$ M) in $CHCl_3$ (black curve) and in MCH(methylcyclohexane)/$CHCl_3$(95:5)(red curve). (a) UV-vis spectra, (b) Photoluminescence emission spectra (PL) ($\lambda_{exi}$ at 380 nm), (c) and (d) SEM micrograph of NDI 4 nanospheres obtained from the MCH/$CHCl_3$ (95:5) solvent system on glass substrate.

Figure 38:
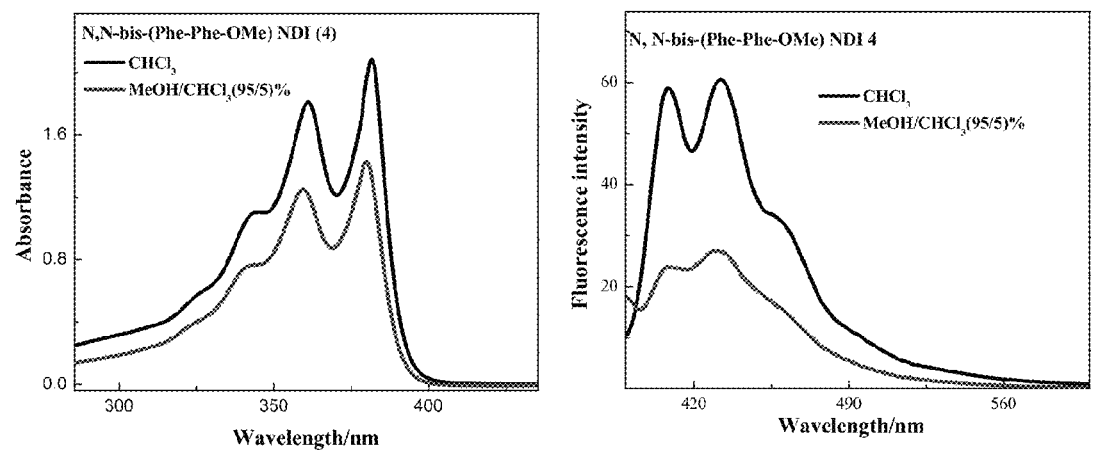

FIG. 38 shows Photophysical studies of NDI 4 ($5\times10^{-5}$ M) in $CHCl_3$ (black curve) and in MeOH/$CHCl_3$ (95:5) (red curve). (a) UV-vis absorption spectra, (b) photoluminescence emission spectra ($\lambda_{exi}$ at 380 nm).

Figure 39:
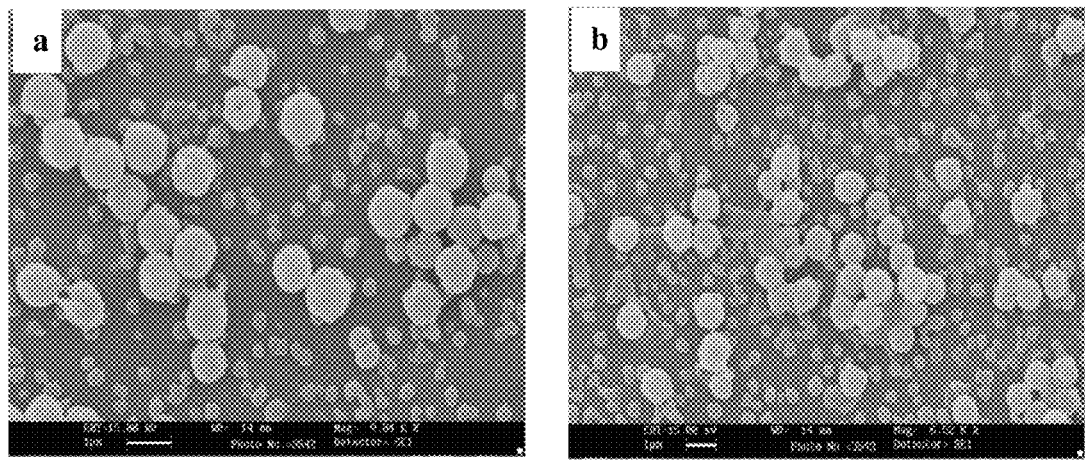

FIG. 39 shows (a) and (b) SEM micrograph open mouth nanovesicles obtained from the solution of NDI 4[MeOH/$CHCl_3$ (95:5)] on glass substrate.

Figure 40:
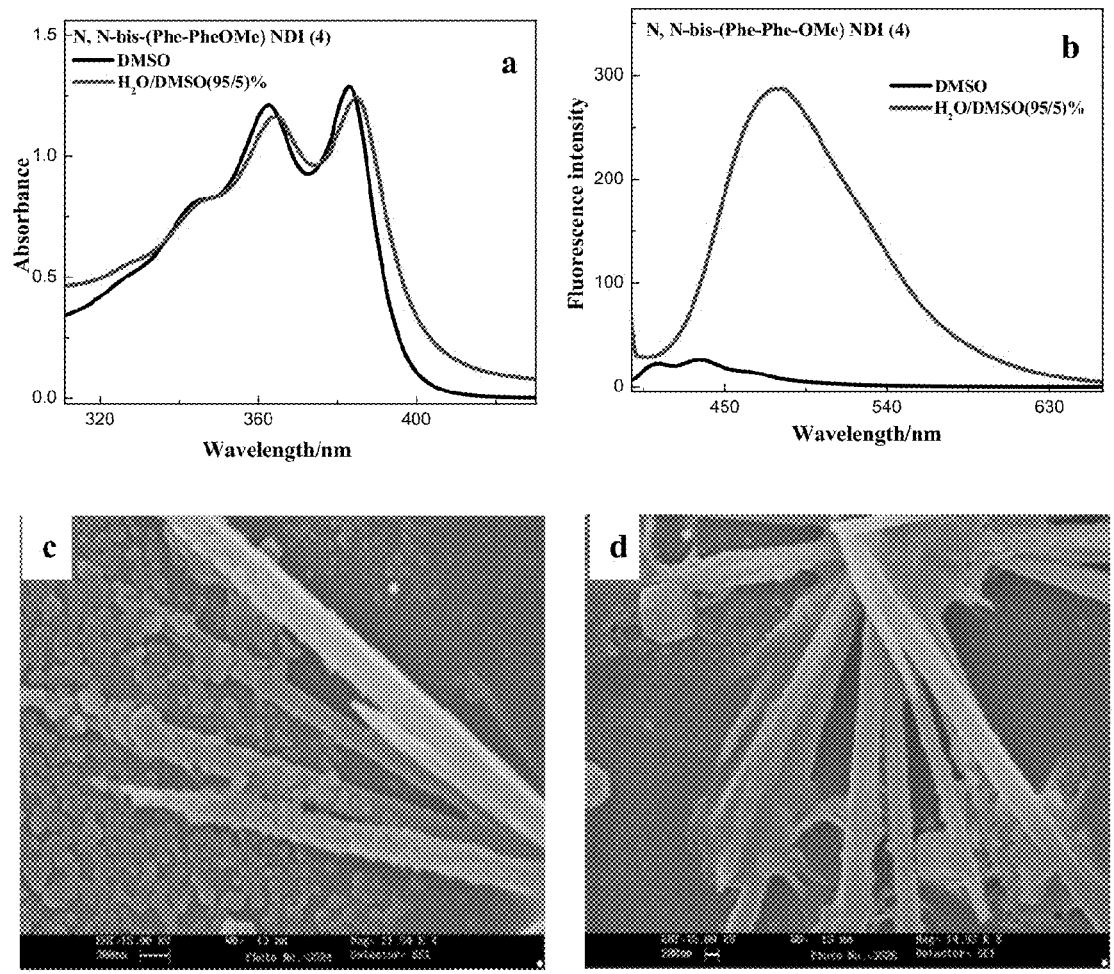

FIG. 40 shows Photophysical studies of NDI 4 ($5\times10^{-5}$ M) in DMSO (black curve) and in $H_2O$/DMSO (95:5) (red curve). (a) UV-vis absorption spectra, (b) photoluminescence emission spectra ($\lambda_{exi}$ at 380 nm), (c) and (d) SEM micrograph of NDI 4 nanotapes obtained from $H_2O$/DMSO (95:5) solvent system on glass substrate.

Figure 41:
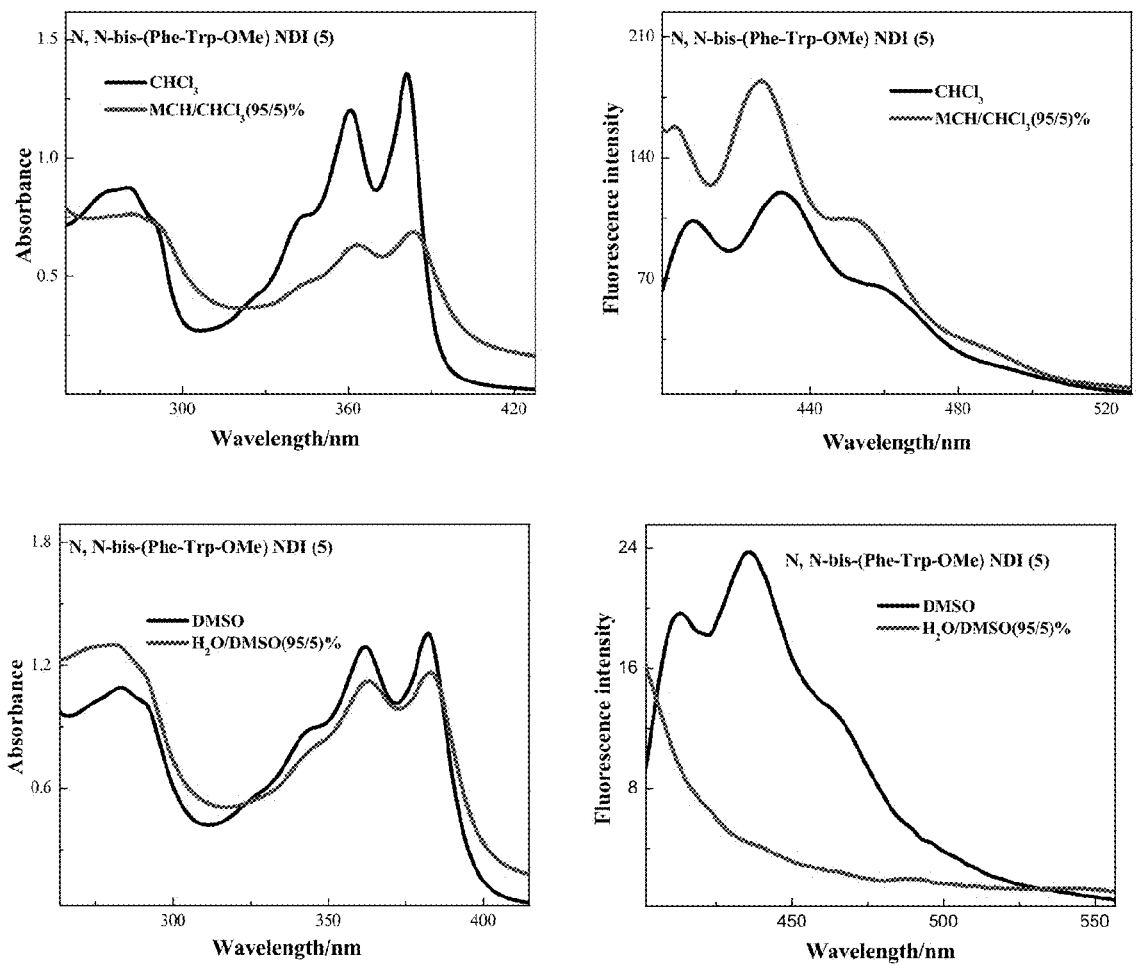

FIG. 41 shows Photophysical studies of NDI 5 ($5\times10^{-5}$ M), UV-vis absorption spectra (a and c), Photoluminescence emission spectra ($\lambda_{exi}$ at 380 nm) (b and d).

Figure 42:
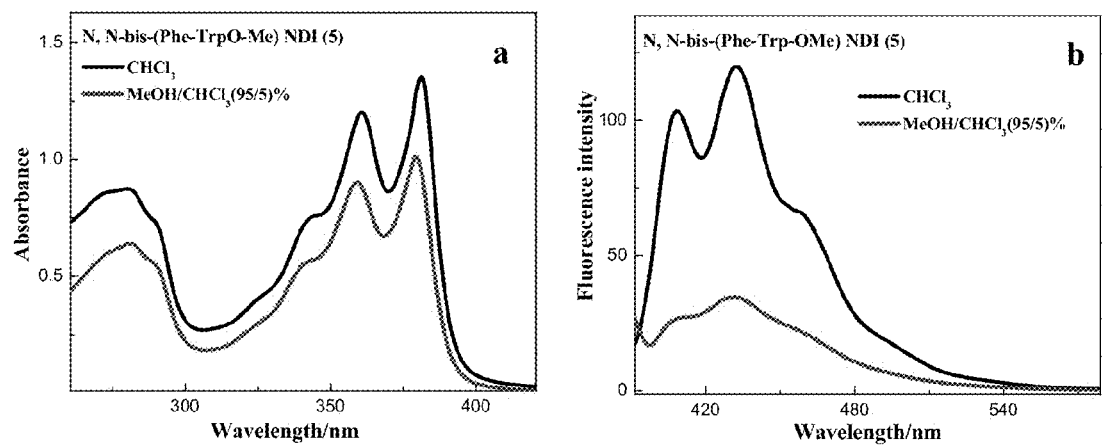

FIG. 42 shows Photophysical studies of NDI 5 ($5\times10^{-5}$ M) in $CHCl_3$ (black curve) and in MeOH/$CHCl_3$ (95:5) (red curve). (a) UV-vis absorption spectra, (b) photoluminescence emission spectra ($\lambda_{exi}$ at 380 nm).

Figure 43:
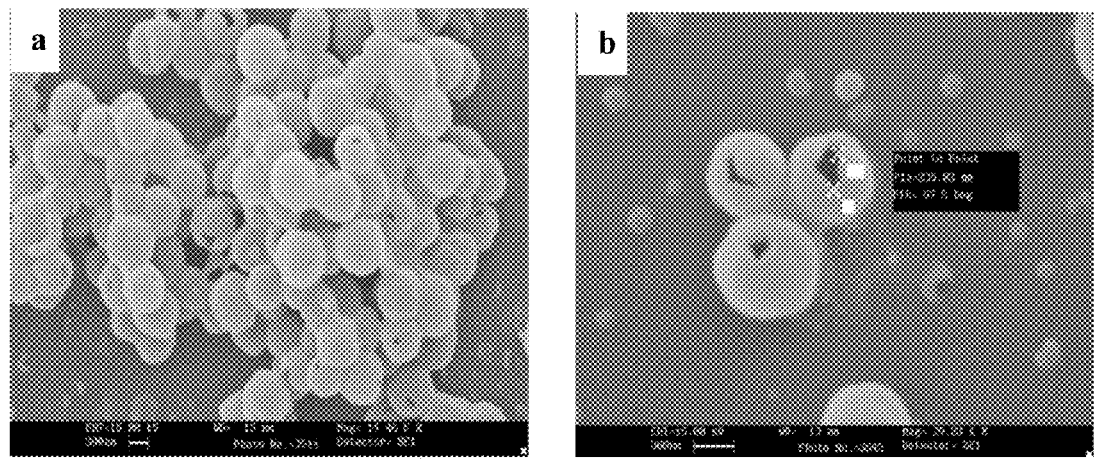

FIG. 43 shows Microscopic studies of NDI 5. (a) and (b) SEM micrograph of open mouth nanovesicles obtained from the solution of NDI 5 in MeOH/$CHCl_3$ (95:5) solvent system on glass substrate.

Figure 44:
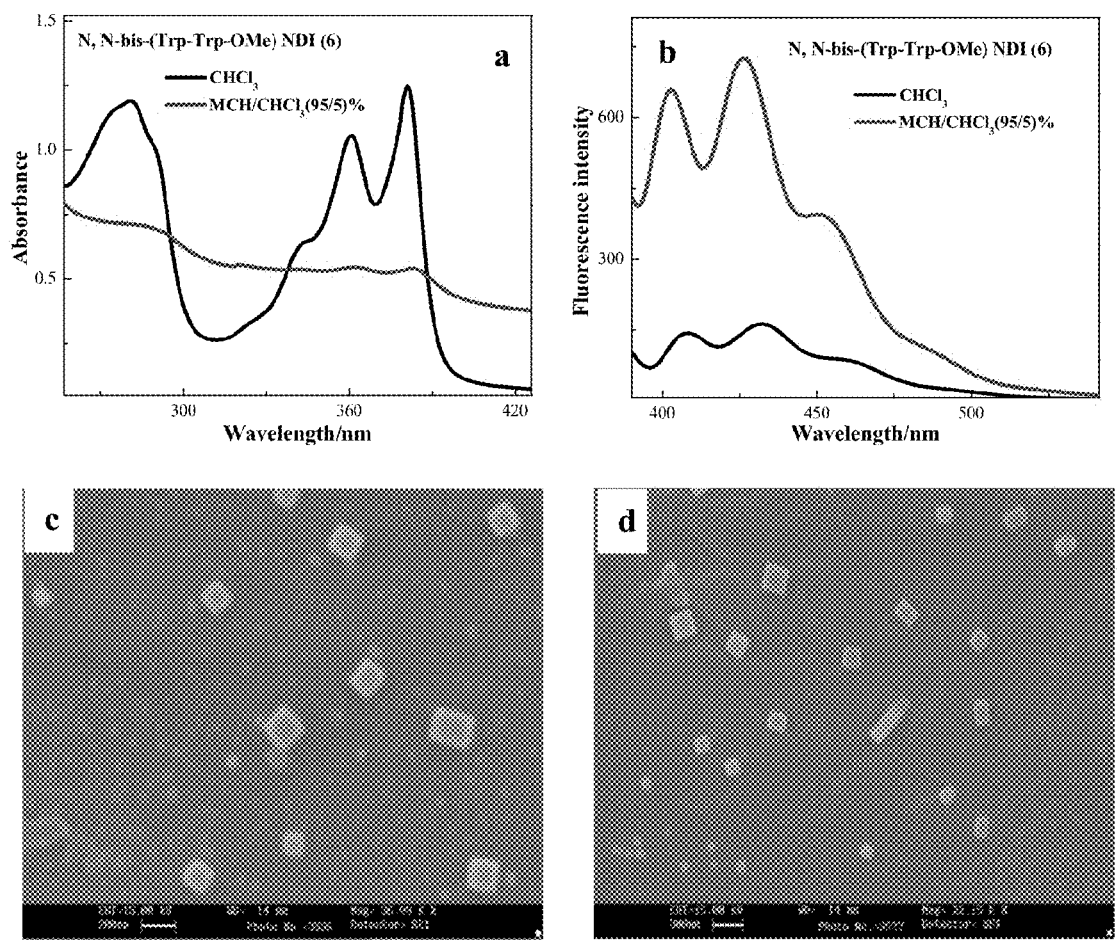

FIG. 44 shows Photophysical studies of NDI 6 ($5\times10^{-5}$ M) in $CHCl_3$ (black curve) and in MCH/$CHCl_3$ (95:5) (red curve). (a) UV-vis absorption spectra, (b) photoluminescence emission spectra ($\lambda_{exi}$ at 380 nm), (c) and (d) SEM micrograph of NDI 6 nanocubes obtained from the MCH/$CHCl_3$ (95:5) solution on glass substrate.

Figure 45:
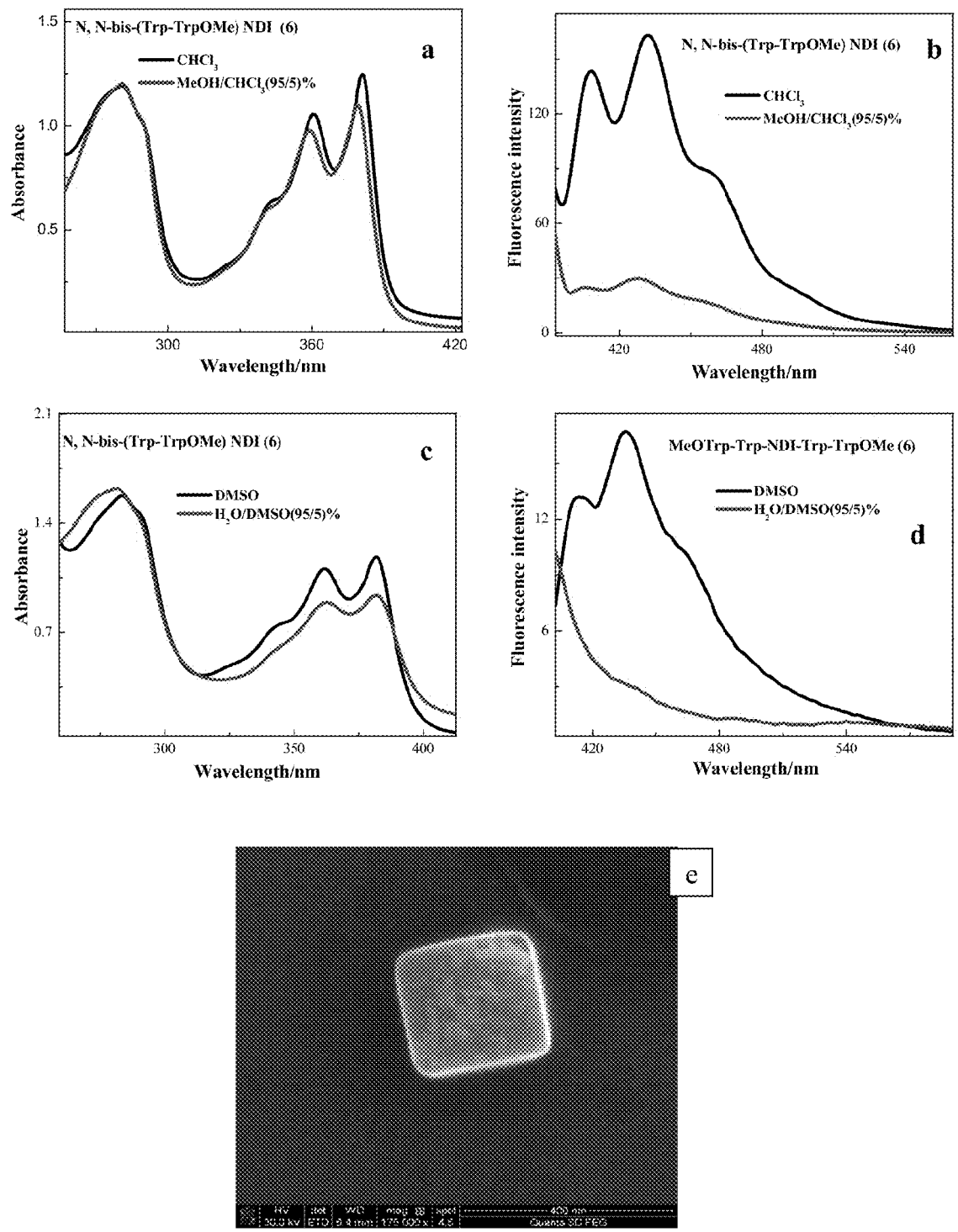

FIG. 45 shows Photophysical studies of NDI 6 ($5\times10^{-5}$ M), (a) and (c) UV-vis absorption spectra, (b) and (d) Photoluminescence emission spectra ($\lambda_{exi}$ at 380 nm), (e) FESEM micrograph of NDI 6 nanocubes obtained from the $H_2O$/DMSO (95:5) solvent system.

Figure 46:
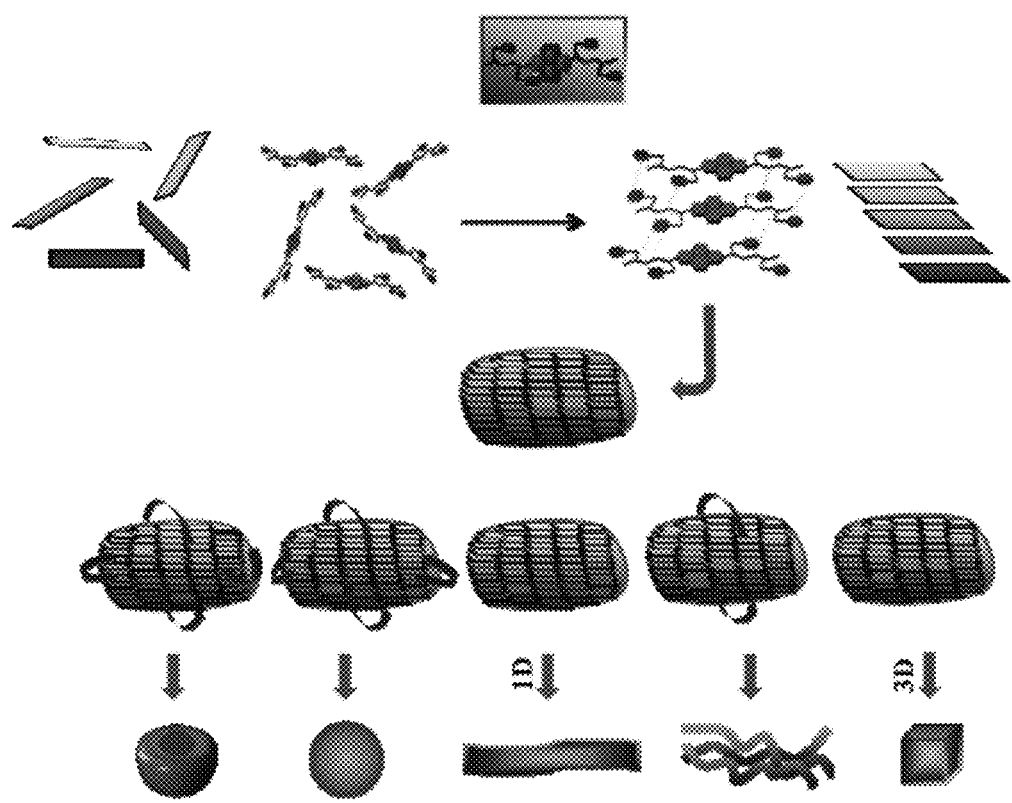

FIG. 46 shows Proposed schematic model to explain the self-assembly process of N,N-bis-(dipeptide) appended NDI systems 4, 5 and 6 into zero-, one-, two- and three-dimensional nanostructures (nanosphere, nanotape, open mouth nanovesicle and nanocube).

Figure 47:
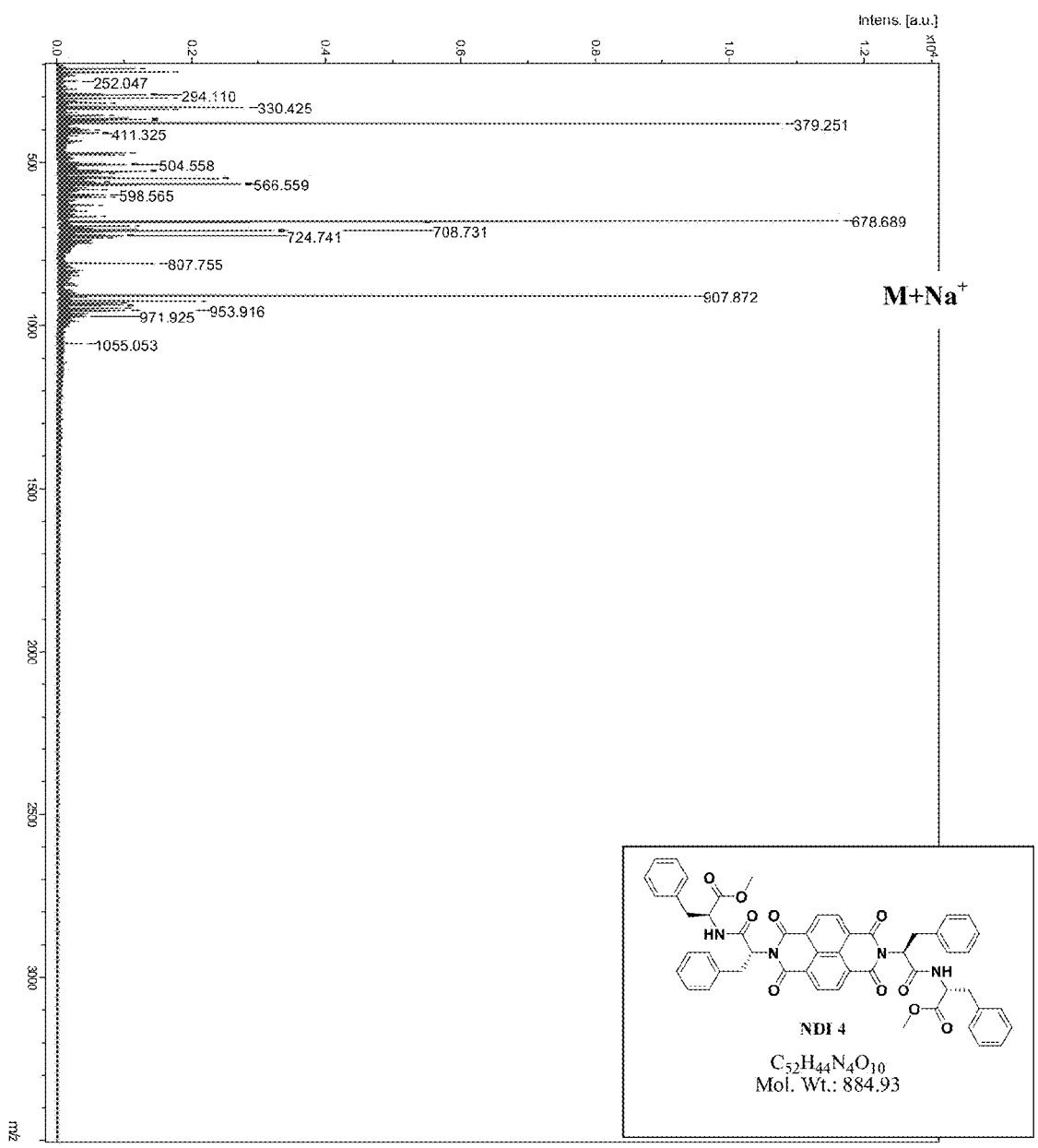
Figure 48:
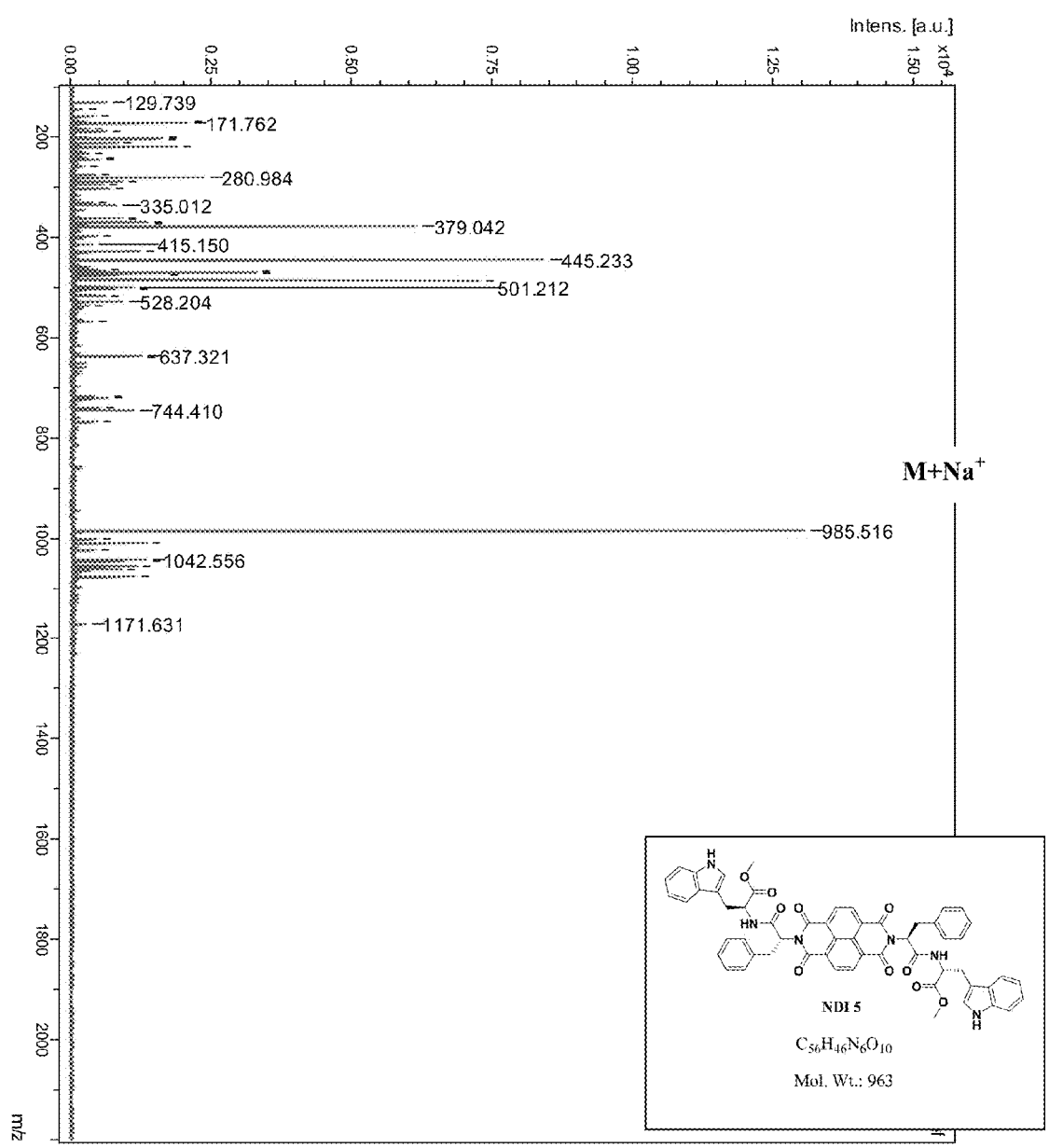
Figure 49:
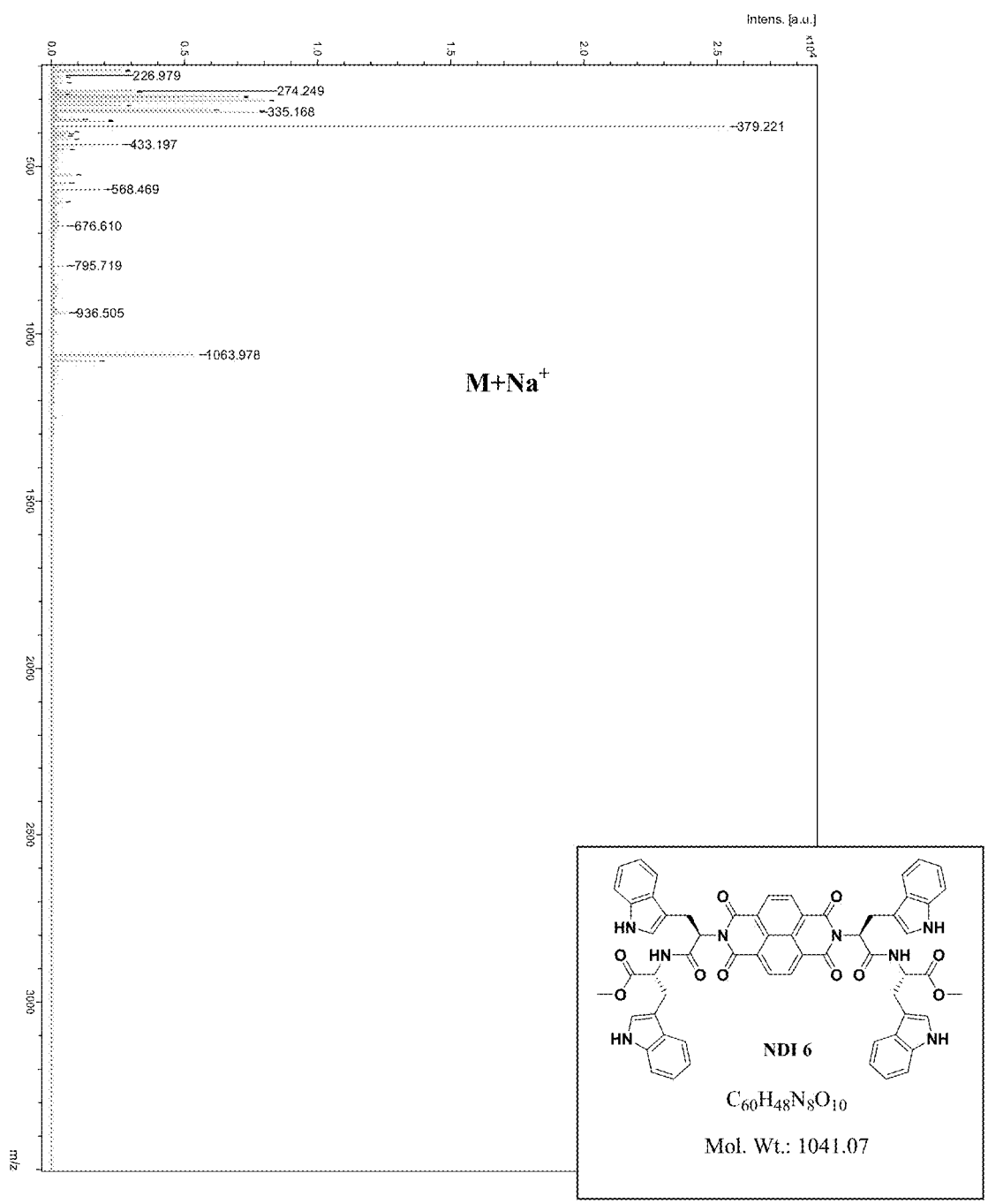

FIG. 47 shows MALDI-TOF of NDI 4.
FIG. 48 shows MALDI-TOF of NDI 5.
FIG. 49 shows MALDI-TOF of NDI 6.

Figure 50:
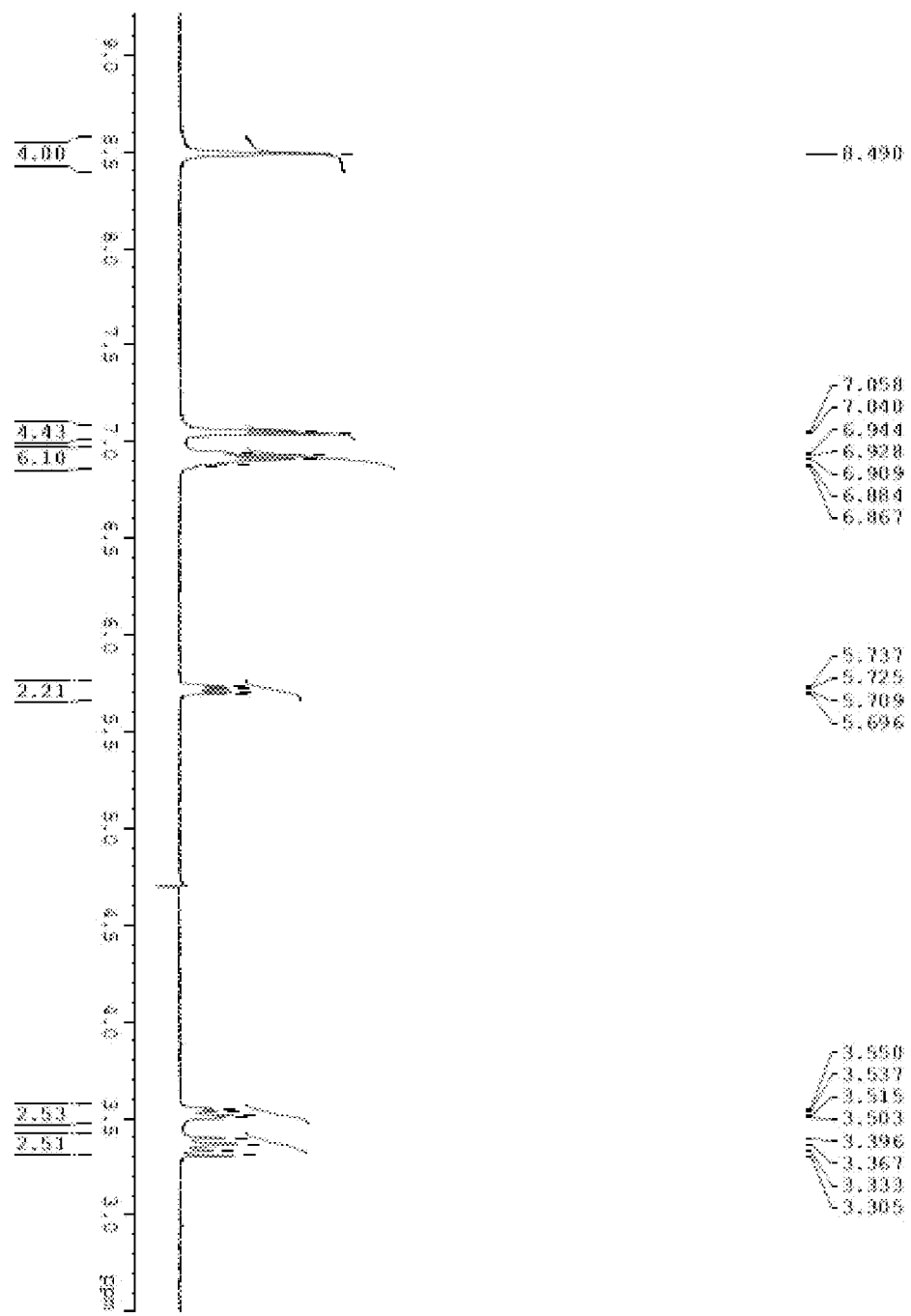
Figure 51:
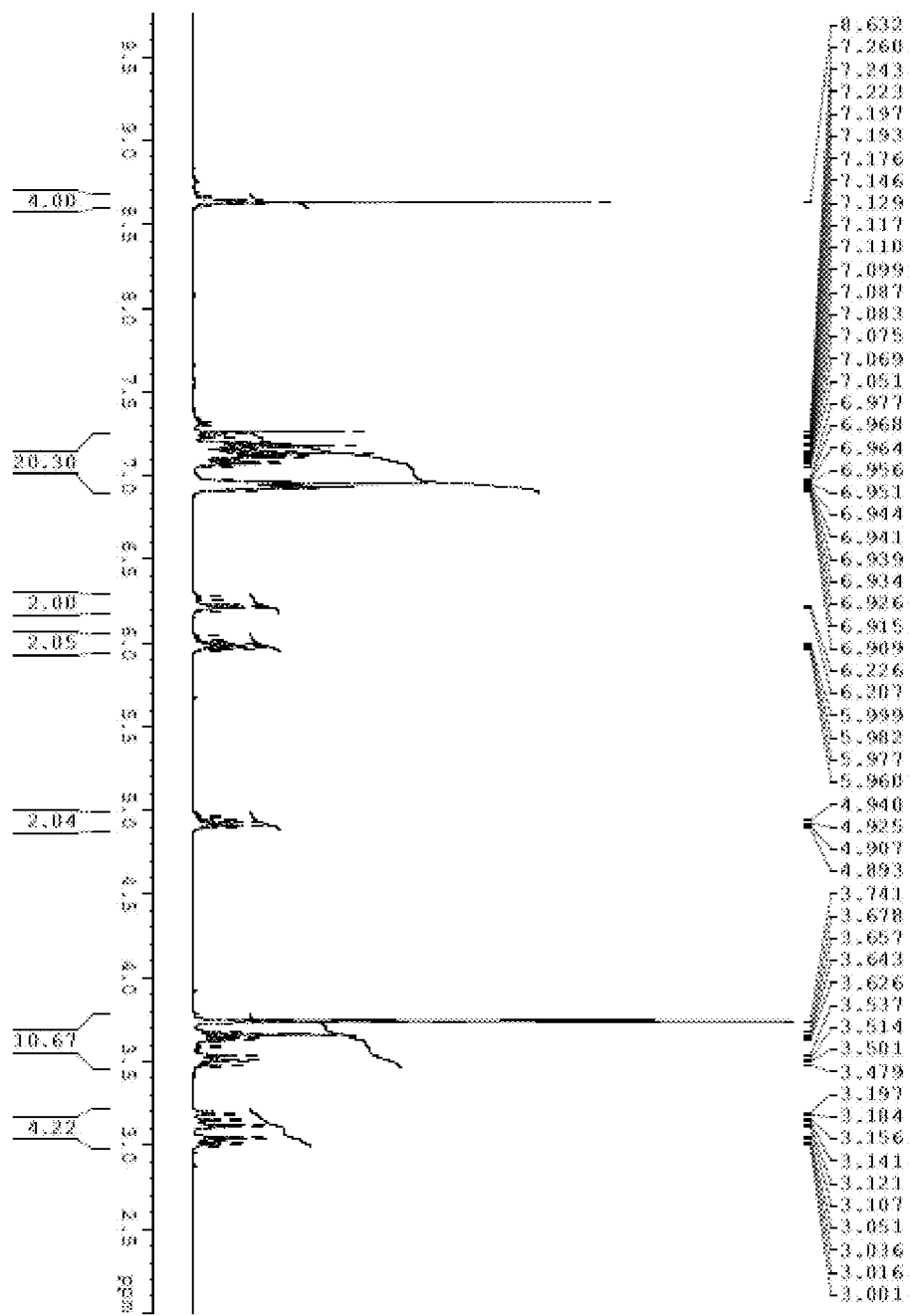
Figure 52:
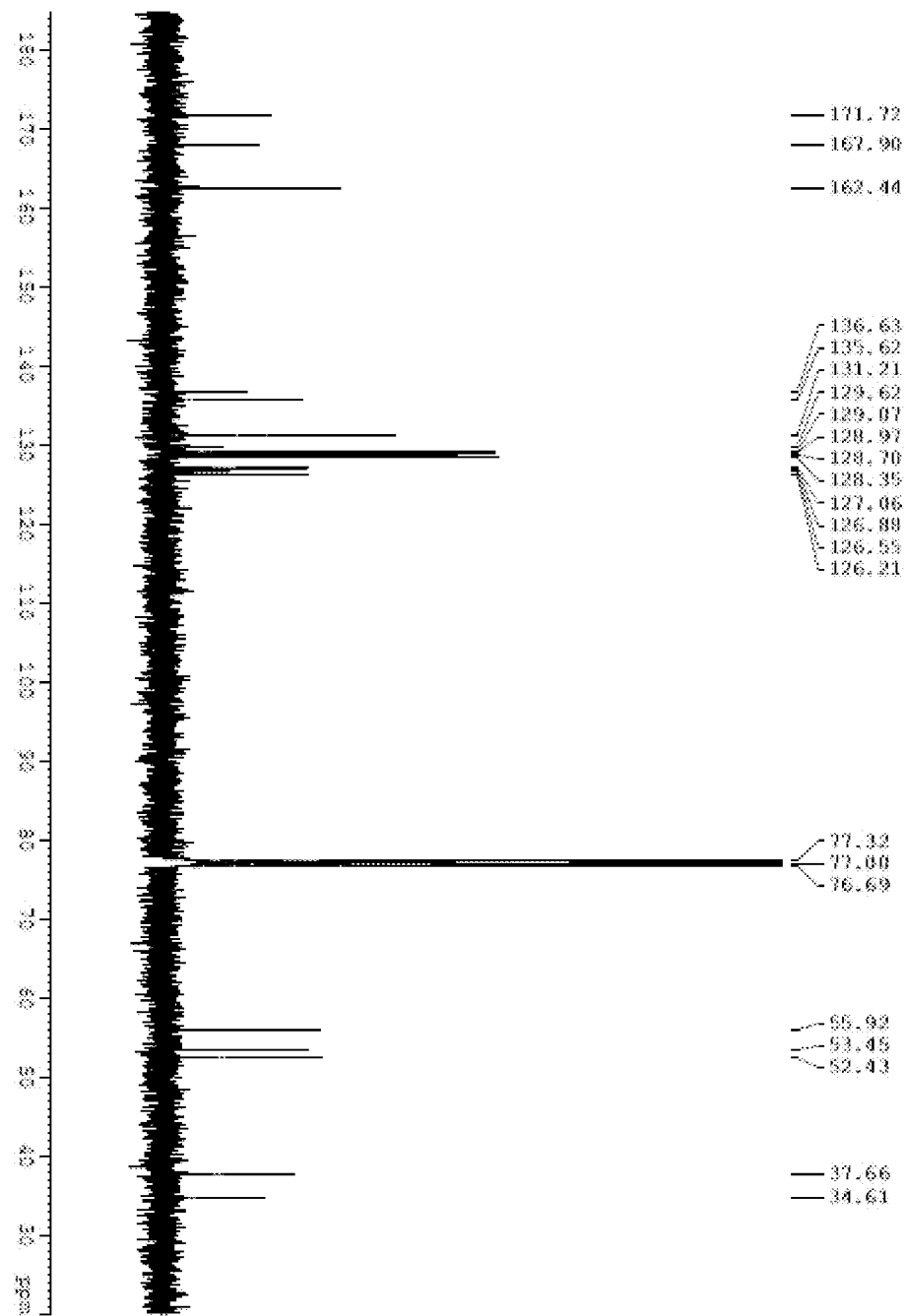
Figure 53:
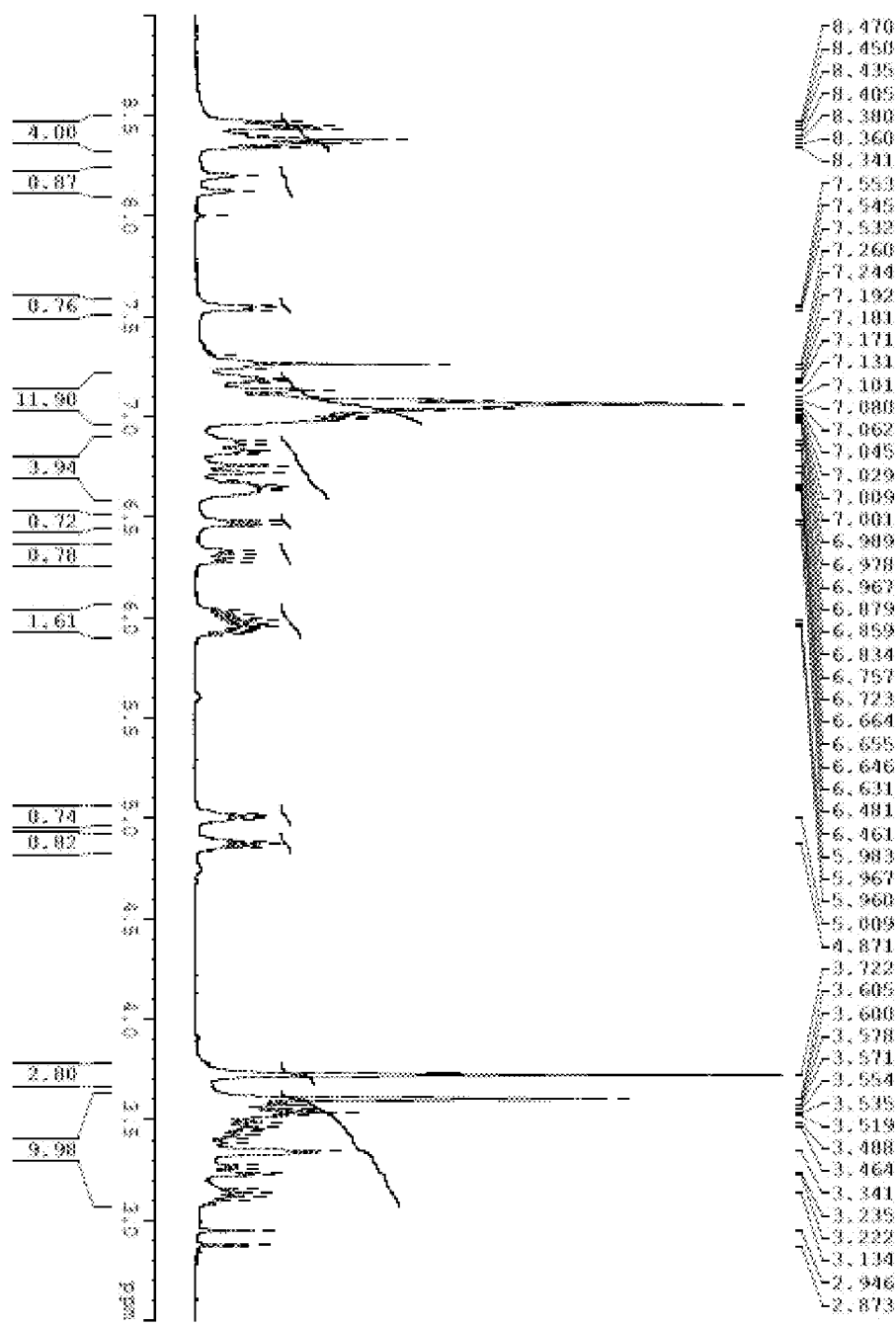
Figure 54:
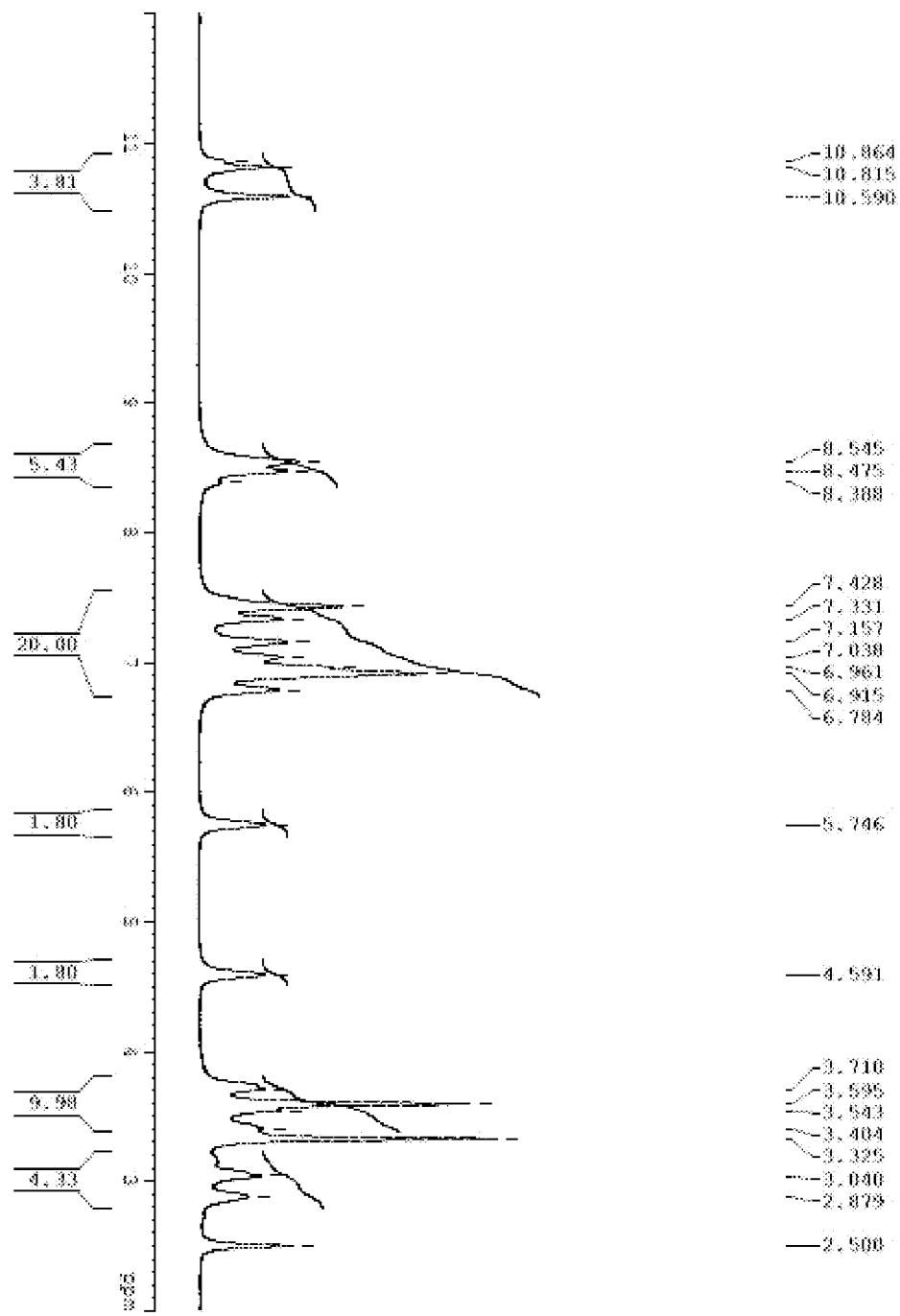
Figure 55:
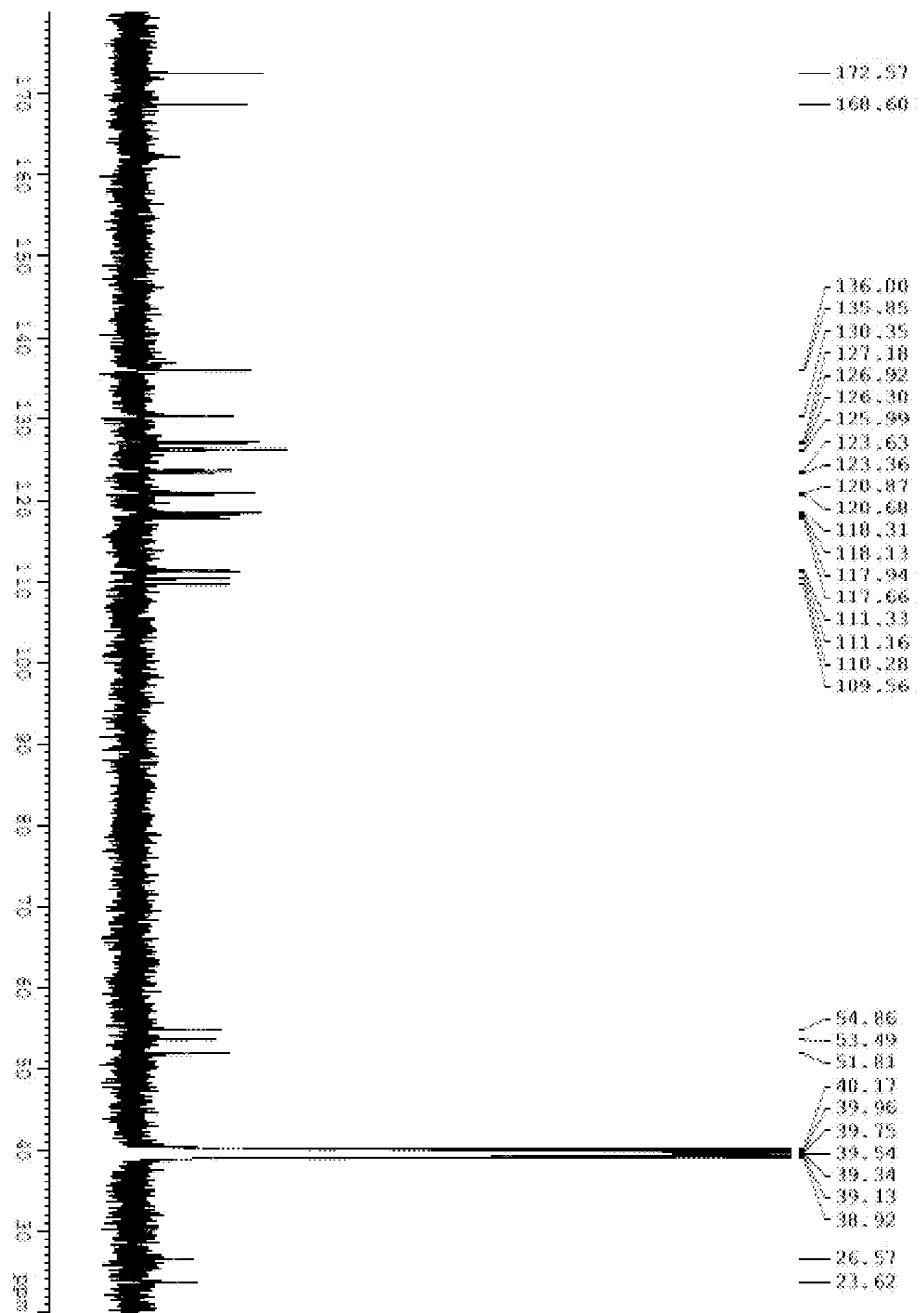
Figure 56:
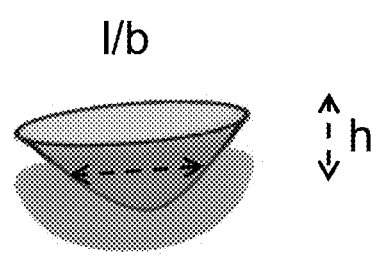

FIG. 50 shows $^1$H NMR ($CDCl_3$, 400 MHz) of NDI 1.
FIG. 51 shows $^1$H NMR ($CDCl_3$, 400 MHz) of NDI 4.
FIG. 52 shows $^{13}$C NMR ($CDCl_3$, 400 MHz) of NDI 4.
FIG. 53 shows $^1$H NMR ($CDCl_3$, 400 MHz) of NDI 5.
FIG. 54 shows $^1$H NMR (DMSO, 400 MHz) of NDI 6.
FIG. 55 shows $^{13}$C NMR (DMSO, 400 MHz) of NDI 6.
FIG. 56 shows Calculation of container inner volume illustrating ultra-small containers for performing miniaturized biological assays

DETAILED DESCRIPTION OF THE DISCLOSURE

The present disclosure relates to a method of self assembling naphthalene diimide derivative into nano, meso or micro structures, said method comprising acts of:
a) dissolving the naphthalene diimide derivative in a solvent to form a solution; and
b) adding co-solvent to the solution to obtain the self assembled nano, meso or microstructures.

In an embodiment of the present disclosure, the naphthalene diimide derivative is selected from a group comprising derivatives of amino acids, methyl esters of amino acids and peptide or any combination thereof.

In another embodiment of the present disclosure, the amino acid is selected from a group comprising phenylalanine and tryptophan.

In yet another embodiment of the present disclosure, the peptide is selected from a group comprising phenylalanine-phenylalanine, tryptophan-tryptophan and phenylalanine-tryptophan or any combination thereof.

In still another embodiment of the present disclosure, the solvent is selected from a group comprising acetonitrile, methanol, dimethylsulfoxide and dimethylformamide.

In still another embodiment of the present disclosure, the co-solvent is selected from a group comprising water, chloroform, dichloromethane, carbon tetrachloride and sodium hydroxide or any combination thereof.

In still another embodiment of the present disclosure, the method is carried out at temperature ranging from about 0° C. to about 100° C., preferably from about 20° C. to about 30° C.

The present disclosure also relates to a self assembled nano, meso or micro structure of naphthalene diimide derivative.

In an embodiment of the present disclosure, the nanostructure is selected from a group comprising nanospheres, nanobelts, nanofibres, nanosheets, nanotapes, nanoparticles, nanofractals, nanocubes, nanovesicles and nanocups.

In another embodiment of the present disclosure, the mesostructure is selected from a group comprising mesocups and mesobowls or any combination thereof.

In yet another embodiment of the present disclosure, the microstructure is selected from a group comprising microfibers and microbowls, preferably microfibers.

In still another embodiment of the present disclosure, length of the nanosheet ranges from about 2 nm to about 500 μm and breadth of the nanosheet ranges from about 2 nm to about 500 μm.

In still another embodiment of the present disclosure, height of the nanocup ranges from about 40 nm to about 80 nm and internal diameter ranges from about 400 nm to about 500 nm.

In still another embodiment of the present disclosure, lateral width of the mesocup ranges from about 200 nm to about 900 nm.

In still another embodiment of the present disclosure, the microfibers have diameter ranging from about 0.5 µm to about 5 µm.

The present disclosure also relates to a method of using self assembled structure of naphthalene diimide derivative as an electronic component, said method comprising act of associating the self assembled structure in an electronic device.

The present disclosure also relates to a method of using self assembled structure of naphthalene diimide derivative as a biomaterial, said method comprising act of associating the self assembled structure to a subject in need thereof.

In an embodiment of the present disclosure, the subject is an animal including human being.

In the present disclosure the synthesis and characterization of aromatic conjugated NDIs are presented. This disclosure demonstrates the use of small peptide sequences with π system directly embedded in the backbone to promote assembly of NDI into well ordered nano architectures with strong π-π intermolecular electronic communication in the mixture of polar/non polar solvents.

In an embodiment of the disclosure, molecular interactions and their organizations are the basis for various biological and non biological systems. The molecular recognition process is complicated as it is influenced by several factors. Nature provides an exhaustive illustration of the elegance with which the noncovalent interactions have been employed in the design strategy catering various requirements. To mimic nature's versatility in controlling molecular interactions supramolecular design principles are employed. Despite significant advances in supramolecular chemistry, direct control of molecular organization remains a daunting task. Though there is evolution in tuning the selectivity and specificity of the weak, complicated molecular interactions, it is still in its infancy. Noncovalent assembly of aromatic moieties with variable functionality into well defined architectures remains a challenging task for chemists. The main challenge in organizing aromatic moieties lies in controlling and optimizing the relatively strong π-π interactions in cooperation with those of the substituents. The most commonly employed strategy to functionalize arylene diimide is by a long chain alkyl, alkoxy or the phenyl substituent. The solubility is crucial for the solution processing of individual molecules which requires appropriate side chain modification. Substitution with long or branched alkyl groups can aid solubility in organic nonpolar solvents while their hydrophobic effect in polar solvents can facilitate aromatic stacking. Generally linear alkyl chains lead to 1D architectures while the branched chain to 0D agglomerates. Increasing the size of the aromatic core can aid in molecular packing. However the planarity and their solubility can be affected. The solvent-molecule interactions are yet another factor affecting the morphology of molecular self-assembly. Moreover the rate of aggregation can vary from spontaneous to controlled process depending on the alkyl chain length. Contrary to alkyl chains, alkoxy imide substituents (bolaamphiphiles) being hydrophilic renders solubility in polar solvents and can be assembled in nonpolar solvents. Amphiphiles with alkyl and alkoxy imide substituents on either side are also employed in the molecular design. The phenyl substituent offers rigidity and additional aromatic interactions. All these substituent's are rather restricted to a simple, specific interaction such as hydrophobic, hydrophilic or aromatic and lack a combination of non-covalent forces that can act in a cooperative manner. The instant disclosure deals with the tuning of naphthalene diimide architectures through amino acids and peptides. The method used is highly useful for solution processing of n-type organic semi-conductors. The method disclosed uses a strategy to balance non-covalent interactions to tune the nano structures. The method delivers easily processible semiconductor materials that can also be used as biomaterials.

In an embodiment of the disclosure, amino acids are the important structural and signaling biomolecules due to their molecular recognition and distinctive sequence-specific self-assembly properties.

Figure 2:
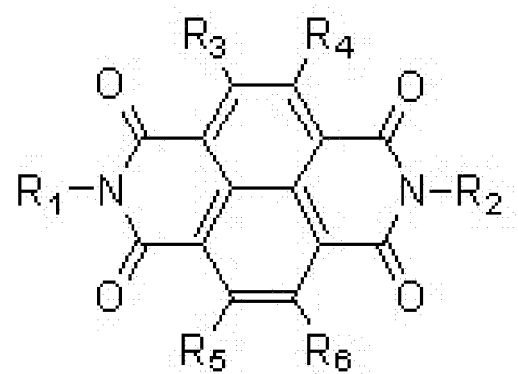

In an embodiment of the disclosure, the molecular organization of NDI appended with two tryptophan moieties (FIG. 2) and NDI appended with phenylalanine moiety (FIG. 14a) is described. The choice of tryptophan as imide substituent is unique due to its polar carboxylic acid group and an indole aromatic heterocycle offering both the hydrophilic and hydrophobic properties in a single moiety. In addition, tryptophan provides coordination sites for metal binding, flexibility to functionalization and biocompatibility. The disclosure demonstrates the probable ways in which these properties can be exploited. Di-tryptophan appended NDI has excellent solubility in polar solvents. A small structural modification such as methyl ester of tryptophan appended to NDI renders better solubility in nonpolar solvents. Hydrophobic effect induces J-type aggregation in the tryptophan appended NDIs. The present disclosure also shows that NDIs are self-assembled as H-type aggregates via sodium coordination which involves sodium cation-π interactions. All these features bring about drastic changes in the morphology of NDIs by transforming into well defined architectures. NDIs self-assemble to form nanospheres. The molecular organization can be transformed from nanospheres to particles, nanobelts, fibers and fractals. Fractals have been exemplified with broad range of applications due to their multiple length scales. The molecular interaction induced organizations of NDIs into materials with well defined architectures have been thoroughly characterized by photophysical, spectroscopic and morphological studies. Strikingly, such drastic change in the morphology of NDIs architectures is a clear evidence of the importance of these weak, complicated noncovalent forces.

In an embodiment of the disclosure, the objective of the present disclosure is to synthesize and study the supramolecular assembly of a series of N,N-dipeptide appended naphthalenetetracarboxylicaciddiimide (NDI) chromophores. The aromatic functionalities of amino acids side chain was systematically varied to understand the effect of this simple structural variations on the self-assembly. The properties of resulting self-assembled nanomaterials and their architectures were studied using various spectroscopic and microscopic techniques.

Design Strategy—

For the fabrication of self-assembled nanostructure with well defined order an appropriate balance of solvophobic, hydrogen bonding, π-π stacking and steric interactions is required. Hence, the N,N-bis-(dipeptide) appended NDI molecule is designed as shown in FIG. 35. A small peptide sequence with π-conjugated NDI directly embedded in the backbone promote molecular self-assembly into various nanostructures with strong π-π intermolecular interactions and hydrogen bonding. The planar NDI and aromatic side chain on dipeptides ($R_1$ and $R_2$ in FIG. 33) will induce π-π stacking and amide groups will induce highly directional hydrogen bonding between the molecules.

As a result of these combined non-covalent interactions and appropriate solvent conditions the N,N-bis-(dipeptide) appended NDI molecule is expected to self-assemble into nanostructures with well defined architectures.

In the present disclosure, the NDIs 4, 5 and 6 have been synthesized by appending aromatic dipeptides (Phe-Phe, Phe-Trp and Trp-Trp) to NDA (1,4,5,8-Naphthalenetetracarboxylic dianhydride) as shown in FIG. 33. Aromatic dipeptide modified NDIs 4, 5 and 6 self-assemble into well ordered architectures through intermolecular hydrogen bonding and aromatic π-π stacking in an appropriate environment. FIG. 34 shows the schematic representation of self-assembly of NDIs 4, 5 and 6 from randomly oriented molecules to ordered assemblies with the help of proposed amide hydrogen bonding and π-π interactions between the amide groups and planar π conjugated NDI and aromatic side chains on dipeptide moieties respectively.

Methods Used for Analysis—

NMR and Mass Spectra: $^1$H and $^{13}$C NMR are measured on a Bruker AV-400 spectrometer with chemical shifts reported as ppm (in $CDCl_3/CD_3CN/DMSO-d_6$, Tetramethylsilane as internal standard). Mass spectra are obtained from Shimadzu 2020 LC-MS.

Absorption Spectroscopy: UV-vis spectra are recorded on a Perkin Elmer Model Lambda 900 spectrophotometer. 100 μM of the sample is analyzed in quartz cuvette of 1 mm path length.

Fluorescence Spectroscopy: Fluorescence spectra are recorded on a Perkin Elmer Model LS 55 spectrophotometer. 100 μM of the sample is analyzed in quartz cuvette of 1 mm path length with an excitation at 375 nm.

Circular Dichroism (CD): CD measurements are carried out on a Jasco J-810 spectropolarimeter under nitrogen atmosphere. 100 μM/1 mM of the sample is analyzed in quartz cuvette of 1 mm path length.

Infrared (IR) Spectroscopy: IR spectra are recorded on a Bruker IFS 66/V spectrometer on a sodium chloride crystal. The liquid sample (free floating sheets in case of 90% aqueous acetonitrile) is drop casted and is allowed to dry naturally on the sodium chloride crystal.

Field Emission Scanning Electron Microscopy (FESEM): FESEM micrographs are acquired by using FEI Nova nanoSEM-600 equipped with a field emission gun operating at 15 kV. The sample was prepared by drop casting either on a Al stub or on a Si(111) substrate.

High Resolution Transmission Electron Microscopy (HR-TEM): HRTEM measurements are performed on a JEOL, JEM 3010 instrument operated at 300 kV. The samples are prepared by drop casting on a 200 mesh holey carbon supported copper grids.

Atomic Force Microscopy (AFM): AFM micrographs are acquired under ambient conditions using Innova (Veeco) atomic force microscope in dynamic force (tapping) mode. The samples are prepared by drop casting on freshly cleaved mica or Si(111). AFM section analysis is done offline.

Current Sensing (Conductive) Atomic Force Microscopy (C-AFM): C-AFM are also performed using the above mentioned Innova (Veeco) atomic force microscope. Pt/Ir coated Si tips with a tip radius (Max) of 25 nm (Bruker; Model: SCM-PIC) are employed. The samples are prepared by drop casting on freshly cleaved highly oriented pyrolytic graphite (HOPG). Current-Voltage (1-V) characteristics are obtained from several points on the self assembled nanosheets of different topographical thickness (height). The value of the conductivity (σ) is calculated from the equation [σ=d/(AR) $Scm^{-1}$]. Where d is the sheet thickness/height (10-100 nm), A is the area of the C-AFM probe in contact with the surface and computed as $πr^2$, assuming a contact radius of 25 nm between tip and sample. R is the resistance of the sample, calculated from the inverse slope of the I-V curve.

X-ray Single crystal Measurement: X-ray single crystal structural data is collected by a Bruker Smart-CCD diffractometer equipped with a normal focus, 2.4 kW sealed tube X-ray source (Mo Kα radiation, 0.71073 Å), operating at 50 kV and 30 mA. An empirical absorption correction based on symmetry equivalent reflections is applied using the SAD-ABS program.

Powder X-Ray Diffraction (PXRD): PXRD patterns is recorded with a Rigaku-99 (Miniflex) diffractometer using Cu Kα radiation (λ=1.5406 Å). The free floating self-assembled L-NDI nanosheets are drop casted on a glass slide.

Femtojet Technique: The fluorescent dyes are injected by using Injectman NI2 coupled to Femtojet (Eppendorf) setup. The dyes are injected by means of Femtotips with an injection pressure (Pi) of 15/25/50/200 hPa, injection time (Ti) of 0.2 sec and compensation pressure (Pc) of 0 hPa. 1 μM solution of rhodamine B base and fluorescein free acid in 10:90 (v/v) $CHCl_3$: MeOH is employed.

Fluorescence Confocal Microscopy: Confocal micrographs are obtained from LSM 510 META-Carl Zeiss. Two-photon laser is employed to excite the self assembled L/D-NDI nanosheets. An excitation wavelength of 543 nm and 488 nm is used to excite rhodamine B base and fluorescein dyes respectively. LSM image examiner is utilized for processing the images.

The present disclosure is further elaborated by the following examples and figures. However, these examples should not be construed to limit the scope of the disclosure.

EXAMPLE 1

Synthesis of Tryptophan Appended Naphthalene Tetra Carboxylicdiimide (NDI 1)

A modified procedure of Sanders and coworkers has been employed to synthesize NDI 1. 1,4,5,8-Naphthalenetetracarboxylic dianhydride (200 mg, 0.746 mmol) and L-tryptophan (305 mg, 1.491 mmol) are suspended in DMF (20 mL) in a 250 mL Erlenmeyer flask. To this suspension is added 0.2 mL of triethylamine. The suspension is sonicated until the mixture became homogeneous. The reaction mixture is heated under microwave irradiation at full power for 3 min. in steps of 30 sec. and with 30 sec interval. The resulting dark brown oil is taken up into methanol (400 mL). The solution is added under stirring to 600 mL of 1N HCl. The resulting suspension is allowed to coagulate overnight and then filtered through a sintered glass funnel. The solid is then washed with 200 mL deionized water and dried in vacuo to obtain a brown solid of NDI 1. Yield 90%. $^1$H NMR: (400 MHz, DMSO-$d_6$) $δ_{ppm}$ 3.46-3.52, (dd, 2H, $CH_2$, J=8 Hz, 8 Hz); 3.65-3.71 (dd, 2H, $CH_2$, J=8 Hz, 8 Hz); 5.84-5.87 (dd, 2H, αCH, J=4 Hz, 4 Hz); 6.78-6.82 (m, 2H, ArH); 6.92-6.96 (m, 2H, ArH); 7.04-7.05 (d, 2H, ArH, J=4 Hz); 7.19-7.21 (d, 2H, ArH, J=8 Hz); 7.46-7.48 (d, 2H, ArH, J=8 Hz); 8.61 (s, 4H, ArH); 10.64-10.65 (d, 2H, COOH, J=4 Hz); 12.99 (br, 2H, NH). $^{13}$C NMR: (400 MHz, DMSO-$d_6$) $δ_{ppm}$ 24.0, 54.2, 110.1, 111.2, 117.9, 118.2, 120.7, 123.6, 125.7, 125.9, 127.0, 131.1, 135.9, 162.0, 170.4. MS (EI): m/z=641.16[M+H]$^+$ for $C_{36}H_{24}N_4O_3$. Elemental analysis: Found: C, 67.35; H, 3.88; N, 8.72; Calcd: C, 67.39; H, 3.84; N, 8.75 for $C_{36}H_{24}N_4O_8$.

EXAMPLE 2

Synthesis of Tryptophan Methyl Ester Appended Naphthalenetetracarboxylicdiimide (NDI 2)

Synthesis of L-Tryptophan methyl ester hydrochloride: Anhydrous methanol (50 mL) is taken in a 100 mL 2-necked round bottom flask fitted with a reflux condenser and an additional dropping funnel and cooled to ice temperature. Acetylchloride (3 mL) is added drop wise through the dropping funnel. After 15 min, L-tryptophan (3 g) is added and the reaction mixture is refluxed at 70° C. for 6 h. The reaction mixture is vacuo dried to obtain L-tryptophan methyl ester hydrochloride in quantitative yield and used for further reaction without purification. 1,4,5,8-Naphthalenetetracarboxylic dianhydride (200 mg, 0.746 mmol) and L-tryptophan methyl ester hydrochloride (380 mg 1.491 mmol) are suspended in 20 mL of DMF in a 100 mL round bottom flask. To this suspension is added 0.5 mL of triethylamine under inert atmosphere. The reaction mixture is refluxed at 65° C. for 21 h. Solvent is evaporated under vacuo and the residue is purified by column chromatography (15% methanol in chloroform) to obtain NDI 2 in good yield. Yield 86%. $^1$H NMR: (400 MHz, CDCl$_3$-CF$_3$COOH) $\delta_{ppm}$ 3.64-3.70, (dd, 2H, CH$_2$, J=8 Hz, 8 Hz); 3.78-3.84, (dd, 2H, CH$_2$, J=8 Hz, 8 Hz); 3.90 (s, 6H, CH$_3$); 6.12-6.16 (dd, 2H, αCH, J=8 Hz, 4 Hz); 6.86-7.02 (m, 6H, ArH); 7.13-7.15 (d, 2H, ArH, J=8 Hz); 7.46-7.48 (d, 2H, ArH, J=8 Hz); 8.57 (s, 4H, ArH). $^{13}$C NMR: (400 MHz, CDCl$_3$-CF$_3$COOH) $\delta_{ppm}$ 24.5, 53.9, 55.1, 110.2, 110.4, 118.6, 119.8, 122.4, 123.2, 126.1, 126.6, 127.2, 131.8, 136.1, 163.0, 172.5. MS (EI): m/z=668.19[M]+ for C$_{33}$H$_{23}$N$_4$O$_3$. Elemental analysis: Found: C, 68.23; H, 4.25; N, 8.35; Calcd: C, 68.26; H, 4.22; N, 8.38 for C$_{33}$H$_{23}$N$_4$O$_3$.

EXAMPLE 3

Synthesis of L-Phenylalanine Methylester Appended Naphthalenediimide (L-NDI or NDI 3A): Synthesis of L-Phenylalanine Methylester Hydrochloride Anhydrous methanol (50 mL) is taken in a 100 mL 2-necked round bottom flask fitted with a reflux condenser and an additional dropping funnel and cooled to ice temperature. Acetyl chloride (3 mL) is added drop wise through the dropping funnel. After 15 min, L-phenylalanine (3 g, 18.16 mmol) is added and the reaction mixture is refluxed at 70° C. for overnight. The reaction mixture is vacuo dried to obtain L-phenylalanine methylester hydrochloride in quantitative yield and used for further reaction without purification.

1,4,5,8-naphthalenetetracarboxylic dianhydride (200 mg, 0.74 mmol) and L-phenylalanine methylester hydrochloride (322 mg 1.49 mmol) are suspended in DMF (20 mL) in a 100 mL round bottom flask. To this suspension triethylamine (0.6 mL) is added under inert atmosphere. The reaction mixture is refluxed at 75° C. for 24 h. Solvent is evaporated under vacuo and the residue is purified by column chromatography (1% methanol in chloroform). Yield 74%. $^1$H NMR (400 MHz, CDCl$_3$): δ 8.63 (s, 4H), 7.1 (m, 10H), 6.02 (dd, 2H, J=8 Hz, 4 Hz), 3.77 (s, 6H), 3.73 (dd, 2H, J=8 Hz, 4 Hz), 3.50 (dd, 2H, J=12 Hz, 4 Hz). $^{13}$C NMR (400 MHz, CDCl$_3$) δ 169.6, 162.4, 136.9, 131.3, 129.2, 128.5, 126.9, 126.8, 126.3, 54.8, 52.8, 34.9. MS (EI): m/z=590.16[M]$^+$ for C$_{34}$H$_{26}$N$_2$O$_8$. Elemental analysis: Found: C, 69.12; H, 4.48; N, 4.69; Calcd: C, 69.15; H, 4.44; N, 4.74 for C$_{34}$H$_{26}$N$_2$O$_8$.

EXAMPLE 4

Synthesis of D-Phenylalanine Methylester Appended Naphthalenediimide (D-NDI or NDI 3B): Synthesis of D-Phenylalanine Methylester Hydrochloride Anhydrous methanol (50 mL) is taken in a 100 mL 2-necked round bottom flask fitted with a reflux condenser and an additional dropping funnel and cooled to ice temperature. Acetyl chloride (3 mL) is added drop wise through the dropping funnel. After 15 min, D-phenylalanine (3 g, 18.16 mmol) is added and the reaction mixture is refluxed at 70° C. for overnight. The reaction mixture is vacuo dried to obtain D-phenylalanine methylester hydrochloride in quantitative yield and used for further reaction without purification.

1,4,5,8-naphthalenetetracarboxylic dianhydride (200 mg, 0.74 mmol) and D-phenylalanine methylester hydrochloride (322 mg 1.49 mmol) is suspended in DMF (20 mL) in a 100 mL round bottom flask. To this suspension triethylamine (0.6 mL) is added under inert atmosphere. The reaction mixture is refluxed at 75° C. for 24 h. Solvent is evaporated under vacuo and the residue is purified by column chromatography (1% methanol in chloroform). Yield 71%. $^1$H NMR (400 MHz, CDCl$_3$): δ 8.63 (s, 4H), 7.1 (m, 10H), 6.02 (dd, 2H, J=4 Hz, 4 Hz), 3.77 (s, 6H), 3.73 (dd, 2H, J=8 Hz, 4 Hz), 3.50 (dd, 2H, J=12 Hz, 4 Hz). $^{13}$C NMR (400 MHz, CDCl$_3$) δ 169.6, 162.4, 136.9, 131.3, 129.2, 128.5, 126.9, 126.8, 126.4, 54.9, 52.8, 34.9. MS (EI): m/z=590.17[M]$^+$ for C$_{34}$H$_{26}$N$_2$O$_8$. Elemental analysis: Found: C, 69.10; H, 4.49; N, 4.78; Calcd: C, 69.15; H, 4.44; N, 4.74 for C$_{34}$H$_{26}$N$_2$O$_8$.

EXAMPLE 5

J-Type Aggregation: Hydrophobic Effect

Figure 1A:
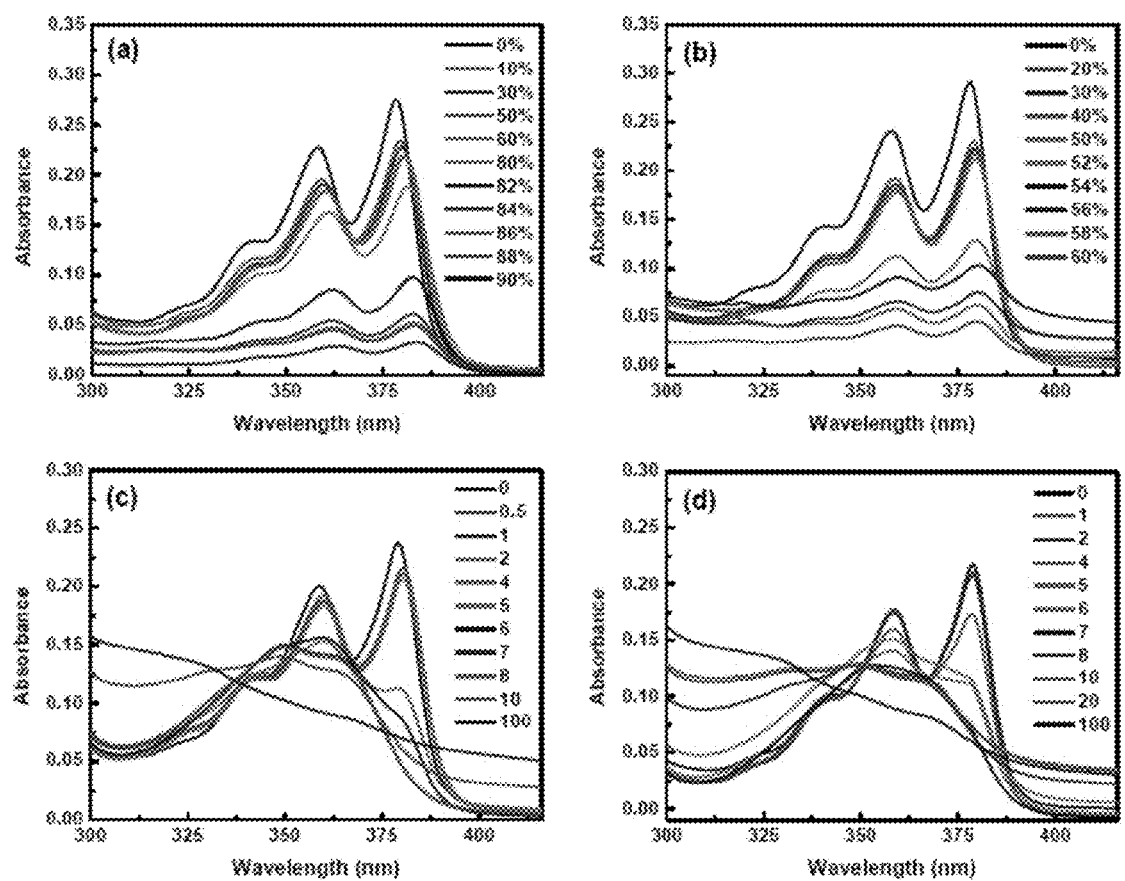
Figure 1B:
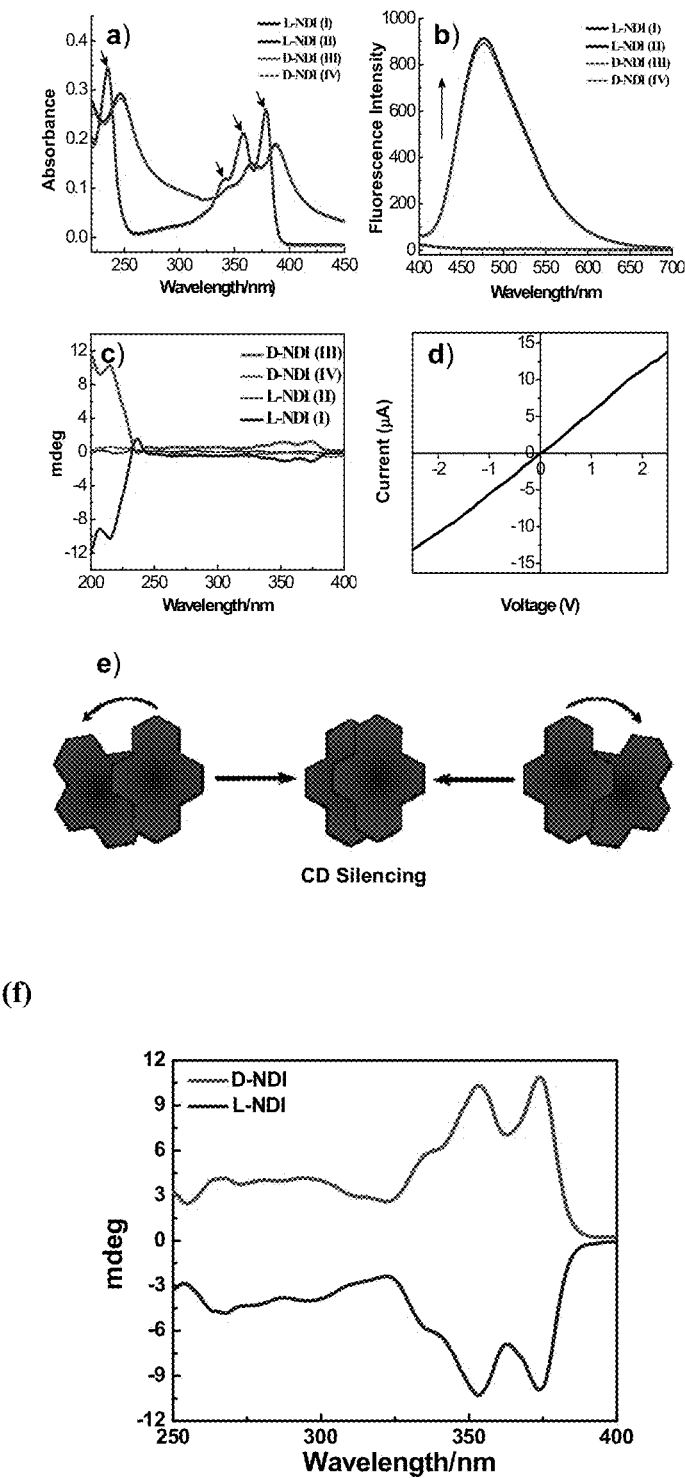

A typical UV-vis absorption spectra of NDI 1 (A modified procedure of Sanders and coworkers has been employed to synthesize NDI 1) in acetonitrile (100 µM) shows absorption bands at 340 nm, 358 nm and 378 nm due to characteristic ππ* transitions (FIG. 1a). On increasing the solvent polarity by means of water which has the highest solvophobic effect induces the stacking interactions between the aromatic molecules. Water molecules solvating the aromatic surface have a higher energy than bulk water. The aromatic stacking reduces the total surface exposed to the solvent. The bathochromic shift of the absorption band with solvent polarity indicates the J-type aggregation of NDI 1. A bathochromic shift of 2 nm, 4 nm and 6 nm for the 340 nm, 358 nm and 378 nm absorption bands are observed respectively. The absorption spectrum of NDI 2 in acetonitrile also possesses absorption bands at the same wavelength as it is unaffected by methyl ester substitution (FIG. 1b). The hydrophobic effect on NDI 2 in terms of bathochromicity is found to be minimal as can be seen from the absorption spectra. A bathochromic shift of 1 nm and 2 nm for 358 nm and 378 nm bands respectively is observed while 340 nm band is unaffected. Aromatic interactions are intriguing molecular recognition elements because they are expected to be strong in water due to their hydrophobic interactions. At the same time the aromatic interactions should be selective if the electrostatic component is significant. The aqueous medium provides the features of both hydrophobic and hydrogen bonding interactions.

UV-vis spectrum of L or D-NDI (100 µM) in acetonitrile exhibit strong absorption bands namely band I in the range of 300-400 nm and band II at 235 nm (FIG. 2a). The band I and band II is attributed to characteristic ππ* transition of NDI chromophores polarized along the z and y axis respectively. In 90% aqueous acetonitrile L or D-NDI undergo bathochromic shifts of 8 nm (band I) and 11 nm (band II) due to their π-π stacking. A decrease in absorption intensities and the observed band broadening indicate the presence of well defined aggregates. However L or D-NDI is weakly fluorescent in acetonitrile and in 90% aqueous acetonitrile L or D-NDI showed strong emission band centered at 475 nm with a shoulder at 530 nm (FIG. 2b). The emission band is red shifted by 90 nm from its usual 7 nm stokes shifted weak mirror image emission bands. This characteristic emission band is attributed to an excimer-like emission (excitation spectra not shown) due to the formation of ground-state aggregates.

The UV-Vis spectrum of L-NDI in 90% aqueous DMF and 90% aqueous DMSO, chloroform/methanol, dichloromethane/methanol, carbontetrachloride/methanol and acetonitrile/methanol is shown in FIG. 30 and FIG. 31.

EXAMPLE 4

H-Type Aggregation: Sodium Coordination

Solvent induced J-type aggregation is found to be affected by protecting the free carboxylic acid groups of NDI 1 with methyl esters as in NDI 2. In contradiction, deprotonation of carboxylic acid protons of NDI 1 with an alkali like sodium hydroxide shows surprisingly distinct results. To a 10% aqueous acetonitrile solution of NDI 1 (100 μM) NaOH is added in increments. The absorption bands for NDI 1 are at 341 nm, 358 nm and 379 nm respectively in the absence of NaOH (FIG. 1c). Successive addition resulted in a marginal bathochromic shift upto a total of 4 equiv of NaOH. With the further increase in addition of NaOH (5, 10, 20, 50 and 100 equiv) the absorption bands show a strong hypsochromy. The absorption spectrum of NDI 1 with 10 equiv of NaOH comprises of bands at 331 nm, 349 nm and 364 nm. With the help of intermediate spectral data, these bands were attributed to the hypsochromic shift of 341 nm, 358 nm and 379 nm absorption bands respectively. Thus a H-type aggregation mode is induced in NDI 1. Further increase in the NaOH content resulted in a very broad band. The anion of NDI 1 produced on treatment with NaOH should exert strong electrostatic repulsion and hence hinder agglomeration. The Na$^+$ mediated coordination with the anion of NDI 1 reduces the electrostatic repulsion. The strong hypsochromic shift observed is thus attributed to Na$^+$ coordination with NDI 1 anion. However NDI 2 on NaOH treatment resulted in the spectral features as shown in FIG. 1d. It is not surprising that NDI 2 showed absorption spectra similar to that of NDI 1 except for the initial slight bathochromic shift. Hydrolysis of methyl ester in NDI 2 by added NaOH generates sodium salt same as that obtained in case of NDI 1. The difference between the spectral features of NDI 1 and NDI 2 for the initial equiv of NaOH is explained by means of the resulting side products water and methanol from NDI 1 and NDI 2 respectively. The hydrophobic effect which has been shown to cause the bathochromic shift (FIG. 1a, 1b) is held responsible for the initial bathochromic shift observed in case of NDI 1 as water is the byproduct. However the weaker solvophobic interactions of methanol compared to water results in minimal bathochromic shifts as observed in case of NDI 2.

EXAMPLE 5

Circular Dichroism (CD) Studies

Figure 3:
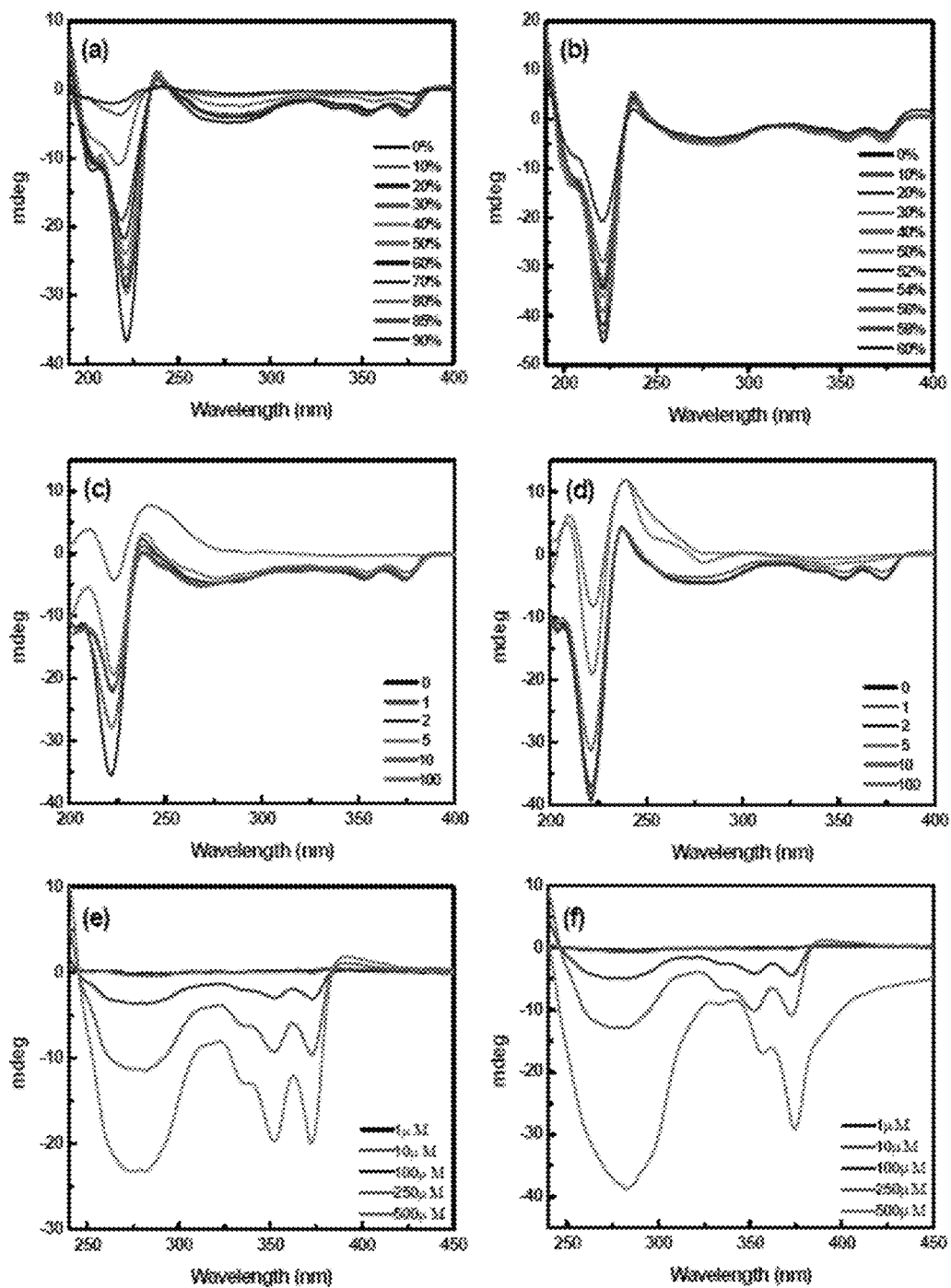

To gain further insight into the mode of aggregation CD studies on NDI 1 and NDI 2 were carried out. The CD spectrum of NDI 1 in acetonitrile solution (100 μM) shows intense negative bands at 221 nm with a shoulder at 202 nm and less intense bands at 276 nm, 335 nm, 352 nm and 372 nm (FIG. 3a). The negative bands at 221 nm and 202 nm are attributed to $n\pi^*$ and $\pi\pi^*$ transitions of imide chromophore respectively. The intense 221 nm band suggests possible additional contributions. The close proximity of $n\pi^*$ (221 nm) and $\pi\pi^*$ (202 nm) transitions can facilitate their mixing to a phenomena known as one electron effect and hence can enhance $n\pi^*$ bands. However the specific interactions with aromatic chromophores can also be responsible for the enhanced 221 nm band. The band centered at 276 nm is due to the $\pi\pi^*$ transitions of tryptophan while those at 335 nm, 352 nm and 372 nm are due to that of NDI imposed by a chiral chemical environment. The solvent dependant CD studies on the aggregation mode of NDI 1 are as shown in FIG. 3a. The negative band at 221 nm for NDI 1 in acetonitrile is shifted to 213 nm ($\Delta\lambda$=8 nm) in 90% aqueous acetonitrile solvent system. The $n\pi^*$ transition in amides is dependant on solvent and increased solvent polarity with the successive increments of water in acetonitrile shifts $n\pi^*$ transition towards lower wavelength region. The 221 nm ($n\pi^*$ transition) band is quenched preferentially with the solvent polarity than the 202 nm ($\pi\pi^*$ transition) band. The spectral band features of NDI 1 almost disappeared in 90% aqueous acetonitrile. The broad band centered at 276 nm is also found to quench with the solvent polarity without any shift in band position. The $\pi\pi^*$ transition bands of NDI at 335 nm, 352 nm and 372 nm are found to have a bathochromic shift to 337 nm, 357 nm and 378 nm respectively similar to the bathochromic shift observed during absorption spectroscopic studies (FIG. 1a). Thus the hydrophobic effect induced bathochromic shift of NDI CD bands can also be attributed for J-type aggregation. The CD study of hydrophobic effect on NDI 2 is shown in FIG. 3b. NDI 2 exhibit bathochromy with respect to NDI (ce) bands while a hypsochromy with respect to imide (221 nm) band similar to NDI 1. For 60% aqueous acetonitrile NDI 2 shows 1 nm hypsochromic shift of 221 nm band while ~1 nm bathochromic shift for 352 nm and 372 nm bands. The hypsochromic shift of the 221 nm band and the bathochromic shift of NDI bands observed in CD measurements are due to the different mechanisms involved.

Further, NDI 1 with NaOH is found to have a bathochromic shift of 221 nm negative band (FIG. 3c). A bathochromic shift of 2 nm is observed with 10 equiv of NaOH. The bands above 240 nm showed minimal changes for various equiv of NaOH. At 100 equiv of NaOH the bands above 240 nm completely disappeared. This is in agreement with the disappearance of the characteristic spectral features as observed in the absorption spectroscopic studies (FIG. 1c). Interestingly, the 202 nm band due to $\pi\pi^*$ transition of imide is found to have a hypsochromy. The NaOH mediated coordination of NDI 1 is believed to shift the 202 nm band to below 200 nm. In addition positive band like features is observed at 210 nm and 240 nm. The CD studies on NDI 2 with NaOH reveal spectral features similar to NDI 1 (FIG. 3d). A bathochromic shift of only 1 nm is observed for the 221 nm band in case of NDI 2.

Concentration dependant CD studies of NDI 1 and NDI 2 are shown in FIG. 3e and FIG. 3f respectively. The chiral field induced $\pi\pi^*$ transitions of tryptophan results in a very broad negative band centered at 276 nm. However, the chiral field induced $\pi\pi^*$ transitions of NDI results in negative bands at 335 nm, 352 nm and 372 nm. For low concentrations of NDI 1 (1 μM and 10 μM) in acetonitrile these characteristic bands above 240 nm are not observed. Unlike NDI 1, the CD spectrum of 500 μM NDI 2 shows bands at 282 nm, 356 nm and 375 nm. The concentration dependant bathochromic shift of bands>240 nm is attributed to J-type aggregation of NDI 2. The reduced solubility of NDI 2 is believed to aid in their molecular organization.

The CD spectrum of L-NDI (100 μM) shows intense band at 215 nm and less intense bands in the range of 225-400 nm (FIG. 2c). The 215 nm band is attributed to $n\pi^*$ transitions of imide chromophore. The less intense bands are due to band I and band II electronic transitions of L-NDI. The CD spectrum for a relatively higher concentration of L-NDI (1 mM) clearly shows the strong excitonic Cotton effect. [FIG. 2f] According to exciton chirality method the negative sign of the first Cotton effect reflects M-helicity of L-NDIs in acetonitrile. Interestingly in 90% aqueous acetonitrile flat CD features were observed (FIG. 2c). The increased hydrophobic forces impose π-π stacking of L-NDI chromophores. The observed CD silencing is thus attributed to the transition of the angles between the z-polarized transition moments of the stacked exciton-coupled L-NDI chromophores towards zero (FIG. 2e). On the other hand a complementary Cotton effect was observed for D-NDI (FIG. 2c) which exhibit P-helicity (positive sign of the first Cotton effect) in acetonitrile and CD silencing in 90% aqueous acetonitrile similar to that of L-NDI.

EXAMPLE 6

Vibrational Spectroscopic Studies

Figure 4:
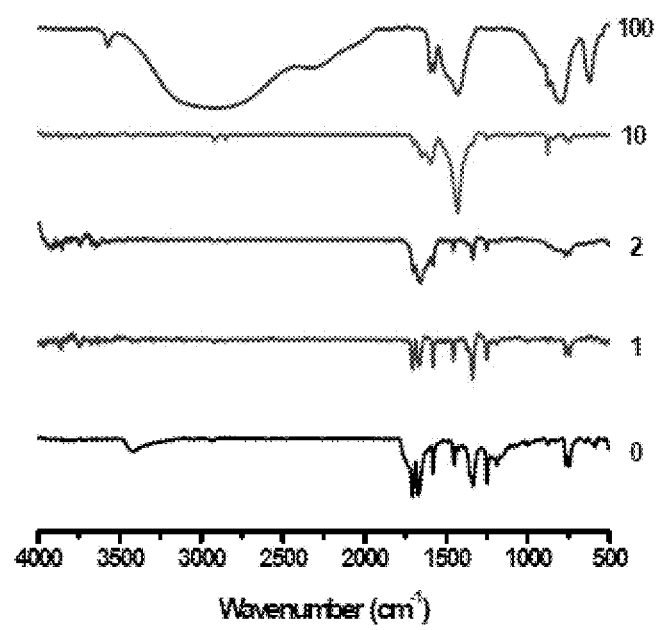
FIG. 4 shows IR spectra of NDI 1 (acetonitrile) with the addition of NaOH (in equiv).

Vibrational spectroscopic study of NDI 1 and NDI 2 further revealed the changes in their vibrational modes. NDI 1 exhibits vibrational absorption frequencies at 1580 cm$^{-1}$, 1670 cm$^{-1}$ and 1706 cm$^{-1}$ among others. The vibrational frequency at 1706 cm$^{-1}$ is assigned to $\nu_{C=O}$ of carboxylic acid groups, 1580 cm$^{-1}$ to aromatic $\nu_{C=C}$ and the 1670 cm$^{-1}$ peak is attributed to the imide $\nu_{C=O}$ vibrational frequency, commonly known as amide I band. The chemical environment constrained by conformation alters the amide I band. But the lack of conclusive structure-spectral correlations in the literature with their several exceptions complicates the unambiguous assigning of amide I bands with the corresponding secondary structure. On the basis of observed vibrational absorption frequency at 1670 cm$^{-1}$, NDI 1 is attributed to a class of β-turn conformation. NDI 1 in 90% aqueous acetonitrile shows peaks at 1580 cm$^{-1}$, 1666 cm$^{-1}$ and 1704 cm$^{-1}$ corresponding to aromatic $\nu_{C=C}$, imide $\nu_{C=O}$ and $\nu_{C=O}$ of carboxylic acid functional groups respectively. These changes in the vibrational frequencies are attributed to hydrophobic effect induced structural variations. However, in case of NDI 2 the peak at 1719 cm$^{-1}$ is attributed to ester $\nu_{C=O}$, 1580 cm$^{-1}$ peak to aromatic $\nu_{C=C}$ while the 1705 cm$^{-1}$ and 1678 cm$^{-1}$ to the imide $\nu_{cC=O}$ vibrational frequencies. NDI 2 showed slight changes in the vibrational modes in 60% aqueous acetonitrile. In another experiment NaOH is added in increments to an acetonitrile solution of NDI 1, the corresponding spectral changes are shown in FIG. 4. With successive addition of NaOH, the carboxylic acid $\nu_{C=O}$ and imide carbonyl $\nu_{C=O}$ are found to shift towards lower frequencies. The carboxylic acid $\nu_{C=O}$ is found to be at 1700 cm$^{-1}$ while the imide carbonyl $\nu_{C=O}$ at 1660 cm$^{-1}$ with 2 equiv of NaOH (deprotonation of carboxylic acid protons). For 100 equiv of NaOH, very broad vibrational modes at 620 cm$^{-1}$, 800 cm$^{-1}$, 1429 cm$^{-1}$, 1574 cm$^{-1}$, 1598 cm$^{-1}$ and ~3000 cm$^{-1}$ are observed. These changes in the vibrational modes clearly indicate the NaOH mediated coordination of NDI 1.

Similarly, the vibrational spectroscopic studies of L-NDI in 90% aqueous acetonitrile and in chloroform/methanol are shown in FIG. 24 and FIG. 25.

EXAMPLE 7

Nuclear Magnetic Resonance (NMR) Studies

Figure 5:
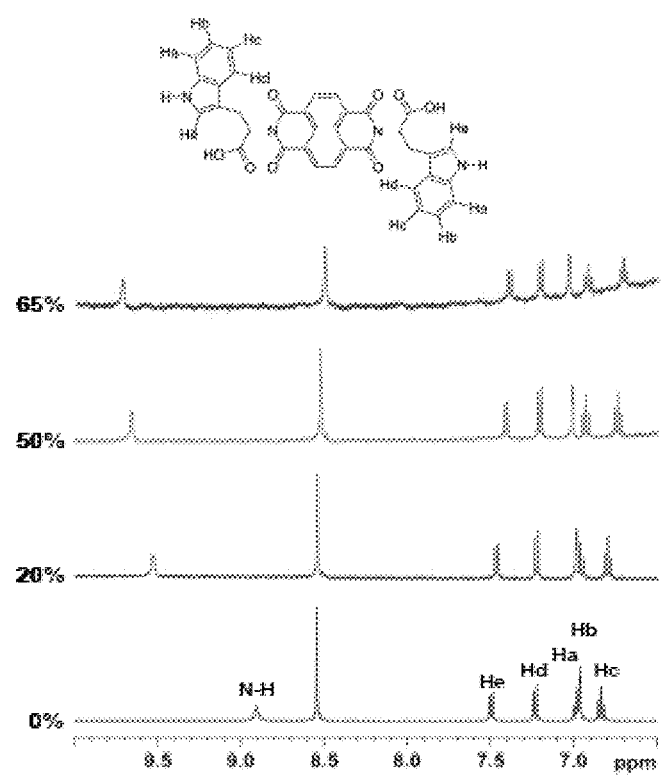
FIG. 5 shows chemical structure of NDI 1 with proton assignments (top) and 1H NMR spectra of NDI 1 in $CD_3CN$ with varying percentage of added water (0-65%).
Figure 6:
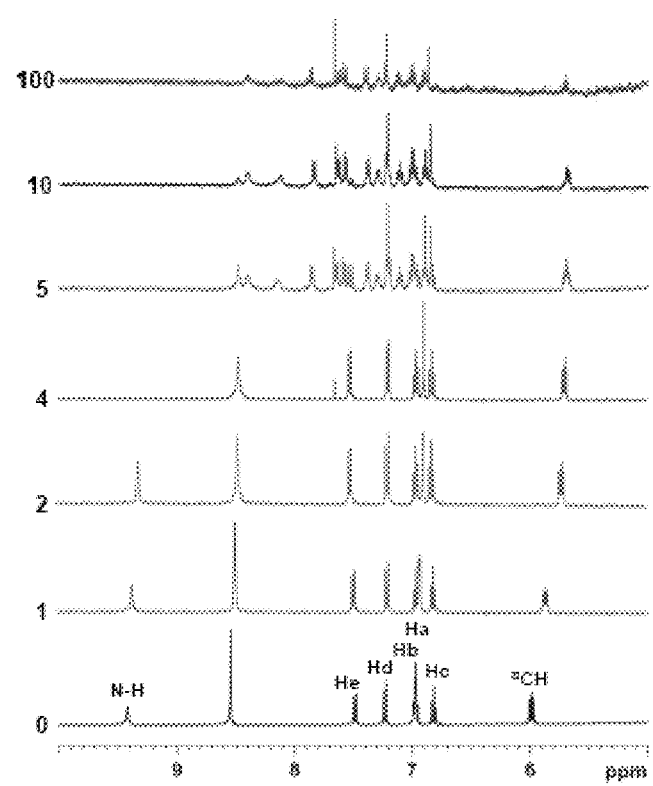
FIG. 6 shows $^1$H NMR spectra of NDI 1 in 10% aqueous $CD_3CN$ with increasing amount of added NaOH (0-100 equiv).

NMR spectroscopic investigation Vibrational spectroscopic study of NDI 1 and NDI 2 further revealed the changes in their vibrational modes. NDI 1 exhibits vibrational absorption frequencies at 1580 cm$^{-1}$, 1670 cm$^{-1}$ and 1706 cm$^{-1}$ among others. The vibrational frequency at 1706 cm$^{-1}$ is assigned to $\nu_{C=O}$ of carboxylic acid groups, 1580 cm$^{-1}$ to aromatic $\nu_{C=C}$ and the 1670 cm$^{-1}$ peak is attributed to the imide $\nu_{C=O}$ vibrational frequency, commonly known as amide I band. The chemical environment constrained by conformation alters the amide I band. But the lack of conclusive structure-spectral correlations in the literature with their several exceptions complicates the unambiguous assigning of amide I bands with the corresponding secondary structure. On the basis of observed vibrational absorption frequency at 1670 cm$^{-1}$, NDI 1 is attributed to a class of β-turn conformation. NDI 1 in 90% aqueous acetonitrile shows peaks at 1580 cm$^{-1}$, 1666 cm$^{-1}$ and 1704 cm$^{-1}$ corresponding to aromatic $\nu_{C=C}$, imide $\nu_{C=O}$ and $\nu_{C=O}$ of carboxylic acid functional groups respectively. These changes in the vibrational frequencies are attributed to hydrophobic effect induced structural variations. However, in case of NDI 2 the peak at 1719 cm$^{-1}$ is attributed to ester $\nu_{C=O}$, 1580 cm$^{-1}$ peak to aromatic $\nu_{C=C}$ while the 1705 cm$^{-1}$ and 1678 cm$^{-1}$ to the imide $\nu_{C=O}$ vibrational frequencies. NDI 2 showed slight changes in the vibrational modes in 60% aqueous acetonitrile. In another experiment NaOH is added in increments to an acetonitrile solution of NDI 1, the corresponding spectral changes are shown in FIG. 4. With successive addition of NaOH, the carboxylic acid $\nu_{C=O}$ and imide carbonyl $\nu_{C=O}$ are found to shift towards lower frequencies. The carboxylic acid $\nu_{C=O}$ is found to be at 1700 cm$^{-1}$ while the imide carbonyl $\nu_{C=O}$ at 1660 cm$^{-1}$ with 2 equiv of NaOH (deprotonation of carboxylic acid protons). For 100 equiv of NaOH, very broad vibrational modes at 620 cm$^{-1}$, 800 cm$^{-1}$, 1429 cm$^{-1}$, 1574 cm$^{-1}$, 1598 cm$^{-1}$ and ~3000 cm$^{-1}$ are observed. These changes in the vibrational modes clearly indicate the NaOH mediated coordination of NDI 1. further confirms the structural changes occurring during the course of NDI 1 aggregation. $^1$H NMR spectra for the solvent dependant aggregation of NDI 1 (aqueous CD$_3$CN solution) is shown in FIG. 5. The hydrophobic effect induced stacking of NDI 1 did not show significant changes in naphthalene core protons resonances. The aromatic component (indole) of tryptophan shows interesting changes. The indole N—H proton resonating at δ=8.91 ppm in CD$_3$CN undergo a downfield shift to δ=9.72 ppm in 65% aqueous CD$_3$CN. The labeled protons Hb, Hc, Hd and He experience an upfield shift. Ha undergoes a downfield shift. Therefore the J-type aggregation observed is pronounced more through tryptophan moieties. However the structural changes in NDI 1 in the presence of NaOH are clearly evident from the $^1$H NMR studies (FIG. 6). On incremental addition of NaOH, the indole N—H proton shifts toward lower δ values. At 4 equiv of NaOH the indole N—H disappears indicating the abstraction of protons by NaOH. The naphthalene core protons undergo an upfield shift. The $^\alpha$CH also experiences an upfield shift from δ=5.99 ppm to δ=5.69 ppm. The labeled protons Hb, Hc and Hd show minimal variations in the proton resonating frequencies. However Ha and He protons has slight upfield and downfield shifts respectively. Addition of more than 4 equiv NaOH brings about significant changes in the $^1$H NMR of NDI 1. Proton resonating frequencies observed in the aromatic region above 4 equiv of NaOH is a clear indication of the structural changes occurring due to the presence of NaOH. These structural changes are attributed to sodium coordinated variations which also involves cation-π interactions. $^1$H NMR studies shows the major variations in the proton resonances of tryptophan and hence tryptophan and its indole moieties play the crucial role in determining the mode of aggregation.

The results of NMR studies carried out on L-NDI and D-NDI are also shown in FIG. 26, FIG. 27, FIG. 28 and FIG. 29.

EXAMPLE 8

Morphological Studies

NDI 1 forms spherical aggregates from acetonitrile solution as shown in the FESEM micrograph (FIG. 7a). TEM micrograph clearly shows nanospheres of NDI 1 (FIG. 7b). A maximum of 6 nm bathochromic shift (NDI electronic transitions) in absorption as well as CD studies along with 8 nm hypsochromic shift of 221 nm band (CD) for NDI 1 in 90% aqueous acetonitrile, is obtained. Consequently, FESEM micrograph showed the formation of particles of NDI 1 from 90% aqueous acetonitrile (FIGS. 7c and 7d). AFM studies revealed the particles as triangular aggregate of 400 nm dimension with a typical height of ~40 nm.

The interplay between hydrogen bonding, solvophobic forces and aromatic stacking decides the molecular organization and hence their morphology. The intermolecular hydrogen bonding between carboxylic acid groups of NDI 1 in cooperation with the solvophobic and aromatic interaction leads to nanospheres in acetonitrile solution. The presence of water in aqueous acetonitrile solution of NDI 1 disrupts the intermolecular hydrogen bonding. The mutual interactions involving solubility due to carboxylic acid groups and the hydrophobic effect induced aromatic interaction leads to J-type aggregation. The particles are believed to be formed from disordered organization of J-type aggregates as indicated by absorption and morphological studies.

NDI 2 also forms the spherical aggregates from acetonitrile solution as shown in FIGS. 8a and 8b. The presence of methyl ester of tryptophan in NDI 2 shows no significant changes in the aggregation mode with respect to NDI 1 from acetonitrile solution. From the absorption spectroscopic study a bathochromic shift of not more than 2 nm for the NDI ππ* transitions, a hypsochromic shift of 1 nm for the 221 nm (CD) band is observed. Surprisingly the molecular self-assembly of NDI 2 from 60% aqueous acetonitrile differs distinctly. NDI 2 forms fibers from 60% aqueous acetonitrile. FESEM micrograph with high aspect ratio fibers (bundle of nanobelts) is shown in FIG. 8c and 8d. FIG. 9 show AFM images of NDI 2 and the corresponding height profile as the insets. In FIG. 9a an AFM image revealing the transformation of NDI 2 nanospheres (D=~400 nm, Height=29 nm) into nanobelts and in turn into microfibers is showed. The inset in FIG. 9a is the corresponding height profile. These nanobelts bundle together to form long fibers of few 100 nm to few micrometers thickness (FIG. 9b). The formation of spherical aggregates from NDI 2 suggests that intermolecular hydrogen bonding (carboxylic groups) need not be a necessary clause as the aggregation is mainly facilitated by solvophobic and aromatic interactions. However the presence of methyl ester reduces the partial solubility rendered in water and moreover the dominance of hydrophobic forces in cooperation with aromatic interaction leads to 1D aggregation.

Analogous to the morphological changes induced by the bathochromic shift due to hydrophobic effect, NaOH too is found to affect the morphology. Deprotonation of carboxylic acid protons in NDI 1 is hardly found to have any significant change in the absorption spectra. But the deprotonation results in drastic changes in the morphology of NDI 1. With 2 equiv of NaOH, the formation of sodium salt with NDI 1 anion results in the formation of fractals (FIG. 7e, 7f). For 10 equiv of NaOH, distinct microstructures of NDI 1 are formed. With further increase of NaOH (100 equiv) particulate like agglomeration of NDI 1 is observed. NDI 2 also results in similar fractals for 2 equiv of NaOH and agglomerated masses for 100 equiv of NaOH. The morphological changes as a function of concentration of NDIs are also studied. At a relative higher concentration (1 mM) NDI 1 agglomerates. However 1 mM NDI 2 transforms into 1D nanobelts (FIG. 10). The reduced solubility and the enhanced solvophobic forces are believed to enforce 1D assembly of NDI 2 (1 mM) aromatic cores into J-type aggregates as indicated by CD studies (FIG. 3f).

Field emission scanning electron microscopy (FESEM) revealed the formation of sheets with micrometer large lateral dimension from 90% aqueous acetonitrile solution of L-NDI (FIG. 11a). Similarly D-NDI also self-assemble to form sheets in 90% aqueous acetonitrile (FIGS. 20a and 20b). Furthermore free-standing sheets of L or D-NDI (100 µM, 90% aqueous acetonitrile) is obtained within an hour of sample preparation. Such solution processing leads to an economically viable, highly tunable and ecologically safe production of sheets in ambient conditions without the need for sophisticated instrumentation. Thus formed free-standing sheet is an illustration of a successful molecular design and engineering with the optimal utilization of non-covalent interactions. Further, the sheets are further tuned by employing different solvent systems. In 90% aqueous DMF, L-NDI organizes to form elongated sheets with ~100 µm length and 2-10 µm breadth [FIG. 12]. On the contrary in 90% aqueous DMSO, L-NDI organizes to form relatively smaller (length ~2-10 µm) but thicker sheets (thickness ~500 nm). [FIG. 12]

In FIG. 11b shows the confocal micrograph of L-NDI sheets with bluish intrinsic fluorescence. The observed fluorescence is due to excimer-like emission as evident from the fluorescence spectroscopy studies. High resolution transmission electron microscopy (HRTEM) reveals homogeneously flat L-NDI nanosheets (FIG. 11c). The selected area electron diffraction (SAED) recorded on these nanosheets exhibit well resolved hexagonal spots (inset, FIG. 11c). Moreover powder X-ray diffraction (PXRD) studies on L-NDI nanosheets show very high crystallinity along with a d spacing of 3.68 Å corresponding to π-π stacking (FIG. 11d). Atomic force micrograph of L-NDI sheets is shown in FIG. 3e, with typical height of 10 nm for a representative sheet as revealed by the height profile (FIG. 11f). However the topographical thickness (height) of these self-assembled nanosheets are in the range of 10-100 nm. [FIG. 13] Conductive atomic force microscopy (C-AFM) technique is employed to study the conductivity of individual self-assembled nanosheets. Remarkably, the current-voltage (I-V) characteristics of all measured L-NDI nanosheets display metallic conductivity. These I-V features are consistent throughout the length and breadth of nanosheets indicating persistent molecular ordering. A remarkable conductivity of 1.6 Scm$^{-1}$ is obtained for a nanosheet with the topographical thickness of 60 nm [FIG. 1B(d)]. Such metallic conductivities are reported only in heavily doped conducting polymers and small molecules. Furthermore most of the organic semiconductors that exhibit high mobility (e.g. pentacene) adopt edge-to-face herringbone structure with reduced intermolecular electronic couplings. The observed metallic conductivity is attributed to the presence of high-level molecular ordering in L-NDI nanosheets. The molecular planarity of NDI core and ground-state molecular aggregation (excimer-like emission, CD silencing and diffraction data) is envisioned to yield such high-level molecular ordering. The proposed model for the molecular packing of L or D-NDI is shown in FIG. 14. The methylester of phenylalanine in L or D-NDI system initiates the molecular organization as a result of enhanced hydrophobic forces in 90% aqueous acetonitrile. The L-NDI chromophores undergo 1D π-π stacking in a direction perpendicular to the nanosheet surface. However phenyl-ring of phenylalanine facilitates lateral organization to form 2D nanosheet architectures through interdigitation.

The single crystals of L-NDI are grown in chloroform. The crystal structure comprises of crystalline chloroform (FIG. 14e). The chlorine atoms are found to have an attractive interaction with the carbonyl oxygen of methyl ester (3.02 Å, blue dotted line) and carbonyl oxygen of naphthalenediimide (3.19 Å, green dotted line) in L-NDI by means of halogen bonding (FIG. 14e). Halogen bonding is a highly directional non-covalent interaction (10-200 kJmol$^{-1}$) which arises as a result of positive electrostatic potential developed along the carbon-halogen covalent bond. This σ-hole acts as an electrophillic species pulling the donor lone pair electrons closer towards the halogen atom and accounts for the orientation of the halogen bonds. Experimental studies confirm the theoretical prediction that electron density is anisotropically distributed around the halogen atom in organic halides. The studies using chloroform as co-solvent result in interesting morphological changes. In chloroform alone as a solvent L-NDI results in random aggregates. However in 50% (v/v) chloroform/methanol, L-NDI organizes into cups of ~400 nm lateral width (FIG. 15a). Interestingly these cups were homogeneously distributed throughout the substrate. Furthermore in 10% (v/v) chloroform/methanol, L-NDI organizes into bigger cups with ~800 nm lateral width (FIG. 15b, 21a, 21b, 21c, 21d). These bigger cups are envisioned to be formed by the fusion of smaller cups (lateral width ~400 nm). A typical bigger cup formation involves the fusion of about 4 to 6 smaller cups. In methanol alone as a solvent, organization of L-NDIs to spherical structures was observed. [FIG. 16] Hence chloroform has profound influence on the mode of aggregation. For further verification, other chlorinated solvents dichloromethane and carbon tetrachloride. L-NDI formed cups of ~700 nm in 10% (v/v) dichloromethane/methanol. [FIG. 17] However 10% (v/v) carbontetrachloride/methanol results in bowl (1.5-2 μm) like architectures (FIG. 15c, 22a, 22b, 22c). Moreover in 10% (v/v) chloroform/acetonitrile L-NDI formed spherical aggregates. On the other hand acetonitrile dispersion of L-NDI when mixed with chloroform resulted in cups of 300-700 nm lateral dimensions. [FIG. 18] These results clearly suggest that chlorinated co-solvents play crucial role in the molecular organization of L-NDI into molecular containers.

AFM studies on L-NDI cups obtained from 50% (v/v) chloroform/methanol reveal overall diameter (thickness) of 400-500 nm with exterior topographical height in the range of 40-80 nm (FIG. 14d, 23a). The interior of the cup possess typical height of 10-40 nm with an internal diameter (FWHM-full width at half maximum) of 90-200 nm. AFM micrograph of these nanocups is shown in FIG. 15d. The corresponding height profiles in FIGS. 15e, 15f, 23b and 23c accounts for a net volume of 0.58 (V1), 0.6 (V2), 0.19 (V3) and 0.2 (V4) attoliters. The average volume capacity for the measured nanocups ranges from 0.1 to 1.5 attoliters. To demonstrate the utility a femtojet technique is used to randomly fill fluorescent dyes into L-NDI containers on a glass substrate. Under appropriate experimental conditions femtojet can inject liquid droplets of nanometer dimension. Dilute solutions of the analyte appended with fluorescent dyes are commonly employed for biological assays. Herein by using femtojet technique fluorescent dyes like rhodamine and fluorescein are filled into several L-NDI containers and visualized under confocal microscope. [FIG. 19].

Inner volume (v) of the container (FIG. 56) is calculated using the following formula, $$V=h*b*l$$

Where, h (height) is the inner topographical height (10-40 nm) of the L-NDI nanocup. Both l (length) and b (breadth) are considered to be same and equal to FWHM (full width at half maximum). The h, b and l values are obtained from the corresponding AFM height profiles.

This illustrates the probable usage of ultra-small containers for performing miniaturized biological assays.

EXAMPLE 9

X-Ray Crystallography Studies

A suitable yellow colour single crystal is carefully selected under a polarizing microscope and fixed to a separate thin glass fiber by commercially available glue. X-ray single crystal structural data is collected by a Bruker Smart-CCD diffractometer equipped with a normal focus, 2.4 kW sealed tube X-ray source (Mo Kα radiation, 0.71073 Å) operating at 50 kV and 30 mA. The programme SAINT is used for integration of diffraction profiles and an empirical absorption correction based on symmetry equivalent reflections is applied using the SADABS program. The structure is solved by direct method using SIR92 programme and refined by full matrix least square method using SHELXL 97. The hydrogen atoms are fixed by HFIX and placed in ideal positions. Potential solvent accessible area or void space is calculated using the PLATON 99 multipurpose crystallographic software. Final refinement included atomic positions for all the atoms, anisotropic thermal parameters for all the non hydrogen atoms. All calculations are carried out using WinGX system, Ver 1.70.01. The coordinates, anisotropic displacement parameters, and torsion angles for L-NDI are determined from the crystal structure as shown in FIG. 32.

EXAMPLE 10

Synthesis of Peptide Appended NDIs

N,N bis-(dipeptide) appended 1, 4, 5, 8-Naphthaienedinides (4, 5 and 6) is synthesised according to FIG. 35.

N,N-bis-(dipeptide) appended NDIs (4, 5 and 6) are synthesized and characterised by Matrix-assisted laser desorption ionization (MALDI) and Nuclear magnetic resonance spectroscopy ($^1$H NMR, $^{13}$C NMR). Self-assembly properties are studied in different solvent systems. The resulting self-assembled structures are characterized using various spectroscopic and microscopy techniques.

Self-Assembly Studies

In the present disclosure, the self-assembly of NDIs 4, 5 and 6, are investigated in various polar and mixture of polar and non polar solvents such as chloroform, DMSO (dimethyl sulfoxide), CHCl$_3$/MeOH(methanol), CHCl$_3$/MCH(methylcyclohexane) and DMSO/H$_2$O respectively. UV-vis absorption spectroscopy, photoluminescence spectroscopy and scanning electron microscopy (SEM) are used to investigate electronic and self-assembling properties of NDIs to form nanostructures with well defined architectures.

Absorption and Emission Studies

Electronic absorption spectra are recorded on a Perkin Elmer Lambda 900 UV-VIS-NIR Spectrometer and emission spectra are recorded on Perkin Elmer LS55 Luminescence Spectrometer. UV-vis absorption and emission spectra are recorded in 10 mm path length cuvette. Fluorescence spectra of solutions are recorded with 380 nm excitation wavelength.

The UV-vis absorption and emission spectra of molecularly dissolved NDI 4 in chloroform ($CHCl_3$ known to be a good solvent for $\pi$ systems) and DMSO (hydrogen bond accepting solvent) showed the typical spectral features of N,N di-substituted NDI molecule as reported in the literature (FIG. 34). The absorption spectra of 4 in chloroform ($5\times10^{-5}$M) showed a broad band with shoulder at 340 nm, two maxima at 361 nm and 381 nm (FIG. 36a (i) red curve) which are the characteristic of z-polarized $\pi$-$\pi$* transitions in NDI chromophore. In DMSO also NDI 4 ($5\times10^{-5}$M) showed almost similar spectral features with $\lambda_{max}$ at 340 nm, 361 nm and 381 nm (FIG. 36b (i) red curve). The emission spectra is mirror image to absorption spectra in chloroform for NDI 4 ($5\times10^{-5}$M) showed broad band with two maxima at 408 nm and 432 nm (FIG. 36a (ii) black curve). Where as in DMSO the intensity of emission spectra is slightly decreased (FIG. 36b (ii), black curve). Since the absorption and emission spectra in chloroform and DMSO are almost identical (except with some minor changes) it can be considered that NDI 4 did not form self-assembled aggregates in these solvents. Similar spectral features are observed in the case of NDIs 5 and 6 as shown in FIGS. 36 (c, d) and (e, f) respectively.

In the present disclosure, in order to gain further insight into the aggregation behaviour of NDIs 4, 5 and 6, detailed absorption and emission spectral studies are carried out in presence of mixture of solvent systems such as $MCH/CHCl_3$, $MeOH/CHCl_3$ and $H_2O/DMSO$. Here, MCH is known to facilitate the $\pi$-$\pi$ stacking and hydrogen bonding between the molecules, MeOH will break the hydrogen bonding but it can enhance the $\pi$-$\pi$ stacking between the molecules. While $H_2O$ is a highly polar solvent and due to solvophobic effects organic molecules are expected to form self-assembled aggregates in this solvent.

EXAMPLE 11

NDI 4 [N,N-bis-(Phe-Phe-OMe) Appended NDI]

$MCH/CHCl_3$ Solvent System

UV-vis absorption and emission studies of NDI 4 in $MCH/CHCl_3$ solvent system at $5\times10^{-5}$ M concentration is shown in FIG. 37. In $CHCl_3$, NDI 4 showed a broad absorption band with two maxima at 361 nm and 381 nm, which is characteristic of molecularly dissolved (un-assembled molecules) NDIs. However, in $MCH/CHCl_3$ (95:5) a slight (3 nm) blue shift (hypsochromic shift) in absorption maxima (FIG. 37a) was observed, suggesting the self-assembly of NDIs. More interestingly emission studies upon addition of MCH to $CHCl_3$ (95:5) showed an eximer like emission at 482 nm which is not observed in $CHCl_3$ solution (FIG. 37b). FIG. 37 show UV-vis absorption and emission spectra and their corresponding scanning electron microscopic (SEM) images of NDI 4 in $MCH/CHCl_3$ (95:5) solvent system.

Morphological Studies

Morphological studies of NDI 4 indicates the formation of spherical aggregates from $MCH/CHCl_3$ (95:5) solvent system as shown in the SEM micrograph (FIGS. 37b and 37c). The non-covalent interactions such as hydrogen bonding, solvophobic forces and aromatic $\pi$-$\pi$ it stacking decides the molecular organization and hence their morphology. The intermolecular hydrogen bonding between amide groups of NDI 4 and cooperative aromatic $\pi$-$\pi$ it interaction leads to formation of nanospheres in $MCH/CHCl_3$ (95:5) solution.

From these results, it is clear that the NDI 4 undergo molecular self-assembly in $MCH/CHCl_3$ (95:5, $5\times10^{-5}$ M) solvent system. At high volume percent of MCH (95%) in $CHCl_3$ (5%), NDI 4 exist as self-assembled spherical aggregate which corresponds to slight blue shift in absorption maximum and eximer formation due to ground state aggregation. Whereas, in $CHCl_3$, NDI 4 exist as a molecularly dissolved form (un-aggregate form) and hence suggest that MCH induces self-assembly between NDI 4 molecules through $\pi$-$\pi$ and amide hydrogen bonding.

$MeOH/CHCl_3$ Solvent System

With the addition of 95% MeOH to $CHCl_3$ solution of NDI 4, decrease in absorbance and fluorescence intensity is observed as shown in FIG. 38 (a and b). It is a clear indication of transformation of NDI 4 from molecularly dissolved state (in $CHCl_3$) to aggregate state (in 95% MCH) through noncovalent $\pi$-$\pi$ interactions.

SEM micrograph shows the formation of novel architectures with vesicular in $MeOH/CHCl_3$ (95:5, $5\times10^{-5}$) solvent system (FIGS. 39a and 39b). From these observation, it is concluded that MeOH assist to break amide hydrogen bonding and facilitates the $\pi$-$\pi$ it interactions between the NDI 4 molecules. The $\pi$-$\pi$ it staking is the main driving force for the NDI 4 to form vesicular nanostructures.

$H_2O/DMSO$ Solvent System

NDI 4 in $H_2O/DMSO$ solvent system shows slight red shift in the absorbance spectra and an intresting eximer formation at 482 nm (FIGS. 40a and 40b). SEM micrographs reveales that NDI 4 self-assemble into 1D nanostructure in this solvent system as shown in FIG. 40 (c and d). Addition of water induces hydrophobic effect on planar it conjugated NDI core and aromatic side chains on dipeptides and NDI 4 tries to minimise the total surface area exposed to polar medium (water). In this process, NDI 4 undergoes molecular $\pi$-$\pi$ it stacking in a highly directional fashion to form one dimensional nanostructures.

Thus, the present disclosure discloses the ability of inducing well defined molecular organisation and morphology control mediated by molecular recognition. The present disclosure also discloses the possibility of successfully tuning the morphology of NDI 4 in to well-defined architectures including nanospheres, open mouth nanovesicles and 1-D nanotapes through solvation processing by cleverly choosing solvent system.

EXAMPLE 12

NDI 5 [N,N-bis-(Phe-trp-OMe) Appended NDI]

$MCH/CHCl_3$ and $H_2O/DMSO$ Solvent System

UV-vis absorption and photoluminescence studies are performed for NDI 5 in the same solvent systems ($MCH/CHCl_3$, $H_2O/DMSO$ and $MeOH/CHCl_3$) that are used in the case of NDI 4. With the addition of MCH to $CHCl_3$ solution of NDI 5, the UV-vis absorption spectra shows slight red shift along with decrease in absorbence (FIG. 41a). However increase in the photoluminescence intensity is observed (FIG. 41b).

Photophysical studies suggest the self-assembly of NDI 5 in this solvent system. However, with the addition of $H_2O$ to the solution of NDI 5 in DMSO there is no eximer like emission (FIG. 41d).

$MeOH/CHCl_3$ Solvent System

The photophysical and SEM studies of NDI 5 in (95:5) $MeOH/CHCl_3$ solvent system is shown in FIG. 42. NDI 5 exhibit similar spectral (absorbance and emission) and morphological features to that of NDI 4 (FIGS. 42a and 42b).

SEM micrograph shows the formation of open mouth nanovesicles (FIGS. 43a and 43b)

EXAMPLE 13

NDI 6 [N,N-bis-(Trp-Trp-OMe) Appended NDI]

MCH/CHCl$_3$ Solvent System

UV-vis absorption and photoluminescence studies are done for the NDI 6 in MCH/CHCl$_3$ solvent system. With the addition of MCH to solution of NDI 6 in CHCl$_3$, the intensity of absorbance significantly decreases and increase in fluorescence intensity is observed as shown in the FIGS. 44a and 44b. SEM micrograph reveals the presence of three dimensional aggregates (nanocubes) of NDI 6 in this solvent system (FIGS. 44c and 44d).

MeOH/CHCl$_3$ and H$_2$O/DMSO Solvent System

In H$_2$O/DMSO, NDI 6 forms three dimensionally organized self-assembled nanocubes as shown in FIG. 45e. This suggests that the π-π stacking is the main driving force for the self-assembly of NDI 6 to form nanocubes in polar as well as non-polar solvents.

Proposed Mechanism

Based on the photophysical and morphological data of NDIs 4, 5 and 6, the present disclosure proposes the schematic model to explain the various nanostructures formed by N,N-bis-(dipeptide) appended NDI systems as illustrated in FIG. 46. SEM images reveals the existence of self-assembled nanodimensional structures with well defined morphologies. In a single solvent system (acts as a good solvent) like CHCl$_3$ and DMSO, molecules of NDIs 4, 5 and 6 are fully solvated hence the molecules are randomly oriented in all possible directions. By the addition of a poor solvent, it will induce the solvophobic effect on the NDIs 4, 5 and 6 molecules. To overcome solvophobic effect, molecules of NDIs 4, 5 and 6 try to come closer and closer in order to minimise the total surface area exposed to solvent molecules. At certain distance, the π-π interactions and hydrogen bonding between the molecules start forming, which will arrange the molecules into the proper direction as shown in FIG. 46. Stacked molecules of NDIs 4, 5 and 6 are further organised to form a self-assembled two dimensional nanostructures of different dimensions. The geometrically-restricted interactions of the aromatic moieties and their complex hydrophobic and electrostatic nature and various changes in the electronic environment of the aromatic system in the context of very small peptide, can significantly affect the organization of the assembled NDIs. The final morphology of NDIs 4, 5 and 6 depend on direction of folding or organisation of initially self-assembled NDI structure. For example, three dimensional arrangements of initial self-assembly structure will lead to the formation of 3D nanocubes. If the arrangement is one dimensional, then one dimensional nanotape formation is seen. FIG. 46 shows schematic model for various possible ways of organization of NDIs 4, 5 and 6 to form nanostructures of zero-, one-, two- and three-dimension with well defined morphology.

Conclusion

In the present disclosure, N,N-bis-(dipeptide) appended naphthalenediimides (NDIs) 4, 5 and 6 are designed and synthesized. NDIs 4, 5 and 6 undergo self-assembly to form interesting new novel nanostructures with well defined architectures. Morphology of NDIs nanostructure are tuned by utilising solvophobic effect. In the present disclosure, tuning the morphology into distinct structures such as nanospheres, nanotapes, open mouth nanovesicles and nanocubes is successfully carried out. These NDI-dipeptide conjugate based nanostructures may find potential applications as biomaterials and in organic electronics.

General Experimental Procedure

All the solvents and reagents were obtained from Sigma-Aldrich and used as received, unless otherwise mentioned. $^1$H and $^{13}$C NMR spectra were measured on a Bruker AV-400 spectrometer with chemical shifts reported as ppm.

EXAMPLE 14

Synthesis of L-Phenylalanine-Appended Naphthalenediimide (1)

L-phenylalanine (610 mg, 3 mmol) and NDA-dianhydride (500 mg, 1.8 mmol) is dissolved in dry DMF (30 ml). After 15 min triethyl amine is added to reaction mixture and allowed to reflux at 110° c. for 12 h. After cooling to room temperature, the solvent is removed under reduced pressure and washed with water. The organic layer is separated out and purified by column chromatography (CH$_2$Cl$_2$: MeOH 10:2) to afford product as brown solid (68%); Characterization data: $^1$H NMR (CHCl$_3$-d, 400 MHz) δ$_H$ 3.30-3.55 (m, 4H, CH$_2$), 5.69-5.73 (m, 2H, CH), 6.86-7.05 (m, 10H, ArH), 8.49 (m, 4H, ArH).

EXAMPLE 15

Synthesis of L-Tryptophan-Appended Naphthalenediimide (2)

L-Tryptophan (760 mg, 3.7 mmol) and NDA-dianhydride (500 mg, 1.8 mmol) is added to dry DMF (30 ml) in a 250 ml conical flask. Triethyl amine (0.5 ml) is added to suspension and sonicated until the reaction mixture become homogeneous. The reaction mixture is heated under microwave irradiation at full power for 3 min in steps of 30 sec and with 30 sec interval. The resulting dark brown oil is taken into methanol (400 mL). The solution is added under stirring to 600 ml of 1N HCl. The resulting suspension is allowed to coagulate overnight and then filtered through a sintered glass funnel. The solid is then washed with 200 mL deionised water and dried in vacuo to obtain a brown solid of (2). Yield 90%.

EXAMPLE 16

General Procedure for the Synthesis of N,N-Bis-(Dipeptide) Appended NDIs (4, 5 and 6)

Amino acid appended naphthalenediimide (300 mg, 0.5 mmol), 1-ethyl-3-(3 dimethylaminopropyl) carbodiimide hydrochloride (220 mg, 1.1 mmol) and 1-hydroxybenzotriazole (230 mg, 1.1 mmol) are dissolved in DMF (4 ml). After 15 min amino acid methylester (230 mg, 1 mmol) and N,N-diisopropylethylamine (440 mg, 3.4 mmol) are added to reaction mixture and allowed to stir at room temperature for 12 h. Reaction progress is monitored by TLC. The solvent is removed under reduced pressure and washed with water. The organic layer is separated out and purified by column chromatography (CH$_2$Cl$_2$: MeOH, 10:2).

Characterization data: NDI 4. Yield 50%, $^1$H NMR (CDCl$_3$, 400 MHz) δ$_H$ 3.00-3.51 (m, 8H, CH$_2$), 3.74 (m, 6H, CH$_3$), 4.89-4.94 (m, 2H, NH), 5.96-6.20 (m, 4H, CH), 6.90-7.26 (m, 20H, ArH), 8.63 (s, 4H, ArH); $^{13}$C NMR (CDCl$_3$, 400 MHz) δ$_C$ 34.6, 37.7, 52.3, 53.3, 55.9, 126.6, 128.3, 128.9, 131.1, 136.3, 136.6, 162.4, 171.6. MW. 884.93 [M+H$^+$] calcd for C$_{52}$H$_{44}$N$_4$O$_{10}$.

NDI 5. Yield 40%, $^1$H NMR (CDCl$_3$, 400 MHz) $\delta_H$ 3.13-3.60 (m, 8H, CH$_2$), 3.72 (m, 6H, CH$_3$), 4.87-5.01 (m, 2H, NH), 5.96-6.46 (m, 4H, CH), 6.65-7.55 (m, 19H, ArH), 8.34-8.40 (m, 2H, NH), 8.43-8.47 (m, 4H, ArH). MW. 962.09 [M+H$^+$] calcd for C$_{56}$H$_{46}$N$_6$O$_{10}$.

NDI 6. Yield 40%, $^1$H NMR (CDC/lhd 3, 400 MHz) $\delta_H$ 2.87-3.40 (m, 8H, CH$_2$), 3.59 (m, 6H, CH$_3$), 4.59 (s, 2H, NH), 5.74 (s, 2H, CH), 6.78-7.42 (m, 20H, ArH), 8.38-8.54 (m, 4H, ArH), 10.59-10.86 (m, 4H,NH); $^{13}$C NMR (CDCl$_3$, 400 MHz) $\delta_C$ 23.6, 26.5, 109.5, 110.2, 11.1, 111.3, 117.6, 117.9, 118.1, 118.3, 120.6, 120.8, 123.3, 123.6, 125.9, 126.3, 126.9, 127.1, 130.3, 135.8, 136.0, 168.6, 172.5. MW. 1,041[M+H$^+$] calcd for C$_{60}$H$_{48}$N$_8$O$_{10}$.

The instant disclosure thus describes the tuning of self assembly of naphthalene diimide derivatives. The disclosure uses various solvent and co-solvent systems that manipulate the non-covalent interactions between the molecules and influence the self-assembly of naphthalene diimide derivatives into various nano, meso and microstructures.

We claim:

1. A method of self-assembling naphthalene diimide derivative into nano, meso or micro structures, said method comprising:

dissolving the naphthalene diimide derivative in a solvent to form a solution; and adding co-solvent to the solution to obtain the self-assembled nano, meso or microstructures, wherein, said naphthalene diimide derivative is selected from a group consisting of derivatives of amino acids, methyl esters of amino acids and peptide or any combination thereof.

2. The method as claimed in claim 1, wherein the amino acid is selected from a group comprising phenylalanine and tryptophan.

3. The method as claimed in claim 1, wherein the peptide is selected from a group comprising phenylalanine-phenylalanine, tryptophan-tryptophan and phenylalanine-tryptophan or any combination thereof.

4. The method as claimed in claim 1, wherein the solvent is selected from a group comprising acetonitrile, methanol, dimethylsulfoxide and dimethylformamide.

5. The method as claimed in claim 1, wherein the co-solvent is selected from a group comprising water, chloroform, dichloromethane, carbon tetrachloride and sodium hydroxide or any combination thereof.

6. The method as claimed in claim 1, wherein the method is carried out at a temperature ranging from 0° C. to 100° C.

7. The method as claimed in claim 1, wherein the method is carried out at a temperature ranging from 20° C. to 30° C.

* * * * *